(12) United States Patent
Rajagopal et al.

(10) Patent No.: US 9,284,593 B2
(45) Date of Patent: Mar. 15, 2016

(54) LIVE BIOLOAD DETECTION USING MICROPARTICLES

(75) Inventors: Raj Rajagopal, Woodbury, MN (US); Kurt J. Halverson, Lake Elmo, MN (US); Manjiri T. Kshirsagar, Woodbury, MN (US); James E. Aysta, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/519,270

(22) PCT Filed: Dec. 30, 2010

(86) PCT No.: PCT/US2010/062517
§ 371 (c)(1),
(2), (4) Date: Jun. 26, 2012

(87) PCT Pub. No.: WO2011/082309
PCT Pub. Date: Jul. 7, 2011

(65) Prior Publication Data
US 2013/0029324 A1    Jan. 31, 2013

Related U.S. Application Data

(60) Provisional application No. 61/291,301, filed on Dec. 30, 2009, provisional application No. 61/331,931, filed on May 6, 2010.

(51) Int. Cl.
*C12M 1/34* (2006.01)
*C12Q 1/04* (2006.01)
(Continued)

(52) U.S. Cl.
CPC . *C12Q 1/04* (2013.01); *B01L 3/502* (2013.01);
*G01N 33/5005* (2013.01); *B01L 3/5029* (2013.01); *B01L 3/5082* (2013.01);
(Continued)

(58) Field of Classification Search
CPC ............ B01L 3/567; B01L 2400/0644; B01L 3/5029; G01N 1/4044; B65D 26/06; B65D 26/085; A61J 1/2037; A61J 1/20375
USPC .............. 435/287.6, 309.1; 600/572; 422/406
See application file for complete search history.

(56) References Cited

U.S. PATENT DOCUMENTS 3,481,712 A    12/1969  Bernstein et al.
3,745,090 A    7/1973   Chappelle et al.
(Continued)

FOREIGN PATENT DOCUMENTS

CN    1882697 A    12/2006
DE    1 442 223    11/1969
(Continued)

OTHER PUBLICATIONS

Berry, E.D. et al.; "Hydroxyapatite Adherence as a Means to Concentrate Bacteria"; Applied and Environmental Microbiology; vol. 63, No. 10; 1997; pp. 4069-4074.
(Continued)

*Primary Examiner* — William H Beisner
(74) *Attorney, Agent, or Firm* — Qiang Han

(57) ABSTRACT

The present invention provides methods to concentrate cells onto microparticles, to concentrate the microparticles, and to detect the cells. The present invention also includes unitary sample preparation and detection devices to be used in accordance with the methods.

8 Claims, 18 Drawing Sheets

(51) Int. Cl.
*B01L 3/00* (2006.01)
*G01N 33/50* (2006.01)
(52) U.S. Cl.
CPC ...... *B01L2300/042* (2013.01); *B01L 2300/046* (2013.01); *B01L 2300/0672* (2013.01); *B01L 2300/087* (2013.01); *B01L 2400/0478* (2013.01); *B01L 2400/0644* (2013.01); *B01L 2400/0683* (2013.01)

(56) References Cited

U.S. PATENT DOCUMENTS

| | | | |
|---|---|---|---|
| 3,897,902 | A | 8/1975 | Yanez, Jr. |
| 3,933,592 | A | 1/1976 | Clendenning |
| 3,971,703 | A | 7/1976 | Picciolo et al. |
| 4,144,134 | A | 3/1979 | Plakas |
| 4,184,483 | A * | 1/1980 | Greenspan ............. 600/572 |
| 4,303,752 | A | 12/1981 | Kolehmainen et al. |
| 4,421,848 | A | 12/1983 | Whitlock |
| 4,503,149 | A | 3/1985 | Boyd |
| 4,698,311 | A | 10/1987 | Hall et al. |
| 4,729,846 | A | 3/1988 | Matsui et al. |
| 4,906,565 | A | 3/1990 | Vossen |
| 4,978,504 | A * | 12/1990 | Nason ............. 422/411 |
| 5,238,812 | A | 8/1993 | Coulter et al. |
| 5,258,285 | A | 11/1993 | Aegidius |
| 5,264,184 | A | 11/1993 | Aysta et al. |
| 5,576,185 | A | 11/1996 | Coulter et al. |
| 5,595,653 | A | 1/1997 | Good et al. |
| 5,695,989 | A | 12/1997 | Kalamasz |
| 5,827,675 | A * | 10/1998 | Skiffington et al. ............. 435/8 |
| 5,891,702 | A | 4/1999 | Sakakibara et al. |
| 5,905,029 | A | 5/1999 | Andreotti et al. |
| 5,908,751 | A | 6/1999 | Higo et al. |
| 6,045,913 | A | 4/2000 | Castle |
| 6,140,040 | A | 10/2000 | Palm et al. |
| 6,174,704 | B1 | 1/2001 | Chu et al. |
| 6,200,767 | B1 | 3/2001 | Sakakibara et al. |
| 6,451,260 | B1 | 9/2002 | Düsterhöft et al. |
| 6,465,201 | B1 | 10/2002 | Presente et al. |
| 6,588,681 | B2 | 7/2003 | Rothrum et al. |
| 6,660,489 | B2 | 12/2003 | Schrecengost et al. |
| 6,699,987 | B2 * | 3/2004 | Hillebrand et al. ......... 536/25.4 |
| 6,824,560 | B2 | 11/2004 | Pelton |
| 6,861,067 | B2 | 3/2005 | McGhee et al. |
| 6,967,261 | B1 | 11/2005 | Soerens et al. |
| 7,005,143 | B2 | 2/2006 | Abuelyaman et al. |
| 7,045,913 | B2 | 5/2006 | Ebrahim et al. |
| 7,083,911 | B2 | 8/2006 | Wood et al. |
| 7,141,033 | B2 | 11/2006 | Kanjilal et al. |
| 7,282,181 | B2 | 10/2007 | Hudak et al. |
| 7,338,692 | B2 | 3/2008 | Smith et al. |
| 7,422,868 | B2 | 9/2008 | Fan et al. |
| 7,485,609 | B2 | 2/2009 | Reddy et al. |
| 7,553,417 | B2 | 6/2009 | Waller, Jr. et al. |
| 7,824,732 | B2 | 11/2010 | Sahouani et al. |
| 2003/0104507 | A1 | 6/2003 | Wood et al. |
| 2004/0124085 | A1 | 7/2004 | Tai et al. |
| 2004/0157971 | A1 | 8/2004 | Kim |
| 2004/0161788 | A1 | 8/2004 | Chen et al. |
| 2004/0197845 | A1 * | 10/2004 | Hassibi et al. ............. 435/8 |
| 2005/0048592 | A1 | 3/2005 | Wood et al. |
| 2005/0070701 | A1 | 3/2005 | Hochstetler et al. |
| 2005/0142571 | A1 | 6/2005 | Parthasarathy et al. |
| 2005/0152992 | A1 | 7/2005 | Johnson et al. |
| 2005/0153423 | A1 | 7/2005 | Baba et al. |
| 2005/0181467 | A1 | 8/2005 | Schrecengost et al. |
| 2005/0250138 | A1 | 11/2005 | Young et al. |
| 2005/0272111 | A1 * | 12/2005 | Bryan et al. ............. 435/8 |
| 2006/0062854 | A1 | 3/2006 | Chandra et al. |
| 2006/0166347 | A1 | 7/2006 | Faulstich et al. |
| 2006/0273049 | A1 | 12/2006 | Leach et al. |
| 2007/0148458 | A1 | 6/2007 | Sahouani et al. |
| 2007/0212266 | A1 | 9/2007 | Johnston et al. |
| 2007/0269341 | A1 | 11/2007 | Halverson et al. |
| 2008/0023408 | A1 | 1/2008 | Hansen |
| 2008/0064939 | A1 | 3/2008 | Reynolds et al. |
| 2008/0153125 | A1 | 6/2008 | Buttry et al. |
| 2008/0206740 | A1 * | 8/2008 | Skiffington et al. ............. 435/5 |
| 2008/0207794 | A1 | 8/2008 | Wright et al. |
| 2009/0068065 | A1 | 3/2009 | Pagoria et al. |
| 2010/0190171 | A1 | 7/2010 | Kshirsagar et al. |
| 2010/0209927 | A1 | 8/2010 | Menon et al. |
| 2010/0209961 | A1 | 8/2010 | Kshirsagar et al. |
| 2010/0248214 | A1 | 9/2010 | Kshirsagar et al. |

FOREIGN PATENT DOCUMENTS

| | | |
|---|---|---|
| EP | 1 661 988 | 5/2006 |
| EP | 1 845 375 | 10/2007 |
| GB | 2 138 021 | 10/1984 |
| GB | 2 433 219 | 6/2007 |
| JP | 06-245795 | 9/1994 |
| JP | 11-028099 | 2/1999 |
| JP | H11-514849 | 12/1999 |
| JP | 2005-012518 | 2/2005 |
| JP | 2005-098022 | 10/2005 |
| WO | WO 89/09279 | 10/1989 |
| WO | WO 96/07759 | 3/1996 |
| WO | WO 97/02812 | 1/1997 |
| WO | WO 97/03209 | 1/1997 |
| WO | WO 00/29112 | 5/2000 |
| WO | WO 2005/045075 | 5/2005 |
| WO | WO 2005071388 A1 * | 8/2005 |
| WO | WO 2005/094792 | 10/2005 |
| WO | WO 2007/113583 | 10/2007 |
| WO | WO 2007/137257 | 11/2007 |
| WO | WO 2007/146722 | 12/2007 |
| WO | WO 2008/075044 | 6/2008 |
| WO | WO 2008/122908 | 10/2008 |
| WO | WO 2008/129517 | 10/2008 |
| WO | WO 2008/134472 | 11/2008 |
| WO | WO 2008/150779 | 12/2008 |
| WO | WO 2009/009188 | 1/2009 |
| WO | WO 2009/046081 | 4/2009 |
| WO | WO 2009/046183 | 4/2009 |
| WO | WO 2009/046191 | 4/2009 |
| WO | WO 2009/048743 | 4/2009 |
| WO | WO 2009/061864 | 5/2009 |
| WO | WO 2009/067498 | 5/2009 |
| WO | WO 2009/067503 | 5/2009 |
| WO | WO 2009/067513 | 5/2009 |
| WO | WO 2009/067518 | 5/2009 |
| WO | WO 2009/076267 | 6/2009 |
| WO | WO 2009/082667 | 7/2009 |
| WO | WO 2009/085357 | 7/2009 |
| WO | WO 2009/102859 | 8/2009 |
| WO | WO 2009/137138 | 11/2009 |
| WO | WO 2009140356 A1 * | 11/2009 |
| WO | WO 2010/039627 | 4/2010 |
| WO | WO 2010/078399 | 7/2010 |
| WO | WO 2010/078404 | 7/2010 |
| WO | WO 2010/078482 | 7/2010 |
| WO | WO 2010/129726 | 11/2010 |
| WO | WO 2010/129727 | 11/2010 |
| WO | WO 2010/129728 | 11/2010 |
| WO | WO 2011/079038 | 6/2011 |

OTHER PUBLICATIONS

DeLuca, M. et al.; "Factors Affecting the Kinetics of Light Emission from Crude and Purified Firefly Luciferase"; Analytical Biochemistry; vol. 95; 1979; pp. 194-198.

Gorus, F. et al.; "Applications of Bio- and Chemiluminescence in the Clinical Laboratory"; Clinical Chemistry; vol. 25, No. 4; 1979; pp. 512-519.

Harvey, E.N. "A History of Luminescence—From the Earliest Times Until 1900"; American Philosophical Society, Philadelphia, PA 1957 (cover, copyright, and Table of Contents consisting of 12 pgs).

Lee JiYoung et al.; "Detection of *E. coli* in beach water within 1 hour using immunomagnetic separation and ATP bioluminescence"; Luminescence; vol. 19, No. 1; 2004; pp. 31-36.

McElroy, W.D. et al.; "Factors Influencing the Response of the

(56) References Cited

OTHER PUBLICATIONS

Bioluminescent Reaction to Adenosine Triphosphate"; Archives of Biochemistry; vol. 22; 1949; pp. 420-433.

Morbe, J.L. et al.; "Release of miniantibodies from *E. coli* cells into the supernatant at low and high cell densities": Micorbiol. Res.; vol. 152; No. 4; 1997; pp. 385-394.

Navrátil, M. et al.; "Chapter 34—Bioluminescence in Immobilized Cells for Biomass Detection and Biosensor Applications"; Methods in Biotechnology: Immobilization of Enzymes and Cells, Second Edition; vol. 22; 2006; pp. 393-401.

Oster, J., et al.; "Polyvinyl-alcohol-based magnetic beads for rapid and efficient separation of specific or unspecific nucleic acid sequences"; Journal of Magnetism and Magnetic Materials; vol. 225; 2001; pp. 145-150.

Stanley, P.E.; "[2] Extraction of Adenosine Triphosphate from Microbial and Somatic Cells"; Methods in Enzymology; vol. 133; Bioluminescence and Chemiluminescence Part B; 1986; pp. 14-22.

Abstract entitled "Waterborne Cryptosporidium parvum detection using the particle filtration system and quantitative PCR"; from General Meeting of the American Society for Microbiology; vol. 103; 2003; p. Q-096.

Abstract entitled "Use of fluorescent microspheres to evaluate the particle filtration system for waterborne pathogen detection"; from General Meeting of the American Society for Microbiology; vol. 103; 2003; pp. Q-268.

"Standard Methods for the Examination of Water and Wastewater," $20^{th}$ Edition; Edited by L. S. Clesceri et al.; American Public Health Association; 1998, Title, copyright and Table of Contents 23 pages.

"ATP test" from Wikipedia, the free encyclopedia. Printed on Feb. 25, 2013.

Cho, M. et al.; "A Bioluminescent Cytotoxicity Assay for Assessment of Membrane Integrity Using a Proteolytic Biomarker"; Toxicol In Vitro.; vol. 22, No. 4; 2008; pp. 1099-1106.

Crouch, S.P.M. et al.; "The use of ATP bioluminescence as a measure of cell proliferation and cytotoxicity"; Journal of Immunological Methods; vol. 160; 1993; pp. 81-88.

\* cited by examiner

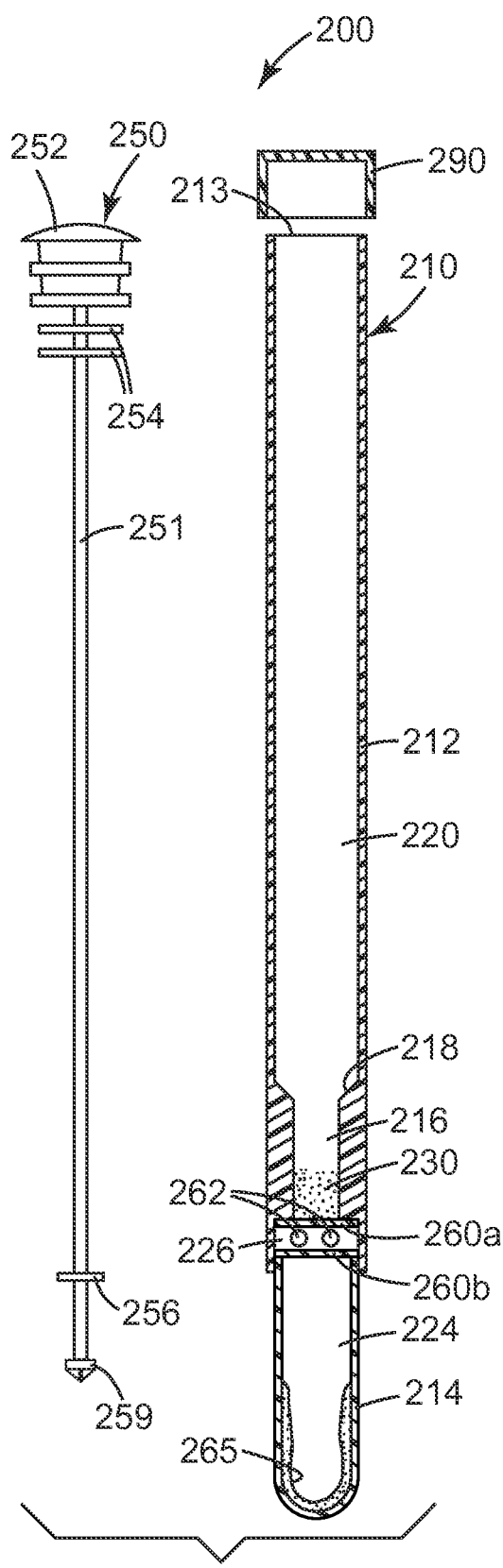
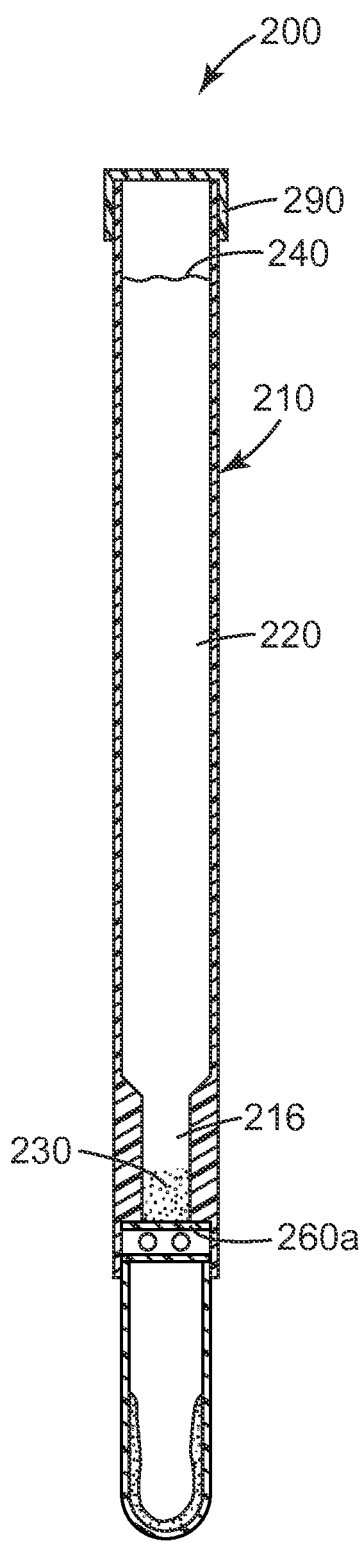
*Fig. 2A*
*Fig. 2B*

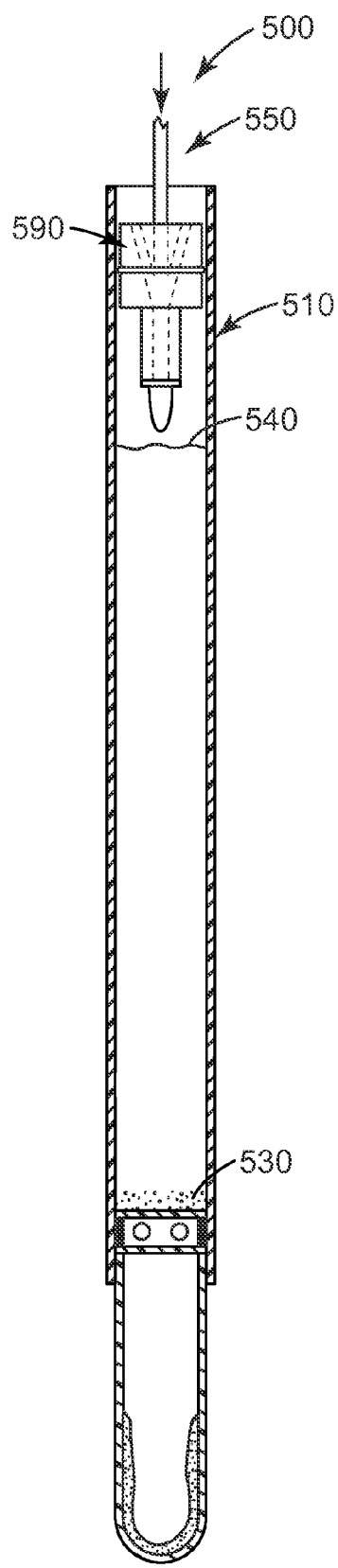
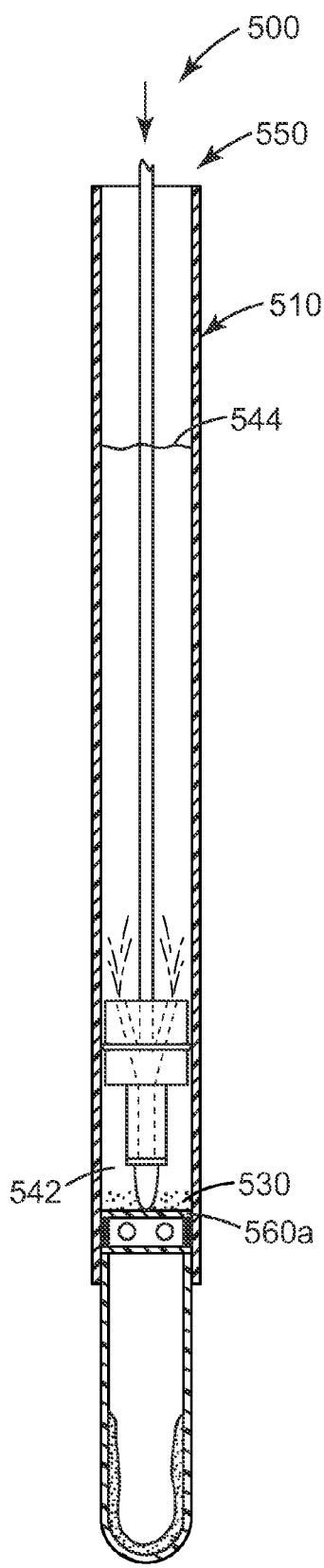
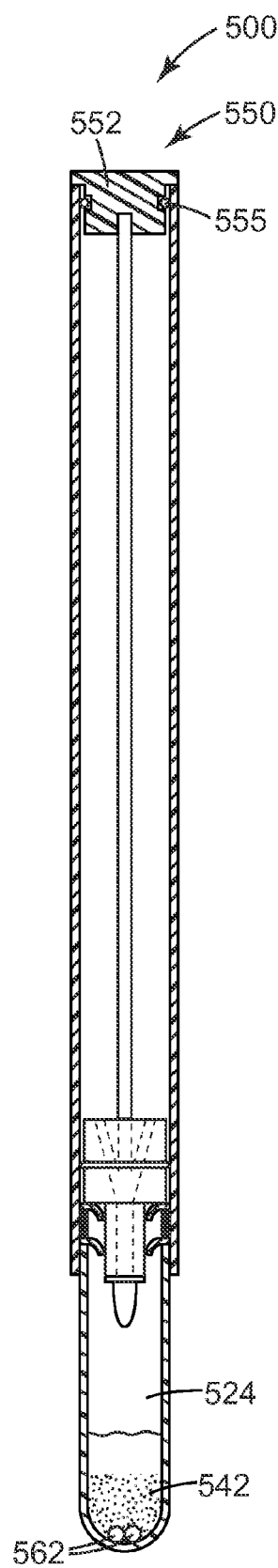
*Fig. 5B*  *Fig. 5C*  *Fig. 5D*

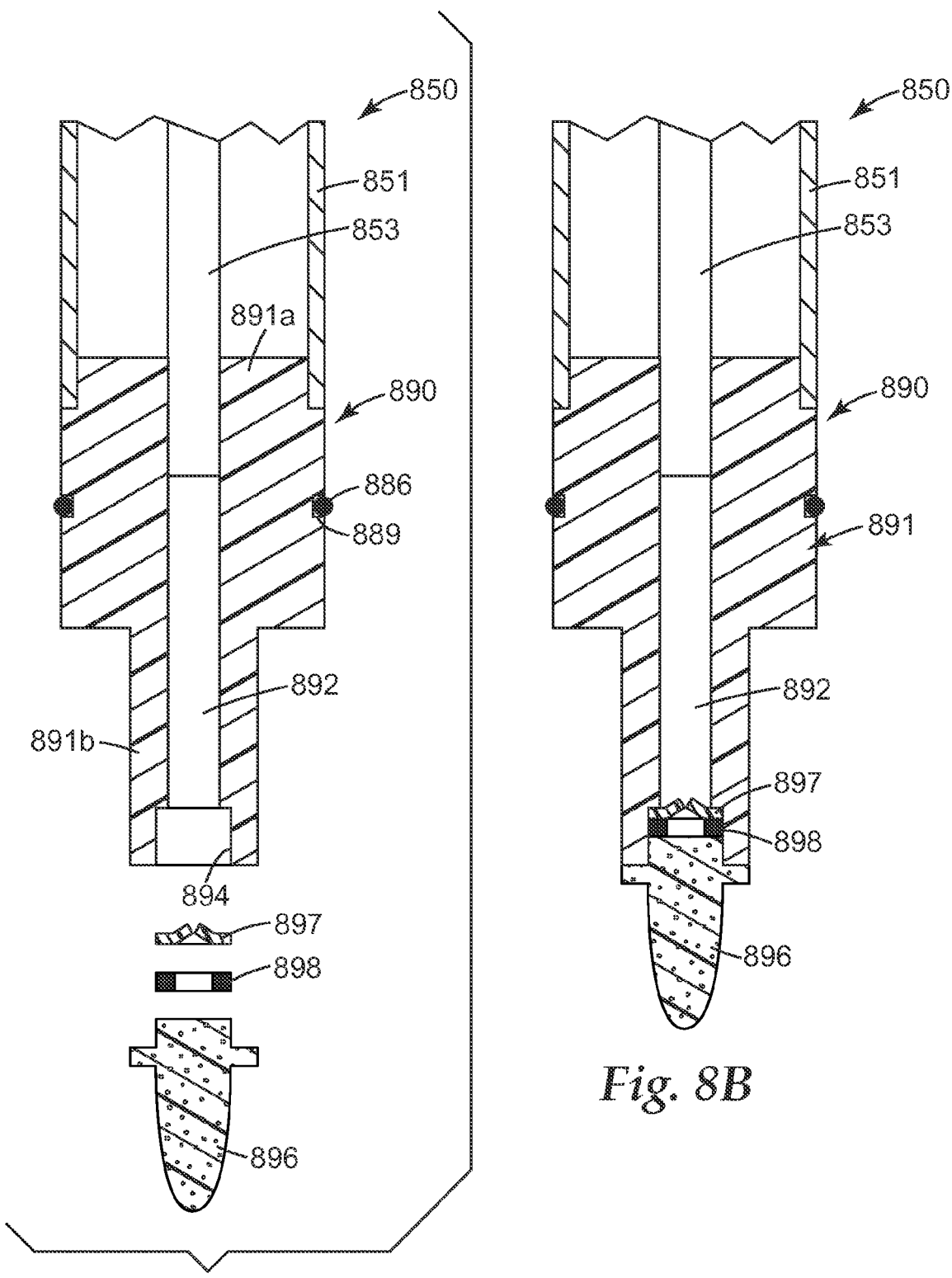

US 9,284,593 B2

LIVE BIOLOAD DETECTION USING MICROPARTICLES

CROSS REFERENCE TO RELATED APPLICATIONS

This application claims the benefit of U.S. Provisional Patent Application Nos. 61/291,301, filed Dec. 30, 2009 and 61/331,931, filed May 6, 2010, which are incorporated herein by reference in their entirety.

BACKGROUND

Various tests are available that can be used to assess the presence of biological analyte associated with a cell or a plurality of cells in a sample (e.g. surface, water, air, etc). Such tests include those based on the detection of ATP using the firefly luciferase reaction, tests based on the detection of protein using colorimetry, tests based on the detection of microorganisms using microbiological culture techniques, and tests based on detection of microorganisms using immunochemical techniques. Surfaces can be sampled using either a swab device or by direct contact with a culture device such as an agar plate. The sample can be analyzed for the presence of live cells and, in particular, live microorganisms.

Results from these tests are often used to make decisions about the cleanliness of a surface. For example, the test may be used to decide whether food-processing equipment has been cleaned well enough to use for production. Although the above tests are useful in the detection of a contaminated surface, they can require numerous steps to perform the test, they may not be able to distinguish quickly and/or easily the presence of live cells from dead cells and, in some cases, they can require long periods of time (e.g., hours or days) before the results can be determined.

The tests may be used to indicate the presence of live microorganisms. For such tests, a cell extractant is often used to release a biological analyte (e.g., ATP) associated with living cells. The presence of extracellular material (e.g., non-cellular ATP released into the environment from dead or stressed animal cells, plant cells, and/or microorganisms) can create a high "background" level of ATP that can complicate the detection of live cells.

In spite of the availability of a number of methods and devices to detect live cells, there remains a need for a simple, reliable test for detecting live cells and, in particular, live microbial cells.

SUMMARY OF THE INVENTION

In general, the present disclosure relates to articles and methods for detecting live cells in a sample. The articles and methods make possible the rapid detection (e.g., through fluorescence, chemiluminescence, or a color reaction) of the presence of cells such as bacteria on a surface. In some embodiments, the inventive articles are "sample-ready", i.e., the articles contain all of the necessary features to detect living cells in a sample. In some aspects, the inventive articles and methods provide a means to distinguish a biological analyte, such as ATP or an enzyme, that is associated with eukaryotic cells (e.g., plant or animal cells) from a similar or identical biological analyte associated with prokaryotic cells (e.g., bacterial cells). Furthermore, the inventive articles and methods provide a means to distinguish a biological analyte that is free in the environment (i.e., an a cellular biological analyte) from a similar or identical biological analyte associated with a living cell.

Methods of the present disclosure allow an operator to concentrate cells from a liquid sample and to detect an analyte associated with the cells. In certain embodiments, detection of the analyte may be an indicator of live cells including, in particular, live microbial cells in the sample. In some embodiments, the methods provide for the operator to measure the amount of a biological analyte and/or cells in the sample. In some embodiments, the methods provide for the operator to, after a predetermined period of time during which an effective amount of a cell extractant is released from a composition into the liquid mixture, measure the amount of a biological analyte to determine differentially the amount of biological analyte from acellular material and from live cells in the sample. In some embodiments, the methods provide for the operator, within a first predetermined period of time, to perform a first measurement of the amount of a biological analyte and, within a second predetermined period of time during which an effective amount of cell extractant is released from the composition, perform a second measurement of the amount of biological analyte to detect the presence of live cells in the sample. In some embodiments, the methods can allow the operator to distinguish whether biological analyte in the sample was released from live plant or animal cells or whether it was released from live microbial cells (e.g., bacteria). The present invention is capable of use by operators under the relatively harsh field environment of institutional food preparation services, health care environments and the like.

In one aspect, the present disclosure provides a method of detecting cells in a sample. The method can comprise providing a cell concentration agent, a release element comprising a cell extractant and a liquid sample. The method further can comprise contacting the liquid sample and the cell concentration agent for a period of time, isolating the cell concentration agent from at least a portion of the liquid sample, forming a liquid mixture comprising the isolated cell concentration agent and the release element wherein the cell extractant is released into the mixture, and detecting a biological analyte from the cells. Optionally, the analyte can be detected at two or more discrete time points. In some embodiments, detecting a biological analyte can comprise detecting a live cell. In some embodiments, detecting a biological analyte can comprise using a detection system. In some embodiments, detecting a biological analyte can comprise quantifying the analyte. In some embodiments, detecting a biological analyte can comprise detecting ATP from a cell. In some embodiments, detecting a biological analyte can comprise detecting the cell by genetic or immunological methods. In some embodiments, the method further can comprise the steps of providing a somatic cell extractant and contacting the somatic cell extractant with cells from the sample.

In another aspect, the present disclosure provides a method of detecting cells in a sample. The method can comprise providing a sample; a cell concentration agent; a release element comprising a cell extractant; a detection article comprising a housing with first and second receptacles and an opening configured to receive the sample; means for isolating and transferring the cell concentration agent from a first receptacle to a second receptacle in the housing. The method further can comprise contacting the sample and the cell concentration agent in a liquid medium the in the first receptacle of the housing. The method further can comprise transferring the cell concentration agent to the second receptacle in the housing. The method further can comprise forming a liquid mixture comprising the isolated cell concentration agent and the release element, wherein the cell extractant is released into the mixture. The method further can comprise detecting a biological analyte from the cells. Optionally, the biological analyte can be detected at two or more discrete time points. In some embodiments, detecting a biological analyte can comprise detecting a live cell. In some embodiments, detecting a biological analyte can comprise using a detection system. In some embodiments, detecting a biological analyte can comprise quantifying the analyte. In some embodiments, detecting a biological analyte can comprise detecting ATP from a cell. In some embodiments, detecting a biological analyte can comprise detecting the cell by genetic or immunological methods. In some embodiments, the method further can comprise the steps of providing a somatic cell extractant and contacting the somatic cell extractant with cells from the sample.

In another aspect, the present disclosure provides a method of detecting cells in a sample. The method can comprise providing a sample; a detection article comprising a housing with an opening configured to receive the sample, a first receptacle containing a cell concentration agent, and a second receptacle containing a release element comprising a cell extractant; means for isolating the cell concentration agent from at least a portion of the liquid sample; and means for transferring the cell concentration agent from the first receptacle to the second receptacle in the housing. The method further can comprise contacting the sample and the cell concentration agent in a liquid medium in the first receptacle of the housing. The method further can comprise isolating and transferring the cell concentration agent to the second receptacle of the housing. The method further can comprise forming a liquid mixture comprising the isolated cell concentration agent and the release element, wherein the cell extractant is released into the mixture. The method further can comprise detecting a biological analyte from the cells. Optionally, the biological analyte can be detected at two or more discrete time points. In some embodiments, detecting a biological analyte can comprise detecting a live cell. In some embodiments, detecting a biological analyte can comprise using a detection system. In some embodiments, detecting a biological analyte can comprise quantifying the analyte. In some embodiments, detecting a biological analyte can comprise detecting ATP from a cell. In some embodiments, detecting a biological analyte can comprise detecting the cell by genetic or immunological methods. In some embodiments, the method further can comprise the steps of providing a somatic cell extractant and contacting the somatic cell extractant with cells from the sample.

In another aspect, the present disclosure provides a unitary sample preparation and detection device. The device can comprise a housing comprising first and second receptacles with a passageway there between. The first receptacle of the housing can comprise an opening configured to receive a sample and a cell concentration agent disposed therein. The second receptacle of the housing can comprise a detection reagent disposed therein. The device further can comprise means for isolating the first receptacle from the second receptacle. The device further can comprise means for transferring the cell concentration agent from the first receptacle to the second receptacle. In some embodiments, the means for isolating the first and second receptacles is the means for transferring the cell concentration agent from the first receptacle to the second receptacle. In some embodiments, the housing further can comprise a frangible seal between the isolated first and second receptacles. In some embodiments, the first receptacle can comprise a taper region. In some embodiments, the device further can comprise a release element comprising a cell extractant. In some embodiments, the housing further can comprise a third receptacle. In some embodiments, the device further can comprise a sample acquisition device. In some embodiments, the detection reagent can comprise a reagent for detecting ATP. In some embodiments, the device further can comprise a release element comprising a detection reagent.

In another aspect, the present disclosure provides a unitary sample preparation and detection device. The device can comprise a housing comprising isolated first and second receptacles with a passageway there between and a piston configured to fit the passageway. The first receptacle in the housing can comprise an opening configured to receive a sample and a cell concentration agent disposed therein. The second receptacle of the housing can comprise a detection reagent disposed therein. In some embodiments, the housing further can comprise a frangible seal between the isolated first and second receptacles. In some embodiments, the first receptacle can comprise a tapered inner wall. In some embodiments, the device further can comprise a release element comprising a cell extractant. In some embodiments, the housing further can comprise a third isolated receptacle. In some embodiments, the device further can comprise a sample acquisition device. In some embodiments, the detection reagent can comprise a reagent for detecting ATP. In some embodiments, the device further can comprise a slow-release composition comprising a detection reagent.

In another aspect, the present disclosure provides a unitary sample preparation and detection device. The device can comprise a housing comprising isolated first and second receptacles with a passageway there between. The first receptacle of the housing can comprise an opening configured to receive a sample and a cell concentration agent disposed therein. The second receptacle can comprise a detection reagent disposed therein. The device further can comprise a valve configured to control the passage of material from the first receptacle to the second receptacle. In some embodiments, the first receptacle can comprise a tapered inner wall. In some embodiments, the device further can comprise a release element comprising a cell extractant. In some embodiments, the housing further can comprise a third isolated receptacle. In some embodiments, the device further can comprise a sample acquisition device. In some embodiments, the detection reagent can comprise a reagent for detecting ATP. In some embodiments, the device further can comprise a slow-release composition comprising a detection reagent.

In another aspect, the present disclosure provides a kit comprising a housing comprising isolated first and second receptacles with a passageway there between and means for transferring the cell concentration agent from the first receptacle to the second receptacle. The first receptacle of the housing can comprise an opening configured to receive a sample. The second receptacle can comprise a detection reagent disposed therein. The kit further can comprise a cell concentration agent. In some embodiments, the cell concentration agent is disposed in the first receptacle of the housing. In some embodiments, the kit further can comprise release element comprising a microbial cell extractant. In some embodiments, the kit further can comprise a somatic cell extractant. In some embodiments, the kit further can comprise a sample acquisition device.

In another aspect, the present disclosure provides a kit comprising a housing comprising isolated first and second receptacles with a passageway there between. The first receptacle in the housing can comprise an opening configured to receive a sample. The second receptacle in the housing can comprise a detection reagent disposed therein. The kit further can comprise a cell concentration agent and means for transferring the cell concentration agent from the first receptacle to the second receptacle. In some embodiments, the cell concentration agent is disposed in the first receptacle of the housing. In some embodiments, the kit further can comprise release element comprising a microbial cell extractant. In some embodiments, the kit further can comprise a somatic cell extractant. In some embodiments, the kit further can comprise a sample acquisition device.

GLOSSARY

"Biological analytes", as used herein, refers to molecules, or derivatives thereof, that occur in or are formed by an organism. For example, a biological analyte can include, but is not limited to, at least one of an amino acid, a nucleic acid, a polypeptide, a protein, a nucleotide, a polynucleotide, a lipid, a phospholipid, a saccharide, a polysaccharide, and combinations thereof. Specific examples of biological analytes can include, but are not limited to, a metabolite (e.g., a small molecule, such as ATP, or a polypeptide, such as protein A), an allergen (e.g., peanut allergen(s), a hormone, a toxin (e.g., *Bacillus* diarrheal toxin, aflatoxin, etc.), RNA (e.g., mRNA, total RNA, tRNA, etc.), DNA (e.g., plasmid DNA, plant DNA, etc.), a tagged protein, an antibody, an antigen, and combinations thereof.

"Liquid sample", as used herein, refers to a sample material that comprises a liquid. The sample may, in its original form, comprise a liquid such as, for example, water, milk, juice, blood, wound exudate, and the like. Alternatively, the liquid sample can be a suspension of solids in a liquid suspending medium (e.g., water, an aqueous buffer). For example, a solid, semisolid, or gelatinous sample can be collected with a sample acquisition device and suspended in a liquid to form a liquid sample.

"Clarified liquid sample" refers to the bulk of a liquid sample that remains after the liquid sample has been contacted with a cell concentration agent and the cell concentration agent has been partitioned (e.g., by sedimentation, filtration, centrifugation, or precipitation) from the bulk of the liquid.

"Sample acquisition device" is used herein in the broadest sense and refers to an implement used to collect a liquid, semisolid, or solid sample material. Nonlimiting examples of sample acquisition devices include swabs, wipes, sponges, scoops, spatulas, pipettes, pipette tips, and siphon hoses.

"Dead-end valve", as used herein, refers to a type of valve that is used to regulate the transfer of material (e.g., liquids, solids, or a suspension of solids in a liquid) between two or more receptacles in the housing of a detection device. The dead-end valve is designed such that the cavity in the valve that is used to transfer the material can only be in fluid communication with one of the receptacles at a time.

As used herein, the term "hydrogel" refers to a polymeric material that is hydrophilic and that is either swollen or capable of being swollen with a polar solvent. The polymeric material typically swells but does not dissolve when contacted with the polar solvent. That is, the hydrogel is insoluble in the polar solvent. The swollen hydrogel can be dried to remove at least some of the polar solvent.

"Cell extractant", as used herein, refers to any compound or combination of compounds that alters cell membrane or cell wall permeability or disrupts the integrity of (i.e., lyses or causes the formation of pores in) the membrane and/or cell wall of a cell (e.g., a somatic cell or a microbial cell) to effect extraction or release of a biological analyte normally found in living cells.

"Detection system", as used herein, refers to the components used to detect a biological analyte and includes enzymes, enzyme substrates, binding partners (e.g. antibodies or receptors), labels, dyes, and instruments for detecting light absorbance or reflectance, fluorescence, and/or luminescence (e.g. bioluminescence or chemiluminescence).

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a housing that comprises "a" detection reagent can be interpreted to mean that the housing can include "one or more" detection reagents.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2A shows a cross-sectional view of one embodiment of a housing comprising three receptacles separated by frangible seals and a side view of a plunger adapted for use with the housing, which are both components of a sample preparation and detection device according to the present disclosure.

FIG. 2B shows a cross-sectional view of the housing of FIG. 2A with a cap secured thereon and with a liquid sample disposed in a first receptacle of the housing.

FIG. 5B-5D show a cross-sectional views of the assembled device of FIG. 5A with the plunger inserted to various depths into the housing.

FIG. 8A shows an exploded side view, partially in section, of the tip of the plunger of FIG. 7A.

FIG. 8B shows a side view, partially in section, of the assembled tip of FIG. 8A.

FIG. 12b is a cross-sectional view of the release element of FIG. 12a.

DETAILED DESCRIPTION

Figures 1A, 1B, 1C, 1D:
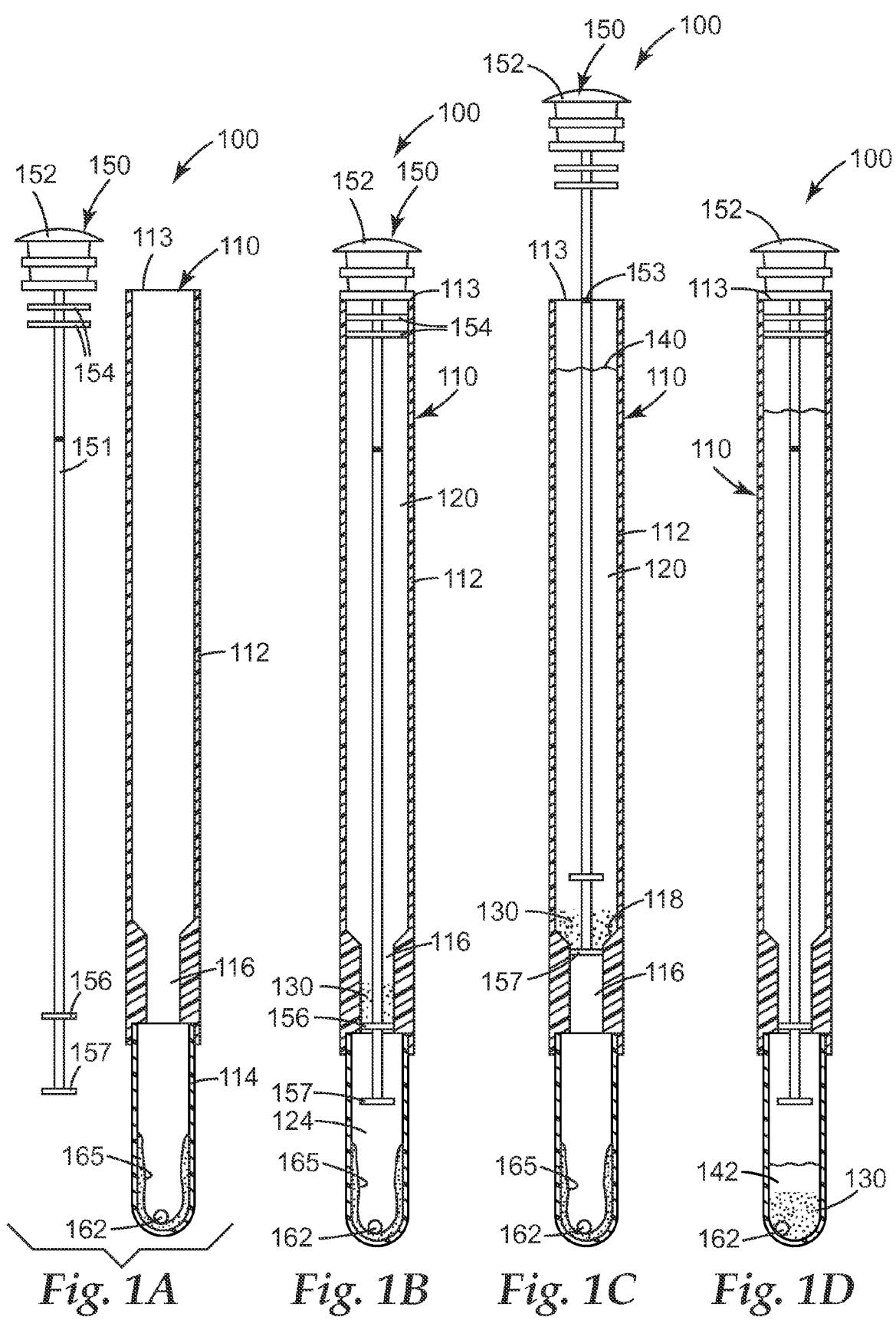
FIG. 1A shows a cross-sectional view of one embodiment of a housing comprising two receptacles and a cross-sectional view of a plunger adapted for use with the housing, which are both components of a sample preparation and detection device according to the present disclosure.
FIG. 1B shows a cross-sectional view of the assembled device of FIG. 1A with the plunger disposed in the housing in a first position and including a cell concentration agent in a first receptacle of the housing.
FIG. 1C shows a cross-sectional view of the device of FIG. 1B with the plunger disposed in the housing in a second position and including a liquid sample in the first receptacle of the housing.
FIG. 1D shows a cross-sectional view of the device of FIG. 1C with the plunger in the first position and the cell concentration agent in a second receptacle of the housing.

All patents, patent applications, government publications, government regulations, and literature references cited in this specification are hereby incorporated herein by reference in their entirety. In case of conflict, the present description, including definitions, will control.

The present invention generally relates to articles and methods for detecting microorganisms in a sample. In certain preferred embodiments, the present invention relates to the detection of live microorganisms in a sample. Methods and devices for the concentration of cells from a sample are described in PCT International Publication No. WO 2010/078399 entitled "SAMPLING DEVICES AND METHODS FOR CONCENTRATING MICROORGANISMS" and PCT International Publication No. WO 2010/078404 entitled "METHODS, KITS AND SYSTEMS FOR PROCESSING SAMPLES", each incorporated herein by reference in its entirety. The inventive devices and methods disclosed herein provide increased sensitivity to detect small numbers of microorganisms present in a sample.

Biological analytes can be used to detect the presence of biological material, such as live cells in a sample. Biological analytes can be detected by various reactions (e.g., binding reactions, catalytic reactions, and the like) in which they can participate.

Chemiluminescent reactions can be used in various forms to detect cells, such as bacterial cells, in fluids and in processed materials. In some embodiments of the present disclosure, a chemiluminescent reaction based on the reaction of adenosine triphosphate (ATP) with luciferin in the presence of the enzyme luciferase to produce light provides the chemical basis for the generation of a signal to detect a biological analyte, ATP. Since ATP is present in all living cells, including all microbial cells, this method can provide a rapid assay to obtain a quantitative or semiquantitative estimate of the number of living cells in a sample. Early discourses on the nature of the underlying reaction, the history of its discovery, and its general area of applicability, are provided by E. N. Harvey (1957), A History of Luminescence: From the Earliest Times Until 1900, Amer. Phil. Soc., Philadelphia, Pa.; and W. D. McElroy and B. L. Strehler (1949), *Arch. Biochem. Biophys.* 22:420-433.

ATP detection is a reliable means to detect bacteria and other microbial species because all such species contain some ATP. Chemical bond energy from ATP is utilized in the bioluminescent reaction that occurs in the tails of the firefly *Photinus pyralis*. The biochemical components of this reaction can be isolated free of ATP and subsequently used to detect ATP in other sources. The mechanism of this firefly bioluminescence reaction has been well characterized (DeLuca, M., et al., 1979 *Anal. Biochem.* 95:194-198).

Release Element:

Release elements, according to the present disclosure, include encapsulating materials. Encapsulating materials generally act as a physical barrier and/or a diffusion barrier to prevent the immediate dissolution, for a period of time, of an effective amount of cell extractant into a liquid mixture (for example, an aqueous mixture comprising a sample).

In some embodiments, the encapsulating materials may be activated to release an effective amount of cell extractant after the encapsulant is exposed to an activating stimulus. Activation may include, for example, dissolution or partial dissolution of the encapsulating material, permeabilization (e.g., by swelling a partially dehydrated polymer) of the encapsulating material, disintegration or partial disintegration of the encapsulating material (e.g., by melting a solid material such as, for example a wax).

In some embodiments, encapsulating material can comprise a shell structure (e.g., a chromonic material), as described herein.

In some embodiments, the encapsulating material can comprise a matrix. Examples of suitable matrix materials can be found, for example, in PCT International Publication No. WO 2010/129726 and entitled, "ARTICLES WITH MATRIX COMPRISING A CELL EXTRACTANT AND BIODETECTION METHODS THEREOF", which is incorporated herein by reference in its entirety. In some embodiments, the matrix comprises a material (e.g., a polymeric material or a nonpolymer material such as a ceramic) that is substantially insoluble in a liquid (for example, an aqueous liquid comprising a sample). In some embodiments, the matrix comprises an excipient that is substantially soluble and/or dispersible at ambient temperature in an aqueous solution. In some embodiments, the matrix comprises an excipient that is substantially insoluble and nondispersible at ambient temperature in an aqueous solution (i.e., the dissolution or dispersion of the excipient can be triggered by a temperature shift and/or the addition of a chemical trigger).

In some embodiments, the matrixes can be pre-formed matrixes (i.e., matrixes that are formed before the matrixes are infused with a cell extractant). In these embodiments, a cell extractant can be loaded into a matrix by placing the matrix into a liquid containing the cell extractant and allowing the cell extractant to diffuse into the matrix material. In some embodiments, matrix precursors can be mixed in a solution with the cell extractant and the matrix is formed with the cell extractant dispersed within the matrix. In another embodiment, the cell extractant can be dispersed in wax, as described, for example, in U.S. Patent Application Publication No. US2005/0152992, which is incorporated herein by reference in its entirety.

Encapsulating materials can comprise a hydrogel. The use of hydrogels in articles and methods for detecting cells in a sample is disclosed in PCT International Publication No. WO 2010/039627 and U.S. Application Ser. No. 61/101,563, filed on Sep. 30, 2008 and respectively entitled BIODETECTION ARTICLES and BIODETECTION METHODS, each of which is incorporated herein by reference in its entirety.

Hydrogels broadly include crosslinked hydrogels, swollen hydrogels, and dried or partially-dried hydrogels. Suitable hydrogels of the present disclosure include, for example, the hydrogels, and polymeric beads made there from, described in International Patent Publication No. WO 2007/146722, which is incorporated herein by reference in its entirety.

Other suitable hydrogels include polymers comprising ethylenically unsaturated carboxyl-containing monomers and comonomers selected from carboxylic acids, vinyl sulfonic acid, cellulosic monomer, polyvinyl alcohol, as described in U.S. Patent Application Publication No. US2004/0157971; polymers comprising starch, cellulose, polyvinyl alcohol, polyethylene oxide, polypropylene glycol, and copolymers thereof, as described in U.S. Patent Application Publication No. US 2006/0062854; polymers comprising multifunctional poly(alkylene oxide) free-radically polymerizable macromonomer with molecular weights less than 2000 daltons, as described in U.S. Pat. No. 7,005,143; polymers comprising silane-functionalized polyethylene oxide that cross-link upon exposure to a liquid medium, as described in U.S. Pat. No. 6,967,261; polymers comprising polyurethane prepolymer with at least one alcohol selected from polyethylene glycol, polypropylene glycol, and propylene glycol, as described in U.S. Pat. No. 6,861,067; and polymers comprising a hydrophilic polymer selected from polysaccharide, polyvinylpyrolidone, polyvinyl alcohol, polyvinyl ether, polyurethane, polyacrylate, polyacrylamide, collagen and gelatin, as described in U.S. Pat. No. 6,669,981, the disclosures of which are all herein incorporated by reference in their entirety. Other suitable hydrogels include agar, agarose, polyacrylamide hydrogels, and derivatives thereof.

The present disclosure provides for articles and methods that include a shaped hydrogel. Shaped hydrogels include hydrogels shaped into, for example, beads, sheets, ribbons, and fibers. Additional examples of shaped hydrogels and exemplary processes by which shaped hydrogels can be produced are disclosed in U.S. Patent Application Publication No. 2008/0207794 A1, entitled POLYMERIC FIBERS AND METHODS OF MAKING and U.S. Patent Application Publication No. US 2010/0295219, entitled METHODS OF MAKING SHAPED POLYMERIC MATERIALS, both of which are incorporated herein by reference in their entirety.

Hydrogels of the present disclosure can comprise a cell extractant. Hydrogels comprising a cell extractant can be made by two fundamental processes. In a first process, the cell extractant is incorporated into the hydrogel during the synthesis of the hydrogel polymer. Examples of the first process can be found in International Patent Publication No. WO 2007/146722. In a second process the cell extractant is incorporated into the hydrogel after the synthesis of the hydrogel polymer. For example, the hydrogel is placed in a solution of cell extractant and the cell extractant is allowed to absorb into and/or adsorb to the hydrogel. A further example of the second process is the incorporation of an ionic monomer into the hydrogel, such as the incorporation of a cationic monomer into the hydrogel.

In some applications, it may be desirable that the release element containing a cell extractant is in a dry or partially-dried state. Certain release elements (e.g., water-swollen hydrogels) can be dried, for example, by methods known to those skilled in the art, including evaporative processes, drying in convection ovens, microwave ovens, and vacuum ovens as well as freeze-drying. When the dried or partially-dried release element is exposed to a liquid or aqueous solution, the cell extractant can diffuse from the release element. The cell extractant can remain essentially dormant in the release element until exposed to a liquid or aqueous solution. That is, the cell extractant can be stored within the dry or partially-dried release element until the release element is exposed to a liquid. This can prevent the waste or loss of the cell extractant when not needed and can improve the stability of many moisture sensitive cell extractants that may degrade by hydrolysis, oxidation, or other mechanisms.

In some embodiments, the encapsulating materials may be activated to release an effective amount of cell extractant after the encapsulant is exposed to an activating stimulus such as pressure, shear, heat, light, pH change, exposure to another chemical, ionic strength change and the like. Activation may result in, for example, dissolution or partial dissolution of the encapsulating material, permeabilization of the encapsulating material (e.g. disruption of a lipid bilayer), and/or disintegration or partial disintegration of the encapsulating material (e.g., by fracturing or melting a solid material such as, for example microcrystalline wax).

Release elements, according to the present disclosure, include tablets that encapsulate the cell extractant. Tablets to delay the release of pharmaceutical compositions are known in the art (for example, see International Patent Publication Nos. WO 97/02812 and WO 08/129,517). "Tablets" is used broadly and includes microtablets, as disclosed in U.S. Patent Application Publication No. US2010/0209927 and entitled PROCESSING DEVICE TABLET, which is incorporated herein by reference in its entirety.

Tablets, according to the present disclosure, comprise a cell extractant admixed with an excipient. "Excipient" is used broadly to include, for example, binders, glidants (e.g., flow aids), lubricants, disintegrants, and any two or more of the foregoing. In some embodiments, tablets can comprise an outer coating, which may influence the release of an active substance (e.g., a cell extractant) when the tablet is contacted with a liquid (e.g., an aqueous liquid comprising a sample). In some embodiments, tablets can comprise fillers (e.g., a sugar such as lactose or sorbitol) as a bulking agent for the tablet. Disintegrants (e.g., a polysaccharide such as starch or cellulose) may promote wetting and/or swelling of the tablet and thereby facilitate release of the active substance when the tablet is contacted with a liquid. Sorbitol and mannitol are excipients that can promote the stability of certain cell extractants (e.g., enzymes). Mannitol can be used to delay the release of the cell extractant. In some embodiments, polyethylene glycol (PEG) is a preferred excipient to control the release of active substances from a tablet. In some embodiments, PEG compounds with molecular weights of 3300 and 8000 daltons can be used to delay the release of an active substance from a tablet.

Methods of making tablets are known in the art and include, for example, direct compression, wet granulation, dry granulation, and fluidized bed granulation.

Release elements, according to the present disclosure, include wax matrixes that encapsulate a cell extractant. In some embodiments, a plurality of bodies of cell extractant can be dispersed in a wax matrix. As the wax disintegrates (e.g., by thermal melting or mechanical disruption), the cell extractant is released from the wax. Nonlimiting examples of suitable waxes include natural or synthetic waxes or wax analogs, including paraffin wax, montan wax, carnuba wax, beeswax, scale wax, ozokerite, Utah wax, microcrystalline wax such as plastic and tank bottom derived microcrystalline waxes, wax substitutes such as Fischer-Tropsch wax, polyaklylenes such as polyethylene, polypropylene, blends and copolymers thereof.

In some embodiments, the cell extractant can be dispersed in the wax as droplets of a solution (e.g., an aqueous solution) that is immiscible with the wax. In some embodiments, the cell extractant can be dispersed in the wax as solid or semi-solid particles or agglomerates. Methods of making such dispersions of liquids or solids in wax are well known in the art.

Figure 11:
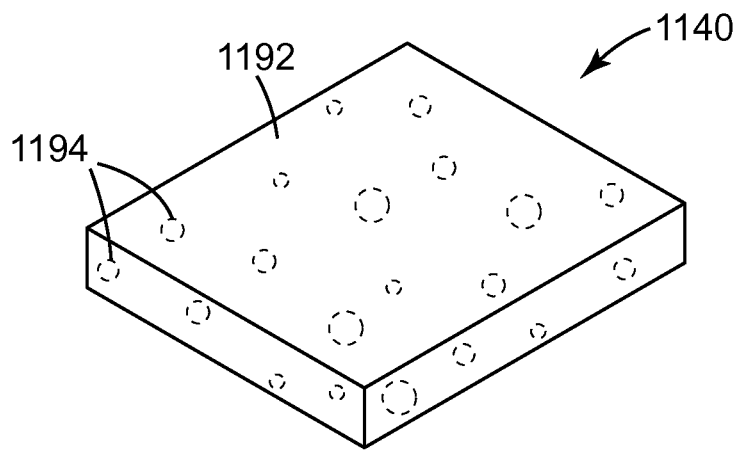
FIG. 11 shows a top perspective view of one embodiment of a release element with a cell extractant dispersed therein.

FIG. 11 shows a perspective view of one embodiment of a release element 1140 comprising a matrix material 1192. In the illustrated embodiment, the matrix material 1192 comprises a film or block of wax. Dispersed in the matrix material 1192 are cavities 1194 comprising a cell extractant. It is recognized that the amount and/or concentration of cell extractant dispersed in the release element 1140 and the shape and dimensions of the release element 1140 can be modified for use within a given detection article.

Release elements, according to the present invention, include substrates coated with a matrix material comprising a cell extractant. Release elements comprising a coated substrate with a cell extractant are disclosed in PCT International Publication No. WO 2010/129727 and entitled COATED SUBSTRATES COMPRISING A CELL EXTRACTANT AND BIODETECTION METHODS THEREOF, which is incorporated herein by reference in its entirety. The matrix material can be any suitable matrix material as described herein.

Matrix materials can be coated onto a substrate using coating processes that are known in the art such as, for example, dip coating, knife coating, curtain coating, spraying, kiss coating, gravure coating, offset gravure coating, and/or printing methods such as screen printing and inkjet printing. In some embodiments, the coating can be applied in a predetermined pattern. The choice of the coating process will be influenced by the shape and dimensions of the solid substrate and it is within the grasp of a person of ordinary skill in the appropriate art to recognize the suitable process for coating any given solid substrate.

In some embodiments, matrix material is coated onto the substrate as a pre-formed matrix (e.g., a polymer matrix) comprising a cell extractant. In some embodiments, a mixture comprising matrix precursors and cell extractant are coated onto the substrate and the matrix is formed on the substrate using, for example, polymerization processes known in the art and/or described herein. In some embodiments, a pre-formed matrix is coated onto the substrate or a matrix is formed on the substrate and, subsequently, the cell extractant is loaded into the substrate using processes known in the art and/or described herein.

In some embodiments, the coating mixture comprises an additive (e.g., a binder or viscosifier) to facilitate the coating process and/or to facilitate the adherence of the matrix material to the substrate. Non-limiting examples of additives include gums (e.g., guar gum, xanthan gum, alginates, carrageenan, pectin, agar, gellan, agarose), polysaccharides (e.g., starch, methylcellulose, carboxymethylcellulose, hydroxypropylmethylcellulose), and polypeptides (e.g., gelatin,).

Coating additives should be selected for their compatibility with the detection system used to detect cells in a sample. This compatibility can be tested by combining the additive with the detection system (e.g., luciferase and luciferin) and the analyte to be detected (e.g., ATP), measuring the response, and determining whether the additive substantially inhibits the detection of the analyte, as described herein.

The substrate onto which the matrix material is coated includes a variety of solid substrates. Nonlimiting examples of suitable substrate materials onto which matrixes comprising a cell extractant can be coated include plastic (e.g., polycarbonate, polyalkylenes such as polyethylene and polypropylene, polyesters, polyacrylates, and derivatives and blends thereof), metals (e.g., gold, graphite, platinum, palladium, nickel), glass, cellulose and cellulose derivatives (e.g., filter papers), ceramic materials, open-cell foams (e.g., polyurethane foam), nonwoven materials (e.g., membranes, PTFE membranes), and combinations thereof (e.g., a plastic-coated metal foil). The substrate can be configured in a variety of forms including, for example, fibers, nonwoven materials (e.g. nonwoven materials made from fibrous material comprising cellulose, glass, polyester, polyalkylene, polystyrene, and derivatives or combinations thereof), particles (e.g., beads), sheets, films, and membranes.

In some embodiments, the substrate can be a filter, such as Grade 4, 20-25 µm Qualitative Filter Paper, Grade 30, Glass-Fiber Filter Paper, Grade GB005, a thick (1.5 mm) highly absorbent blotting paper (all obtained from Whatman, Inc, Florham Park, N.J.), Zeta Plus Virosorb 1MDS discs (CUNO, Inc, Meriden, Conn.) and 0.45 µm MF-Millipore membrane (Millipore, Billerica, Mass.). Any one of the above substrates can be loaded a cell extractant solution containing polyvinyl alcohol. Any one of the above substrates can be loaded a cell extractant solution containing VANTOCIL (Arch Chemicals, Norwalk, Conn.). Any one of the above substrates can be loaded a cell extractant solution containing CARBOSHIELD (Lonza, Walkersville, Md.). Any one of the above substrates can be loaded a cell extractant solution containing 5% benzalkonium chloride solution.

Matrix materials, cell extractants, and substrates should be selected for their compatibility with the detection system used to detect cells in a sample. This compatibility can be tested by 1) detecting an amount of analyte in a detection system (e.g., a combining ATP with luciferin and luciferase and measuring the amount of luminescence with a luminometer, as described herein); 2) repeating the detection step with the matrix material, cell extractant, or substrate; and 3) comparing the results of step 1 with the results of step 2 to determine whether the matrix material, cell extractant, or substrate substantially inhibits the detection and/or measurement of the analyte in the reaction.

In some embodiments, release elements comprise coated substrates. The coating, the substrate and/or the coated substrate is adapted to act as a physical barrier and/or a diffusion barrier to prevent the immediate dissolution, for a brief period of time, of an effective amount of cell extractant into an aqueous mixture.

Coated substrates include a coating and a substrate. The coating comprises a cell extractant. The coating can be applied to the substrate using coating processes that are known in the art such as, for example, dip coating, knife coating, curtain coating, spraying, kiss coating, gravure coating, offset gravure coating, and/or printing methods such as screen printing and inkjet printing. In some embodiments, the coating can be applied in a pre-determined pattern (e.g., stripes, grids, spots). The choice of the coating process will be influenced by the shape and dimensions of the solid substrate and it is within the grasp of a person of ordinary skill in the appropriate art to recognize the suitable process for coating any given solid substrate.

The substrate onto which the coating is applied includes a variety of substrate materials. Nonlimiting examples of suitable substrate materials onto which a coating of the present disclosure can be applied include plastic (e.g., polycarbonate, polyalkylenes such as polyethylene and polypropylene, polyesters, polyacrylates, and derivatives and blends thereof), metals (e.g., gold, graphite, platinum, palladium, and nickel), glass, cellulose and cellulose derivatives (e.g., filter papers), ceramic materials, open-cell foams (e.g., polyurethane foam), nonwoven materials (e.g., membranes, PTFE membranes), and combinations thereof (e.g., a plastic-coated metal foil). The substrate can be configured in a variety of forms including, for example, fibers, nonwoven materials, sheets, and films.

Figure 12A:
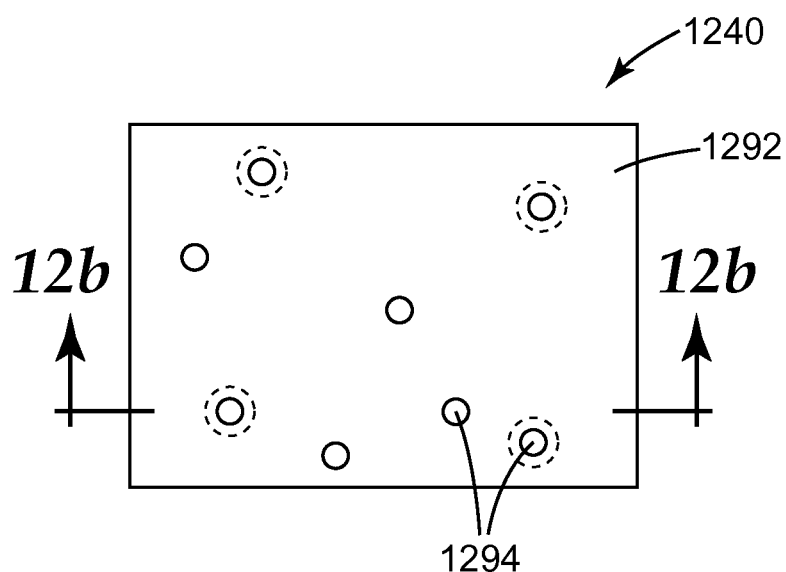
FIG. 12a is a top view of one embodiment of a release element comprising a substrate with cavities.
Figure 12B:
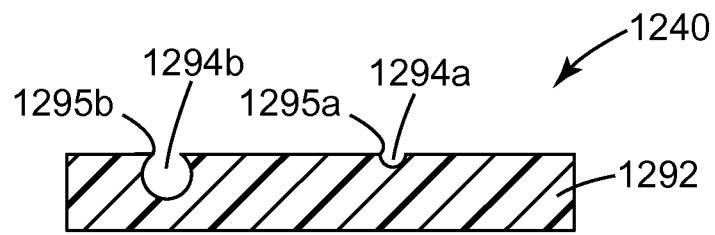

In some embodiments, the surface of the substrate can be relatively smooth. In some embodiments, at least a portion of the substrate can comprise cavities. FIG. 12a shows a top view of one embodiment of a release element 1240 comprising a substrate 1292 with cavities 1294. In the illustrated embodiment, substrate 1292 may be a film substrate. FIG. 12b shows a cross-sectional view of the release element 1240 of FIG. 12a. The illustrated embodiment shows substrate 1292 comprises cavity 1294a, wherein the cross-sectional area of the cavity opening 1295a is about equal to the largest cross-sectional area of the cavity 1294a. Substrate 1292 also includes cavity 1294b, wherein the cross-sectional area of the cavity opening 1295b is less than the largest cross-sectional area of the cavity 1294b. Without being bound by theory, it is anticipated that the ratio of the area of the cavity opening to the cavity volume can be used as one means to control the rate of release of the cell extractant from the release element. Although the illustrated embodiment comprises relatively uniform, spherical or hemispherical cavities, it is anticipated that suitable cavities include a variety of shapes, including non-uniform, irregular shapes.

Substrates, as used herein, include microreplicated substrates. Microreplication or "microreplicated" means the production of a microstructured surface (e.g., microchannels) through a process where the structured surface features retain individual feature fidelity during manufacture, from product-to-product, that varies no more than about 50 micrometers. The microreplicated surfaces preferably are produced such that the structured surface features retain individual feature fidelity during manufacture, from product-to-product, which varies no more than 25 micrometers. In accordance with the present invention, a microstructured surface comprises a surface with a topography (the surface features of an object, place or region thereof) that has individual feature fidelity that is maintained with a resolution of between about 50 micrometers and 0.05 micrometers, more preferably between 25 micrometers and 1 micrometer. Suitable microreplicated substrates are described in U.S. Patent Application Publication No. US 2007/0212266 A1, which is incorporated herein by reference in its entirety.

Figure 13:
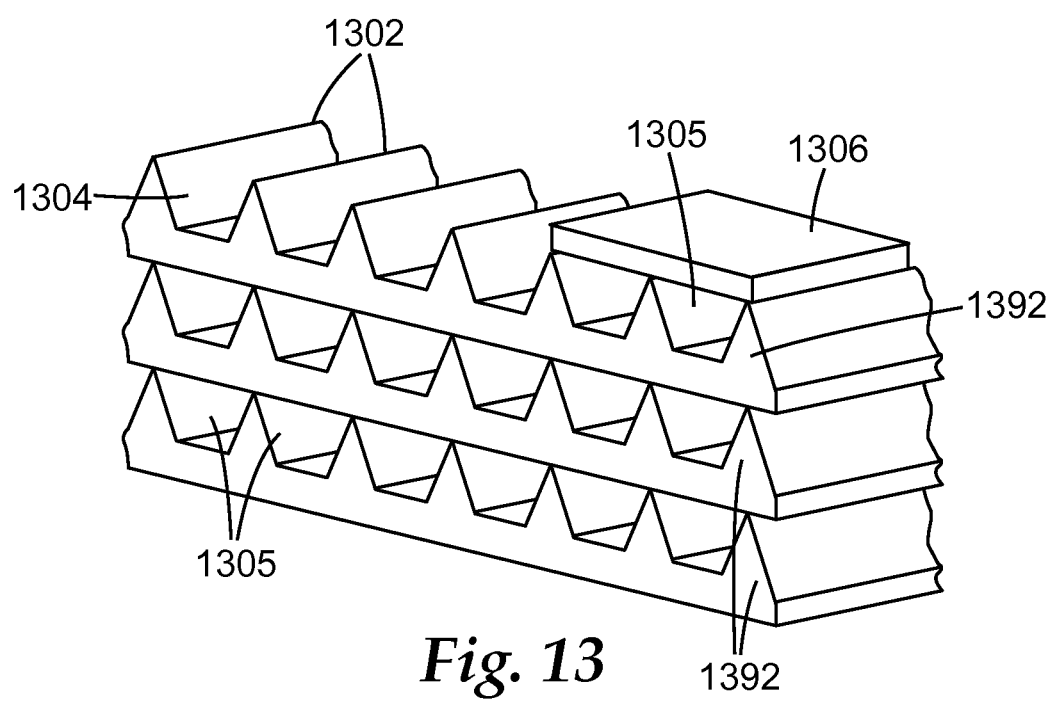
FIG. 13 is a top perspective view of one embodiment of a release element comprising microchannel cavities.

FIG. 13 shows a top perspective view of one embodiment of a release element 1340 comprising microreplicated cavities. The release element 1340 includes a substrate 1392 that comprises spaced-apart peaks 1302 forming channels 1304 there between. The substrate 1392 can be coated as described herein with a composition comprising a cell extractant. Optionally, a cover 1306 (e.g., a plastic or metal film) can be affixed (e.g., by an adhesive, not shown) to the substrate 1392, thereby forming covered channels 1305. Optionally, two or more substrates 1392 can be stacked (as shown) to create one or more layers of covered channels 1305. The substrates 1392 can be stacked after they are coated with a cell extractant or they can be stacked before they are coated with a cell extractant. In the embodiments where the substrates 1392 are stacked before coating, the individual channels can be coated by applying the cell extractant to the ends of the covered channels 1305 and the covered channels can be allowed to fill by capillary action.

The covered channels 1305 can present a relatively small opening (i.e., one or both ends of the channel) to contact a liquid in which the release element 1340 is suspended, thereby limiting and/or delaying the diffusion of an effective amount of a cell extractant out of the covered channels 1305 and into the liquid.

Release elements with microreplicated surfaces and/or cavities can be coated to fill the microchannels or cavities with a cell extractant composition. The cell extractant composition may be liquid, solid, semi-solid, or a combination of any two or more of the foregoing.

In some embodiments, the substrate can be a filter, such as Grade 4, 20-25 μm Qualitative Filter Paper, Grade 30, Glass-Fiber Filter Paper, Grade GB005, a thick (1.5 mm) highly absorbent blotting paper (all obtained from Whatman, Inc, Florham Park, N.J.), Zeta Plus Virosorb 1MDS discs (CUNO, Inc, Meriden, Conn.) and 0.45 μm MF-Millipore membrane (Millipore, Billerica, Mass.). Any one of the above substrates can be loaded a cell extractant solution containing polyvinyl alcohol. Any one of the above substrates can be loaded a cell extractant solution containing VANTOCIL (Arch Chemicals, Norwalk, Conn.). Any one of the above substrates can be loaded a cell extractant solution containing CARBOSHIELD (Lonza, Walkersville, Md.). Any one of the above substrates can be loaded a cell extractant solution containing 5% benzalkonium chloride solution.

In some embodiments, the substrate can be coated with a matrix material comprising a cell extractant, as described herein. In some embodiments, the matrix material (e.g., a polymeric material or a nonpolymer material such as a ceramic) can be substantially insoluble in a liquid (for example, an aqueous liquid comprising a sample). Additionally, or alternatively, the matrix material can be substantially insoluble in an organic solvent. In some embodiments, the matrix material can comprise an excipient that is substantially soluble and/or dispersible at ambient temperature in a liquid mixture (e.g., an aqueous solution) comprising a sample. In some embodiments, the matrix material can comprise an excipient that is substantially insoluble and nondispersible at ambient temperature in an aqueous solution (i.e., the dissolution or dispersion of the excipient can be triggered by a temperature shift and/or the addition of a chemical trigger).

In some embodiments, the matrix material used to coat the substrate can be a pre-formed matrix (e.g., a polymer matrix) comprising a cell extractant. In some embodiments, a mixture comprising matrix precursors and cell extractant are coated onto the substrate and the matrix can be formed subsequently on the substrate using, for example, polymerization processes known in the art and/or described herein. In some embodiments, a pre-formed matrix is coated onto the substrate or a matrix is formed on the substrate and, subsequently, the cell extractant is loaded into the substrate using processes known in the art and/or described herein.

Matrices, according to the present disclosure, can comprise a cell extractant admixed with an excipient. "Excipient" is used broadly to include, for example, binders, glidants (e.g., flow aids), lubricants, disintegrants, and any two or more of the foregoing. In some embodiments, coated substrate can comprise an outer coating, which may influence the release of an active substance (e.g., a cell extractant) when the coated substrate is contacted with a liquid (e.g., an aqueous liquid comprising a sample). In some embodiments, matrices can comprise fillers (e.g., a sugar such as lactose or sorbitol) as a bulking agent for the matrix. Disintegrants (e.g., a polysaccharide such as starch or cellulose) may promote wetting and/or swelling of the matrix and thereby facilitate release of the active substance when the matrix is contacted with a liquid. Sorbitol and mannitol are excipients that can promote the stability of certain cell extractants (e.g., enzymes). Mannitol can be used to delay the release of the cell extractant. In some embodiments, polyethylene glycol (PEG) is a preferred excipient to control the release of active substances from a matrix. In some embodiments, PEG compounds with molecular weights of 3300 and 8000 daltons can be used to delay the release of an active substance from a matrix.

In some embodiments, the coating mixture comprises an additive (e.g., a binder or viscosifier) to facilitate the coating process and/or to facilitate the adherence of the coating to the substrate. Non-limiting examples of additives include gums (e.g., guar gum, xanthan gum, alginates, carrageenan, pectin, agar, gellan), polysaccharides (e.g., starch, methylcellulose, carboxymethylcellulose, hydroxypropylmethylcellulose, agarose), and polypeptides (e.g., gelatin,).

Matrix materials, cell extractants, substrates, and coating additives should be selected for their compatibility with the detection system used to detect cells in a sample. This compatibility can be tested by 1) detecting an amount of analyte in a detection system (e.g., a combining ATP with luciferin and luciferase and measuring the amount of luminescence with a luminometer, as described in Example 6 of PCT International Publication No. WO 2010/129727; 2) repeating the detection step with the matrix material, cell extractant, substrate or coating additive; and 3) comparing the results of step 1 with the results of step 2 to determine whether the additive substantially inhibits the detection and/or measurement of the analyte in the reaction.

In some embodiments, the material used to coat the substrate may comprise a shell structure comprising a cell extractant, as described herein. The compatibility of a particular shell structure with a particular detection system can be determined as described herein.

In some embodiments, the coated substrate may further comprise a barrier layer. The barrier layer may serve as a means to delay the release of a cell extractant from the coated substrate. Barrier layers include, for example, erodible coatings such as those known in the art to control and/or delay the release of active ingredients from tablet or capsule medications. Barrier layers also include layers that can be disintegrated by physical or mechanical manipulation (e.g., a wax layer that can disintegrate at increased temperatures).

In some embodiments, the encapsulating materials may be activated to release an effective amount of cell extractant after the encapsulant is exposed to an activating stimulus such as pressure, shear, heat, light, pH change, exposure to another chemical, ionic strength change and the like. Activation may result in, for example, dissolution or partial dissolution of the encapsulating material, permeabilization of the encapsulating material, and/or disintegration or partial disintegration of the encapsulating material (e.g., by fracturing or melting a solid material such as, for example microcrystalline wax).

In some embodiments, release elements comprise an encapsulating material that holds and/or comprises a cell extractant. Suitable encapsulating materials are described in PCT International Publication No. WO 2010/129728 and entitled "ARTICLES WITH SHELL STRUCTURES INCLUDING A CELL EXTRACTANT AND BIODETECTION METHODS THEREOF", which is incorporated herein by reference in its entirety. The encapsulating materials can act as a physical barrier and/or a diffusion barrier to prevent the immediate dissolution and/or dispersion, for a period of time, of an effective amount of the cell extractant into a liquid mixture (for example, an aqueous mixture comprising a sample).

In some embodiments, the encapsulating materials can comprise a matrix material, as described herein.

In some embodiments, the encapsulating materials may be activated to release an effective amount of cell extractant after the encapsulant is exposed to activating stimuli such as pressure, shear, heat, light, pH change, exposure to another chemical, ionic strength change and the like. Activation may result in, for example, dissolution or partial dissolution of the encapsulating material, permeabilization of the encapsulating material (e.g. disruption of a lipid bilayer), and/or disintegration or partial disintegration of the encapsulating material (e.g., by fracturing or melting a solid material such as, for example microcrystalline wax).

Figure 14:
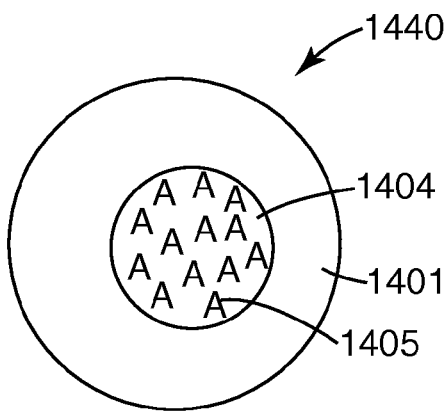
FIG. 14 is a cross-sectional view of one embodiment of a release element comprising a shell structure with a core that comprises a guest compound.

In some embodiments, the release element forms a shell structure. FIG. 14 shows an embodiment of a release element 1440 according to the present disclosure. Release element 1440 includes a shell structure 1401 and a core 1404. Located in the core 1404 is guest compound 1405 (e.g., a cell extractant as described herein). The core 1404 can comprise a liquid, a solid, a semisolid or combinations thereof. Guest compound 1405 may be dissolved and/or dispersed therein.

Figure 15:
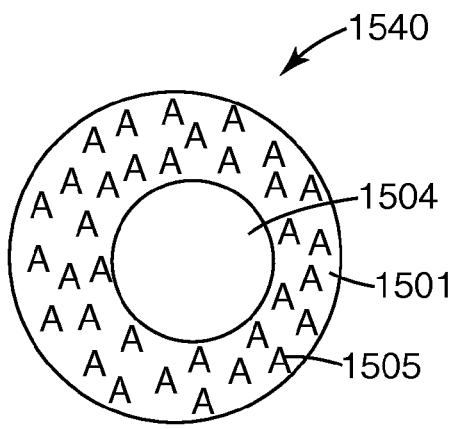
FIG. 15 is a cross-sectional view of one embodiment of a release element comprising a shell structure that comprises a guest compound.

In some embodiments, the shell structure of a release element can comprise a cell extractant. FIG. 15 shows an embodiment of a release element 1540 according to the present disclosure. Release element 1540 includes a shell structure 1501 comprising a guest compound 1505 (e.g., a cell extractant as described herein). Release element 1540 further comprises a core 1504, which can comprise a liquid, a solid, a semisolid, or combinations thereof.

Figure 16:
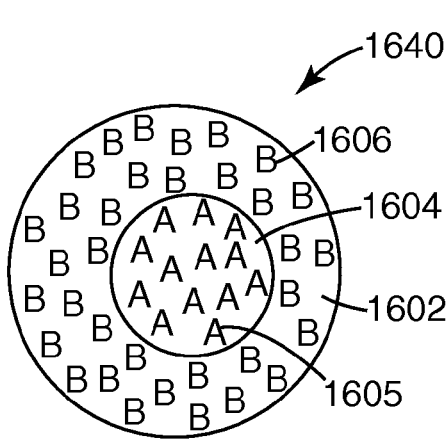
FIG. 16 is a cross-sectional view of one embodiment of a release element comprising a shell structure with a core that comprises a first guest compound and a shell structure that comprises a second guest compound.

In some embodiments, a release element can comprise two or more guest molecules. FIG. 16 shows an embodiment of a composite release element 1640 according to the present disclosure. Composite release element 1640 includes a shell structure 1602 comprising a first guest molecule 1606 and a core 1604 comprising a second guest molecule 1605. In some embodiments, first and second guest compounds (1604 and 1605, respectively) can be the same compound. In some embodiments, first and second guest compounds (1606 and 1605, respectively) can be different compounds. In some embodiments, a least one guest compound can be a cell extractant. In some embodiments, the at least one guest compound can be a detection reagent as described herein. In some embodiments, at least one guest compound can be a cell extractant and at least one guest compound can be a detection reagent.

Figure 17:
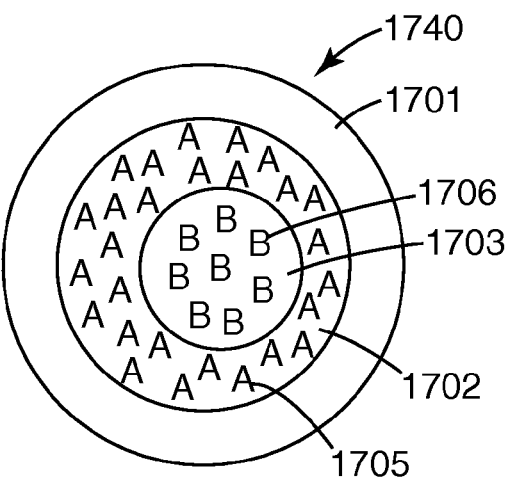
FIG. 17 is a cross-sectional view of one embodiment of a release element that comprises a plurality of shell structures arranged in successive layers.

In some embodiments, a release element can comprise two or more shell structures. FIG. 17 shows an embodiment of a release element 1740 comprising a first shell structure 1701, a second shell structure 1702, and a third shell structure 1703 (the core of release element 1740 is not shown in this view). In this embodiment, second shell structure 1702 comprises first guest compound 1705 and third shell structure 1703 comprises second guest compound 1706. In this embodiment, each successive shell structure is encapsulated by the next shell structure, in an onion-like fashion. In some embodiments, first and second guest compounds (1705 and 1706, respectively) can be the same compound. In some embodiments, first and second guest compounds (1705 and 1706, respectively) can be different compounds. In some embodiments, a least one guest compound can be a cell extractant. In some embodiments, the at least one guest compound can be a detection reagent as described herein. In some embodiments, at least one guest compound can be a cell extractant and at least one guest compound can be a detection reagent.

Figure 18:
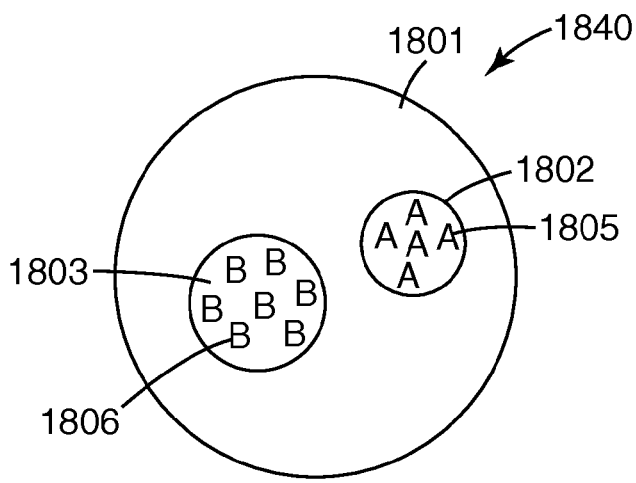
FIG. 18 is a cross-sectional view of one embodiment of a release element that comprises a plurality of shell structures arranged separately within an outer shell structure.

FIG. 18 shows an alternative embodiments of a release element 1840 comprising two or more shell structures. Release element 1840 includes a first shell structure 1801, a second shell structure 1802, and a third shell structure 1803. The second shell structure 1802 comprises a first guest compound 1805 and the third shell structure comprises a second guest compound 1806. In this embodiment, both the second shell structure 1802 and third shell structure 1803 are encapsulated by the first shell structure 1801. In some embodiments, first and second guest compounds (1805 and 1806, respectively) can be the same compound. In some embodiments, first and second guest compounds (1805 and 1806, respectively) can be different compounds. In some embodiments, a least one guest compound can be a cell extractant. In some embodiments, the at least one guest compound can be a detection reagent as described herein. In some embodiments, at least one guest compound can be a cell extractant and at least one guest compound can be a detection reagent.

Suitable shell structures of the present disclosure include polymer shells comprising, for example, cellulose, cellulose derivatives (e.g., cellulose ethers, cellulose esters, cellulose nitrate, cellulose triacetate, cellulose acetate phthalate, methyl cellulose, ethyl cellulose, hydroxypropyl cellulose, hydroxypropyl methylcellulose, carboxymethyl cellulose, and hydroxypropyl methylcellulose phthalate), polymers or copolymers of acrylates or copolymers of acrylate derivatives (e.g., polyacrylates, polymethylacrylates, poly(acrylate-methacrylate), poly(methacrylate-methylmethacrylate), polyethylacrylate-methylmethacrylate, poly(ethylacrylate-methylmethacrylate-trimethylammonioethylmethacrylate chloride), and poly (ethylacrylate-methylmethacrylate-trimethylammonioethylmethacrylate chloride)), proteins (e.g., albumin, gelatin, zein, casein, collagen, and fibrinogen), vinyl polymers (e.g., polyvinyl chloride, polyvinyl acetate, polyvinyl alcohol, polystyrene, and polyacrylonitrile), gums (e.g., guar gum, gum arabic, xanthan gum, locust bean gum), natural or modified starches, dextrins, dextrans, chitosan, alginates, and a combination of any two or more of the foregoing, as described in U.S. Pat. No. 7,485,609, which is incorporated herein by reference in its entirety.

Additionally or alternatively, suitable shell structures of the present disclosure include shell structures comprising a chromonic material. Suitable chromonic materials include those that form shell layers as described in, for example, U.S. Pat. No. 7,824,732, which is incorporated herein by reference in its entirety.

The shell layers comprised of chromonic materials can be particularly useful for the encapsulation and controlled release of guest compounds (for example, cell extractants). For example, a cell extractant can be encapsulated in a chromonic nanoparticle as described in U.S. Pat. No. 7,824,732. The chromonics can protect the cell extractant from certain environmental conditions and then controllably deliver the cell extractant under other environmental conditions. The shell comprising a complex comprising chromonic material, multivalent cations, and acid anions selected from the group consisting of $HCO_3^-$, $PO_4^{3-}$, $CH_3CHOHCOO^-$, $C_3H_5O(COO)_3^{3-}$, $BO_3^{3-}$, and $SO_4^{2-}$ (the "complexed shell"), however, can provide increased protection from certain environmental conditions as compared to chromonics alone.

Multilayered chromonic structures comprising a chromonic nanoparticle encapsulated in one or more shell layers of chromonic material are known in the art. A cell extractant can be encapsulated in the chromonic nanoparticle and/or in one or more chromonic shell layers that encapsulate the nanoparticle. The complexed shell can be used in combination with one or more chromonic shell layers (for example, the complexed shell could be the innermost shell layer, an intermediate shell layer, the outermost shell layer, or any combination thereof). Complexed shell layers can provide increased flexibility for the controlled release of cell extractants (e.g., sustained delivery).

Shell layers according to the present disclosure also include wax structures (e.g., capsules) that substantially surround the cell extractant. In some embodiments, a generally unitary body (e.g. a liquid, a solid, a plurality of solids such as particles, a semisolid, or combinations thereof) of cell extractant can be disposed inside an outer wax shell. As the wax disintegrates (e.g., by thermal melting or mechanical disruption), the cell extractant is released from the wax. Suitable waxes include paraffin wax, microcrystalline wax, and derivatives and/or combinations thereof.

Shell layers according to the present disclosure also include lipid bilayers (e.g., liposomes). The liposomes can be formed by liposome-forming techniques known in the art. The liposomes can be formed out of a solution containing a cell extractant such that at least a portion of the cell extractant is trapped in the core of the liposome. In contrast to other types of release elements, which can comprise cell extractants that may disrupt any type of lipid bilayer, liposome release elements can contain cell extractants that do not substantially impair the integrity of the lipid bilayers of the liposome. Non-limiting examples of such cell extractants include polypeptides, such as lysozyme and lysostaphin, and antibiotics that do not substantially impair the liposomes.

When the liposome is contacted with a liquid (e.g., an aqueous liquid containing a sample), the cell extractant may be released from the liposome by, for example, diffusion through the lipid bilayer. In some embodiments, the entire contents (e.g., the cell extractant solution) of the liposome may be released in a "burst" with a release factor that disrupts the integrity of the lipid bilayer using thermal or mechanical energy (e.g., heat, freeze-thaw, or sonication) or by adding a chemical release factor to permeabilize and/or solublize the lipid bilayer. In some embodiments, disruption of liposomes can be triggered using cytolytic peptides, as described in PCT International Publication No. WO 2009/102859 and entitled "POLYPEPTIDES FOR MICROBIAL DETECTION", which is incorporated herein by reference in its entirety In some embodiments, release elements of the present disclosure can include shell structures comprising a cell extractant coated on a substrate.

Cell Extractants:

In some embodiments, chemical cell extractants include biochemicals, such as proteins (e.g., cytolytic peptides and enzymes). In some embodiments, the cell extractant increases the permeability of the cell, causing the release of biological analytes from the interior of the cell. In some embodiments, the cell extractant can cause or facilitate the lysis (e.g., rupture or partial rupture) of a cell.

In some embodiments, cell extractants include chemicals and mixtures of chemicals that are known in the art and include, for example, surfactants and quaternary amines, biguanides, surfactants, phenolics, cytolytic peptides, and enzymes. Typically, the cell extractant is not avidly bound (either covalently or noncovalently) to the release element and can be released from the release element when the release element is contacted with an aqueous liquid.

Surfactants generally contain both a hydrophilic group and a hydrophobic group. The release element may contain one or more surfactants selected from anionic, nonionic, cationic, ampholytic, amphoteric and zwitterionic surfactants and mixtures thereof. A surfactant that dissociates in water and releases cation and anion is termed ionic. When present, ampholytic, amphoteric and zwitterionic surfactants are generally used in combination with one or more anionic and/or nonionic surfactants. Nonlimiting examples of suitable surfactants and quaternary amines include TRITON X-100, Nonidet P-40 (NP-40), Tergitol, Sarkosyl, Tween, SDS, Igepal, Saponin, CHAPSO, benzalkonium chloride, benzethonium chloride, 'cetrimide' (a mixture of dodecyl-, tetradecyl- and hexadecyl-trimethylammoium bromide), cetylpyridium chloride, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate). Other suitable monomeric quaternary amino salts include a dimethylalkylammonium group with the alkyl group having 2 to 22 carbon atoms or 2 to 20 carbon atoms. That is, the monomer includes a group of formula —$N(CH_3)_2(C_nH_{2n+1})^+$ where n is an integer having a value of 2 to 22. Exemplary monomers include, but are not limited to monomers of the following formula

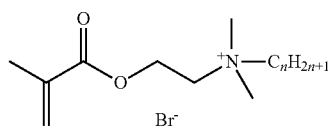

where n is an integer in the range of 2 to 22.

Non-limiting examples of suitable biguanides, which include bis-biguanides, include polyhexamethylene biguanide hydrochloride, p-chlorophenyl biguanide, 4-chlorobenzhydryl biguanide, alexidine, halogenated hexidine such as, but not limited to, chlorhexidine (1,1'-hexamethylene-bis-5-(4-chlorophenyl biguanide), and salts thereof.

Non-limiting examples of suitable phenolics include phenol, salicylic acid, 2-phenylphenol, 4-t-amylphenol, Chloroxylenol, Hexachlorophene, 4-chloro-3,5-dimethylphenol (PCMX), 2-benzyl-4-chlorophenol, triclosan, butylated hydroxytoluene, 2-Isopropyl-5-methyl phenol, 4-Nonylphenol, xylenol, bisphenol A, Orthophenyl phenol, and Phenothiazines, such as chlorpromazine, prochlorperazine and thioridizine.

Non-limiting examples of suitable cytolytic peptides include A-23187 (Calcium ionophore), Dermaseptin, Listerolysin, Ranalexin, Aerolysin, Dermatoxin, Maculatin, Ranateurin, Amphotericin B, Direct lytic factors from animal venoms, Magainin, Rugosin, Ascaphin, *Diptheria* toxin, Maxymin, Saponin, *Aspergillus haemolysin, Distinctin, Melittin, Staphylococcus aureus* toxins, (α, β, χ, δ), Alamethicin, Esculetin, Metridiolysin, Streptolysin O, Apolipoproteins, Filipin, Nigericin, Streptolysin S, ATP Translocase, Gaegurin, Nystatin, Synexin, Bombinin, GALA, Ocellatin, Surfactin, Brevinin, Gramicidin, P25, Tubulin, Buforin, Helical erythrocyte lysing peptide, Palustrin, Valinomycin, Caerin, Hemolysins, Phospholipases, Vibriolysin, Cereolysin, Ionomycin, Phylloxin, Colicins, KALA, Polyene Antibiotics, Dermadistinctin, LAGA, Polymyxin B.

Non-limiting examples of suitable enzymes include lysozyme, lysostaphin, bacteriophage lysins, achromopeptidase, labiase, mutanolysin, streptolysin, tetanolysin, a-hemolysin, lyticase, lysing enzymes from fungi, cellulase, pectinase, Driselase® Viscozyme® L, pectolyase.

In some embodiments where the release element is a hydrogel, a precursor composition from which the hydrogel is made can contain an anionic or cationic monomer, such as described in WO 2007/146722, which is incorporated herein by reference in its entirety. The anionic or cationic monomer is incorporated into the hydrogel and, as such can retain cell extractant activity. In some embodiments, the anionic or cationic monomers can be crosslinked to the surface of a hydrogel. Hydrogel beads or fibers can be dipped into a solution of the cationic monomers briefly, then quickly removed and cross-linked using actinic radiation (UV, E-beam, for example). This will result in the cationic monomer chemically bonding to the outer surface of the hydrogel beads or fibers.

In some embodiments, various combinations of cell extractants can be used in the precursor composition (from which the hydrogel is synthesized) or sorbate (which is loaded into the hydrogel after synthesis of the hydrogel). Any other known cell extractants that are compatible with the precursor compositions or the resulting hydrogels can be used. These include, but are not limited to, chlorhexidine salts such as chlorhexidine gluconate (CHG), parachlorometaxylenol (PCMX), triclosan, hexachlorophene, fatty acid monoesters and monoethers of glycerin and propylene glycol such as glycerol monolaurate, Cetyl Trimethylammonium Bromide (CTAB), glycerol monocaprylate, glycerol monocaprate, propylene glycol monolaurate, propylene glycol monocaprylate, propylene glycol moncaprate, phenols, surfactants and polymers that include a (C12-C22) hydrophobe and a quaternary ammonium group or a protonated tertiary amino group, quaternary amino-containing compounds such as quaternary silanes and polyquaternary amines such as polyhexamethylene biguanide, transition metal ions such as copper containing compounds, zinc containing compounds, and silver containing compounds such as silver metal, silver salts such as silver chloride, silver oxide and silver sulfadiazine, methyl parabens, ethyl parabens, propyl parabens, butyl parabens, octenidene, 2-bromo-2-nitropropane-1,3 diol, or mixtures of any two or more of the foregoing.

Suitable cell extractants also include dialkyl ammonium salts, including N-(n-dodecyl)-diethanolamine; cationic ethoxylated amines, including 'Genaminox K-10', Genaminox K-12, 'Genamin TCL030', and 'Genamin C100'; amidines, including propamidine and dibromopropamidine; peptide antibiotics, including polymyxin B and nisin; polyene antibiotics, including nystatin, amphotericin B, and natamycin; imidazoles, including econazole, clotramizole and miconazole; oxidizing agents, including stabilized forms of chlorine and iodine; and the cell extractants described in U.S. Pat. No. 7,422,868, which is incorporated herein by reference in its entirety.

Cell extractants are preferably chosen not to inactivate the detection system (e.g., a detection reagent such as luciferase enzyme) of the present invention. For microbes requiring harsher cell extractants (e.g., ionic detergents etc.), modified detection systems (such as luciferases exhibiting enhanced stability in the presence of these agents, such as those disclosed in U.S. Patent Application Publication No. 2003/0104507, which is hereby incorporated by reference in its entirety) are particularly preferred.

Methods of the present invention provide for the release of an effective amount of cell extractant from a release element to cause the release of biological analytes from a live cell. The present disclosure includes a variety of cell extractants known in the art and each of which may be released from the release element at a different rate and may exert its effect on living cells at a different concentration than the others. The following will provide guidance concerning the factors to be considered in selecting the cell extractant and the in determining an effective amount to include in the release element.

It is known in the art that the efficacy of any cell extractant is determined primarily by two factors—concentration and exposure time. That is, in general, the higher the concentration of a cell extractant, the greater the effect (e.g., permeabilization of the cell membrane and/or release of biological analytes from the cell) it will have on a living cell. Also, at any given concentration of cell extractant, in general, the longer you expose a living cell to the cell extractant, the greater the effect of the cell extractant. Other extrinsic factors such as, for example, pH, co-solvents, ionic strength, and temperature are known in the art to affect the efficacy of certain cell extractant. It is known that these extrinsic factors can be controlled by, for example, temperature controllers, buffers, sample preparation, and the like. These factors, as well as the cell extractant, can also have effects on the detection systems used to detect biological analytes. It is well within the grasp of a person of ordinary skill to perform a few simple experiments to determine an effective amount of cell extractant to produce the articles and perform the methods of the present disclosure.

Initial experiments to determine the effect of various concentrations of the cell extractant on the cells and/or the detection system can be performed. Initially, a candidate release element can be screened for its effect on the biological analyte detection system. For example, the release element can be infused with a cell extractant as described herein. Subsequently, the release element comprising the cell extractant can be placed into an ATP assay (without bacterial cells). The assay can be run with solutions of reagent-grade ATP (e.g. from about 0.1 to about 100 picomoles of ATP) and the amount of bioluminescence emitted by the luciferase reaction in the sample with the release element can be compared to the amount of bioluminescence emitted by a sample without the release element. Preferably, the amount of bioluminescence in the sample with the release element is greater than 50% of the amount of bioluminescence in the sample without the release element. More preferably, the amount of bioluminescence in the sample with the release element is greater than 90% of the amount of bioluminescence in the sample without the release element. Most preferably, the amount of bioluminescence in the sample with the release element is greater than 95% of the amount bioluminescence in the sample without the release element.

Additionally, the effect of the cell extractant on the release of the biological analyte from the cells can be determined experimentally, similar to that described in Example 21 of PCT International Publication No. WO 2010/129726. For example, liquid suspensions of cells (e.g., microbial cells such as *Staphylococcus aureus*) are exposed to relatively broad range of concentrations of a cell extractant (e.g., BARDAC 205M) for a period of time (e.g. up to several minutes) in the present of a detection system to detect biological analytes from a cell (e.g., an ATP detection system comprising luciferin, luciferase, and a buffer at about pH 7.6 to 7.8). The biological analyte is measured periodically, with the first measurement usually performed immediately after the cell extractant is added to the mixture, to determine whether the release of the biological analyte (in this example, ATP) from the cells can be detected. The results can indicate the optimal conditions (i.e., liquid concentration of cell extractant and exposure time) to detect the biological analyte released from the cells. As shown in Table 26 of PCT International Publication No. WO 2010/129726, the results can also indicate that, at higher concentrations of cell extractant, the cell extractant may be less effective in releasing the biological analyte (e.g., ATP) and/or may interfere with the detection system (i.e., may absorb the light or color generated by the detection reagents).

After the effective amount of cell extractant in liquid mixtures is determined, consideration should be given to the amount of cell extractant to incorporate into the release element by the methods described herein. When the release element contacts a liquid mixture (e.g., a sample in an aqueous suspension) the cell extractant can be released from the release element (e.g., by diffusion) and the concentration of the cell extractant in the liquid mixture increases until an equilibrium is reached. Without being bound by theory, it can be assumed that, until the equilibrium is reached, a concentration gradient of cell extractant will exist in the liquid, with a higher concentration of extractant present in the portion of the liquid proximal the release element. When the concentration of the cell extractant reaches an effective concentration in a portion of the liquid containing a cell, the cell releases biological analytes. The released biological analytes are thereby available for detection by a detection system.

Achieving an effective concentration of cell extractant in the liquid containing the sample can be controlled by several factors. For example, the amount of cell extractant loaded into the release element can affect final concentration of cell extractant in the liquid at equilibrium. Additionally, the amount of release element and, in some embodiments, the amount of surface area of the release element in the liquid mixture can affect the rate of release of the cell extractant from the release element and the final concentration of cell extractant in the liquid at equilibrium. Furthermore, the temperature of the aqueous medium can affect the rate at which the release element releases the cell extractant. Other factors, such as the ionic properties and or hydrophobic properties of the cell extractant and the release element may affect the amount of cell extractant released from the release element and the rate at which the cell extractant is released from the release element. All of these factors can be optimized with routine experimentation by a person of ordinary skill to achieve the desired parameters (e.g., manufacturing considerations for the articles and the time-to-result for the methods) for detection of cells in a sample. In general, it is desirable to incorporate at least enough cell extractant into the release element to achieve the effective amount (determined by the experimentation using the cell extractant without a release element) when the cell extractant reaches equilibrium between the release element and the volume of liquid comprising the sample material. It may be desirable to add a larger amount of cell extractant to the release element (than the amount determined by experimentation using the cell extractant without a release element) to reduce the amount of time it take for the release element to release an effective amount of cell extractant.

In some embodiments wherein the release element comprises a matrix, the cell extractant can diffuse into the matrix, diffuse out of the matrix, or both. The rate of diffusion should be controllable by, for example, varying the matrix material and/or the crosslink density, by varying the polar solvent in which the matrix is made, by varying the solubility of the cell extractant in the polar solvent in which the matrix is made, and/or by varying the molecular weight of the cell extractant. The rate of diffusion can also be modified by varying the shape, size, and surface topography of the matrix.

Without being bound by theory, it is believed that migration of the cell extractant out of the release element can occur spontaneously (e.g., by diffusion) upon contact of the release element and a liquid (e.g., an aqueous liquid comprising a sample). In some embodiments, migration of the cell extractant out of the release element can be facilitated.

In some embodiments, migration of the cell extractant out of the release element is facilitated by providing a chemical facilitator. The chemical facilitator can be, for example, an acid or a base. Changing the pH of the mixture may disrupt ionic interaction between the release element and the cell extractant, thereby facilitating the migration of the cell extractant out of the release element. PCT International Publication No. WO2005/094792 entitled ANIONIC HYDROGEL MATRICES WITH pH DEPENDENT MODIFIED RELEASE AS DRUG CARRIERS, which is incorporated herein by reference in its entirety, discloses hydrogel compositions with pH dependent modified release of drugs or disinfectants. In some embodiments, migration of the cell extractant can be facilitated by changing the ionic strength of the liquid (e.g., by adding or removing a salt).

In some embodiments, migration of the cell extractant out of the release element is facilitated by a mechanical process. Non-limiting examples of suitable mechanical processes include vibrating, stirring, or compressing the release element.

The release element can be contacted with the liquid sample material either statically, dynamically (i.e., with mixing by vibration, stirring, aeration or compressing, for example), or a combination thereof. Example 16 of PCT International Publication No. WO 2010/129726 shows that mixing can cause a faster release of an effective amount of cell extractant from a release element. Example 17 of PCT International Publication No. WO 2010/129726 shows that compressing the release element can, in some embodiments, cause a faster release of an effective amount of cell extractant from release element. Compressing the release element can include, for example, pressing the release element against a surface and/or crushing the release element. Thus, in some embodiments, mixing can advantageously provide a faster release of cell extractant and thereby a faster detection of biological analytes (e.g., from live cells) in a sample. In some embodiments, compressing the release element (e.g., by exerting pressure against the release element using a sample acquisition device such as a swab or a spatula, a carrier (described below) or some other suitable implement) can advantageously provide a faster release of cell extractant and thereby a faster detection of biological analytes in a sample. Additionally, the step of compressing the release element can be performed to accelerate the release of the cell extractant at a time that is convenient for the operator.

In some embodiments, static contact can delay the release of an effective amount of cell extractant and thereby provide additional time for the operator to carry out other procedures (e.g., reagent additions, instrument calibration, and/or specimen transport) before detecting the biological analytes. In some embodiments, it may be advantageous to hold the mixture statically until a first biological analyte measurement is taken and then dynamically mix the sample to reduce the time necessary to release an effective amount of cell extractant.

It is fully anticipated that the most preferred concentration(s) or concentration range(s) functional in the methods of the invention will vary for different microbes and for different cell extractants and may be empirically determined using the methods described herein or commonly known to those skilled in the art.

Samples and Sample Acquisition Devices:

Articles and methods of the present disclosure provide for the detection of biological analytes in a sample. In some embodiments, the articles and methods provide for the detection of biological analytes from live cells in a sample. In certain embodiments, the articles and methods provide for the detection of live microbial cells in a sample. In certain preferred embodiments, the articles and methods provide for the detection of live bacterial cells in a sample.

The term "sample" as used herein, is used in its broadest sense. A sample is a composition that may contain a biological analyte (e.g., ATP) that is analyzed using the invention. The biological analyte may be present in a cell (e.g. a bacterium) in the sample. While often a sample is known or suspected to contain a cell or a population of cells, optionally in a growth media, or a cell lysate. A sample may also be a solid surface (e.g., a swab, membrane, filter, particle) that may include on the surface an attached cell or population of cells. It is contemplated that for such a solid sample, an aqueous sample is made by contacting the solid with a liquid (e.g., an aqueous solution) which can be mixed with cell concentration agents according to the present invention.

Suitable samples include samples of solid materials (e.g., particulates, filters), semisolid materials (e.g., a gel, a liquid suspension of solids, or slurry), a liquid, or combinations thereof. Suitable samples further include surface residues comprising solids, liquids, or combinations thereof. Nonlimiting examples of surface residues include residues from environmental surfaces (e.g., floors, walls, ceilings, fomites, equipment, water, and water containers, air filters), food surfaces (e.g., vegetable, fruit, and meat surfaces), food processing surfaces (e.g., food processing equipment and cutting boards), and clinical surfaces (e.g., tissue samples, skin and mucous membranes). Samples can also include mixtures such as crude or partially-refined oil, gasoline, or paint.

The collection of sample materials, including surface residues, for the detection of biological analytes is known in the art. Various sample acquisition devices, including pipettes, spatulas, sponges, swabs and the like have been described and can be used in the methods of the present invention.

Cell Concentration Agents:

Methods of the present disclosure include the use of cell concentration agents to couple with cells that are present in a liquid sample. The cell concentration agent is contacted for a period of time with a liquid sample. The cells can be coupled to the cell concentration agent either covalently, noncovalently (e.g., by hydrophobic or ionic interactions), or by a combination of covalent and noncovalent coupling. After the cells have coupled to the cell concentration agent, the cell concentration agent can be removed from the liquid sample by, for example, sedimentation, flocculation, centrifugation, filtration or any combination of the foregoing.

"Cell concentration agent" is used broadly to include materials (e.g., particles, fibers) that can be suspended in a liquid and, thereby, capture and retain microorganisms that are present in the liquid. Although cell concentration agents can be collected by a filtration process, they do not necessarily require a filtration process to capture the microorganisms.

Certain cell concentration agents are known in the art and are suitable for use in methods of the present disclosure. Nonlimiting examples of suitable cell concentration agents include hydroxyapatite (Berry et al.; Appl. Environ. Microbiol.; 63:4069-4074; 1997), magnetic beads (Oster et al., J. Magnetism and Magnetic Mat.; 225:145-150; 2001), ferrimagnetic mineral, magnetite, chitosan, and affinity supports. The use of compositions including an immobilized-metal support material to capture or concentrate microorganisms from a sample is described in U.S. Patent Application Publication No. US 2010/0062421, and entitled "COMPOSITIONS, METHODS, AND DEVICES FOR ISOLATING BIOLOGICAL MATERIALS", which is incorporated herein by reference in its entirety.

One exemplary type of concentration agents include diatomaceous earth and surface treated diatomaceous earth. Specific examples of such concentration agents can be found in commonly assigned U.S. Patent Application Publication No. US 2010/0209961, and entitled "MICROORGANISMS CONCENTRATION PROCESS AND AGENT"; the disclosure of which is incorporated herein by reference. When dispersed or suspended in water systems, inorganic materials exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). In an embodiment, concentration agents can have zeta potentials that are at least somewhat more positive than that of untreated diatomaceous earth, and the concentration agents can be surprisingly significantly more effective than untreated diatomaceous earth in concentrating microorganisms such as bacteria, the surfaces of which generally tend to be negatively charged.

One exemplary type of concentration agent includes diatomaceous earth. Another exemplary type of concentration agent includes surface treated diatomaceous earth. Exemplary surface treatment includes a surface modifier, such as titanium dioxide, fine-nanoscale gold or platinum, or a combination thereof. Such surface treatments can be surprisingly more effective than untreated diatomaceous earth in concentrating microorganisms. The surface treatment can also further include a metal oxide selected from ferric oxide, zinc oxide, aluminum oxide, and the like, and combinations thereof. In an embodiment, ferric oxide is utilized. Although noble metals such as gold have been known to exhibit antimicrobial characteristics, the gold-containing concentration agents can be effective not only in binding the microorganisms but also in leaving them viable for purposes of detection or assay.

Useful surface modifiers include fine-nanoscale gold; fine-nanoscale platinum; fine-nanoscale gold in combination with at least one metal oxide (for example, titanium dioxide, ferric oxide, or a combination thereof); titanium dioxide; titanium dioxide in combination with at least one other (that is, other than titanium dioxide) metal oxide; and the like; and combinations thereof. In an embodiment, surface modifiers such as fine-nanoscale gold; fine-nanoscale platinum; fine-nanoscale gold in combination with at least ferric oxide or titanium dioxide; titanium dioxide; titanium dioxide in combination with at least ferric oxide; or combinations thereof can be utilized.

In an embodiment surface modifiers such as the following can be utilized: fine-nanoscale gold; fine-nanoscale platinum; fine-nanoscale gold in combination with ferric oxide or titanium dioxide; titanium dioxide; titanium dioxide in combination with ferric oxide; and combinations thereof. In an embodiment, fine-nanoscale gold; fine-nanoscale gold in combination with ferric oxide or titanium dioxide; titanium dioxide in combination with ferric oxide; and combinations thereof can be utilized. Fine-nanoscale gold, fine-nanoscale gold in combination with ferric oxide or titanium dioxide, and combinations thereof can also be utilized in an embodiment.

Another exemplary type of concentration agent includes gamma-FeO(OH) (also known as lepidocrocite). Specific examples of such concentration agents can be found in commonly assigned U.S. Patent Application Publication No. US 2010/0248214, and entitled "MICROORGANISM CONCENTRATION PROCESS"; the disclosure of which is incorporated herein by reference. Such concentration agents have been found to be surprisingly more effective than other iron-containing concentration agents in capturing gram-negative bacteria, which can be of great concern in regard to food- and water-borne illnesses and human bacterial infections. The concentration agents can further include (in addition to gamma-FeO(OH)) other components (for example, boehmite ($\alpha$-AlO(OH)), clays, iron oxides, and silicon oxides). In embodiments where such other components are included, they generally do not significantly interfere with the intimate contact of the sample and the concentration agent.

Gamma-FeO(OH) is known and can be chemically synthesized by known methods (for example, by oxidation of ferrous hydroxide at neutral or slightly acidic pHs, as described for purposes of magnetic tape production in U.S. Pat. No. 4,729,846 (Matsui et al.), the description of which is incorporated herein by reference. Gamma-FeO(OH) is also commercially available (for example, from Alfa Aesar, A Johnson Matthey Company, Ward Hill, Mass., and from Sigma-Aldrich Corporation, St. Louis, Mo.).

In an embodiment that utilized gamma-FeO(OH) as a concentration agent, the gamma-FeO(OH) is generally in the form of microparticles. In an embodiment, it is in the form of microparticles having particle sizes (largest dimension) in the range of about 3 micrometers (in other embodiments, about 5 micrometers; or about 10 micrometers) to about 100 micrometers (in other embodiments, about 80 micrometers; or about 50 micrometers; or about 35 micrometers; where any lower limit can be paired with any upper limit of the range). In an embodiment, the particles are agglomerates of smaller particles. The particles can include crystallites that are less than about 1 micrometer in size (in an embodiment, less than about 0.5 micrometer in size). The crystallites can be present as acicular crystallites, as raft-like structures comprising acicular crystallites, or as combinations of the acicular crystallites and raft-like structures.

In an embodiment, the concentration agents have a surface area as measured by the BET (Brunauer-Emmett-Teller) method (calculation of the surface area of solids by physical adsorption of nitrogen gas molecules) that is greater than about 25 square meters per gram ($m^2/g$); in an embodiment greater than about 50 $m^2/g$; and in another embodiment greater than about 75 $m^2/g$.

An agglomerated form of the particles can provide the adsorptive capabilities of fine particle systems without the handling and other hazards often associated with fine particles. In addition, such agglomerate particles can settle readily in fluid and thus can provide rapid separation of microorganisms from a fluid phase (as well as allowing low back pressure when filtered).

Another exemplary type of concentration agents includes metal silicates. Specific examples of such concentration agents can be found in commonly assigned U.S. Patent Application Publication No. US 2010/0190171, and entitled "MICROORGANISM CONCENTRATION PROCESS"; the disclosure of which is incorporated herein by reference. Exemplary metal silicates can have a surface composition having a metal atom to silicon atom ratio of less than or equal to about 0.5 (in an embodiment, less than or equal to about 0.4; in another embodiment, less than or equal to about 0.3; in yet another embodiment, less than or equal to about 0.2), as determined by X-ray photoelectron spectroscopy (XPS). In an embodiment, the surface composition also includes at least about 10 average atomic percent carbon (in an embodiment, at least about 12 average atomic percent carbon; in yet another embodiment at least about 14 average atomic percent carbon), as determined by X-ray photoelectron spectroscopy (XPS). XPS is a technique that can determine the elemental composition of the outermost approximately 3 to 10 nanometers (nm) of a sample surface and that is sensitive to all elements in the periodic table except hydrogen and helium. XPS is a quantitative technique with detection limits for most elements in the 0.1 to 1 atomic percent concentration range. Exemplary surface composition assessment conditions for XPS can include a take-off angle of 90 degrees measured with respect to the sample surface with a solid angle of acceptance of ±10 degrees.

When dispersed or suspended in water systems, inorganic materials such as metal silicates exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). Exemplary concentration agents can have zeta potentials that are more negative than that of, for example, a common metal silicate such as ordinary talc. Yet the concentration agents are surprisingly more effective than talc in concentrating microorganisms such as bacteria, the surfaces of which generally tend to be negatively charged. In an embodiment, the concentration agents have a negative zeta potential at a pH of about 7 (in an embodiment, a Smoluchowski zeta potential in the range of about −9 millivolts to about −25 millivolts at a pH of about 7; in another embodiment, a Smoluchowski zeta potential in the range of about −10 millivolts to about −20 millivolts at a pH of about 7; in yet another embodiment a Smoluchowski zeta potential in the range of about −11 millivolts to about −15 millivolts at a pH of about 7).

Useful metal silicates include, but are not limited to, amorphous silicates of metals such as magnesium, calcium, zinc, aluminum, iron, titanium, and the like, and combinations thereof. In an embodiment, magnesium, zinc, iron, titanium, or combinations thereof can be utilized. In yet another embodiment, magnesium is utilized. In an embodiment, amorphous metal silicates in at least partially fused particulate form can be utilized. In an embodiment, amorphous, spheroidized metal silicates can be utilized. In yet another embodiment, amorphous, spheroidized magnesium silicate can be utilized. Metal silicates are known and can be chemically synthesized by known methods or obtained through the mining and processing of raw ores that are naturally-occurring.

Some amorphous metal silicates are commercially available. For example, amorphous, spheroidized magnesium silicate is commercially available for use in cosmetic formulations (for example, as 3M Cosmetic Microspheres CM-111, available from 3M Company, St. Paul, Minn.).

In addition to amorphous metal silicates, the concentration agents can also include other materials including oxides of metals (for example, iron or titanium), crystalline metal silicates, other crystalline materials, and the like, provided that the concentration agents have the above-described surface compositions. In an embodiment, a concentration agent contains essentially no crystalline silica.

The concentration agents can be used in any form that is amenable to sample contact and microorganism capture. In an embodiment, the concentration agents are used in particulate form. In an embodiment, the concentration agent is in the form of microparticles. In an embodiment, the concentration agent is in the form of microparticles having a particle size in the range of about 1 micrometer (in an embodiment, about 2 micrometers) to about 100 micrometers (in an embodiment, about 50 micrometers; in another embodiment, about 25 micrometers; in yet another embodiment about 15 micrometers; where any lower limit can be paired with any upper limit of the range).

Microbial concentration or capture using concentration agents is generally not specific to any particular strain, species, or type of microorganism and therefore provides for the concentration of a general population of microorganisms in a sample. Specific strains of microorganisms can then be detected from among the captured microorganism population using any known detection method with strain-specific probes. Thus, the concentration agents can be used for the detection of microbial contaminants or pathogens (particularly food-borne pathogens such as bacteria) in clinical, food, environmental, or other samples.

In carrying out the process of the invention, the concentration agents can be used in any form that is amenable to sample contact and microorganism capture (for example, in particulate form or applied to a support such as a dipstick, film, filter, tube, well, plate, beads, membrane, or channel of a microfluidic device, or the like). Preferably, the concentration agents are used in particulate form. Optionally, the cell concentration agent may comprise a binding partner (e.g., an antibody, an antibody fragment, an antigen-binding domain, a lectin (e.g., Concanavalin A), a receptor, a phage receptor, or the like), which can couple to a microorganism. The coupling can be direct or indirect. The coupling can be selective for certain microorganism types or it can be nonselective.

The amount of concentration agent used to capture microorganisms from a sample can depend at least in part on the type of concentration agent utilized, the sample size, the receptacle type and size, sample mixing, the particular application, other factors not specifically discussed herein, or a combination thereof. The capture efficiency (the percent of microorganisms in the sample bound to concentration agent) can generally be increased by allowing increased time for the microorganism to come in contact with the concentration agent. The capture efficiency can also be increased by having a higher concentration of concentration agent, which decreases the mean diffusion distance a microorganism must travel to be captured, leading to a shorter incubation time. Therefore, as a generality, the more concentration agent added, the shorter incubation time necessary to capture the same amount of microorganisms.

In an embodiment, an appropriate amount of concentration agent can vary given the time necessary to wait for the microorganisms to be bound to the concentration agent (referred to as "capture time"). For example, for a capture time of 1 minute, 1000 mg of concentration agent per 10 mL of sample could be appropriate; for a capture time of 10 minutes, 100 mg of concentration agent per 10 mL of sample could be appropriate; and for a capture time of 60 minutes, 10 mg of concentration agent per 10 mL of sample could be appropriate. In an embodiment, from about 1 mg to about 100 mg of concentration agent per 10 mL of sample can be utilized. In an embodiment, from about 1 mg to about 50 mg of concentration agent per 10 mL of sample can be utilized. In an embodiment, from about 10 mg to about 25 mg of concentration agent per 10 mL of sample can be utilized. In an embodiment utilizing a metal silicate concentration agent for example, about 10 mg of a metal silicate concentration agent per 10 mL of sample can be utilized. In an embodiment utilizing a metal silicate concentration agent for example, about 25 mg of a metal silicate concentration agent per 10 mL of sample can be utilized.

Detection Devices:

The present disclosure provides devices that can be used to detect microorganisms in a sample. The devices can include a housing comprising at least two receptacles with a passageway there between, an optional cell concentration agent disposed in a first receptacle of the housing, a means for isolating at least two receptacles in the housing, and means for transferring the cell concentration agent from the first receptacle to a second receptacle of the housing. In some embodiments, the housing can include the means (e.g. a frangible seal) for isolating the two receptacles. In some embodiments, the housing can include the means (e.g., a valve) for transferring the cell concentration agent from the first receptacle to the second receptacle of the housing. In some embodiments, the devices further can include a reagent for detecting microorganisms. In certain embodiments, the devices further can include a release element comprising a cell extractant. The cell extractant can facilitate the detection of a biological analyte from the microorganism.

Turning now to the drawings, FIG. 1A shows a cross-sectional view of the components of one embodiment of a detection device 100 according to the present disclosure. The detection device components comprise a housing 110 and a plunger 150. The housing 110 includes an upper part 112 adjacent a lower part 114. The upper part 112 and lower part 114 can be formed separately from polymeric material, such as polyethylene or polypropylene, by processes that are well-known in the art such as, for example, molding. The parts can be dimensioned such that they can be press-fit together to provide a substantially liquid-tight coupling or, alternatively, they can be coupled together by means that are known in the art (e.g., by an adhesive, sonic welding, or the like). Alternatively, the housing could be formed as a single unit by processes that are known in the art, such as extruding a hollow body, molding the passageway, and sealing the bottom of the housing with a process involving heat, for example. In other embodiments, an insert part, comprising the narrow passageway, could be placed into a unitary housing to form the first and second receptacles (120 and 124, respectively).

At the end of the upper part 112 distal the lower part 114, is an opening 113 that is dimensioned to receive the plunger 150. At the opposite end of the upper part 112 is a passageway 116 that opens into the lower part 114 of the housing 110. In the illustrated embodiment, the passageway 116, which has a cross-sectional area that is smaller than the cross-sectional area of the first receptacle 120, is shown as an inward extension of the wall that forms the upper part 112. Alternatively, the passageway 116 could be formed by an insert that fits inside the wall of the upper part 112 adjacent the lower part 114 of the housing 110 (not shown). The insert could form the passageway 116 adjacent the lower part 114 of the housing 110. The relative proportions of the upper part 112, lower part 114, and passageway 116 in FIG. 1A are merely illustrative and can be adapted, as necessary to accommodate various parameters, such as sample volume and/or instrument limitations. The plunger 150 comprises a shaft 151 with a handle 152 at one end and a plurality of seals (first lower seal 156 and second lower seal 157) at the opposite end. Optionally, the plunger 150 can comprise one or more upper seals 154 and/or an index mark 153. The relative distances between the handle 152, first lower seal 156 and second lower seal 157 are described below. Also shown in FIG. 1A is optional detection reagent 165 and optional release element 162.

"Detection reagent" is used herein in its broadest sense. A detection reagent is a reagent that can be used in a reaction to detect a biological analyte. Nonlimiting examples of detection reactions include interaction between binding partners (e.g., antigen-antibody, receptor-ligand, probe-target, and hybridization binding interactions) and/or catalytic reactions (e.g., enzyme-mediated reactions such as, for example, fluorogenic reactions, chromogenic reactions, lumigenic reactions, or polymerization reactions). Detection reagents may participate (e.g., as a binding partner, an enzyme, an enzyme substrate, or an indicator) in the detection reaction and/or may facilitate (e.g., as a buffer, a cofactor, or a component of a coupled reaction) a detection reaction. Exemplary detection reagents include enzymes, including, for example, luciferase, adenylate kinase, peroxidase, alkaline phosphates, apyrase, and the like; enzyme substrates, including, for example, luciferin, methylumbelliferyl phosphate, o-nitrophenylphosphate, p-nitrophenylphosphate, and 5-bromo-4-choloro-3-indoxyl-phosphate; buffers, including, for example, phosphate buffer, TRIS buffer, and HEPES buffer; and cofactors, including, for example, FADH, NADH, coenzyme A, and the like.

Detection reagents can be included in the housing 110 in various configurations. For example, the detection reagent 165 can comprise a dried or partially-dried coating, as shown in FIG. 1A. Suitable alternative configurations (not shown) for the detection reagent 165 are well known in the art and include, for example, liquid reagents (optionally, in a frangible compartment, such as an ampoule), powders, gels, tablets, lyophilized reagents, coated films, cakes, and drieddown reagents.

FIG. 1B shows a cross-sectional view of a detection device 100 comprising the housing 110 with the plunger 150 of FIG. 1A. This drawing illustrates a configuration in which the device 100 can be stored before use. The plunger 150 is fully-inserted in the housing 110. In this position, the lower edge of the handle 152 blocks the opening 113 of the upper part 112 of the housing 110, thereby preventing material from entering or exiting the housing 110. Optional upper seals 154 can also serve to prevent materials from entering or exiting the housing 110. The upper seals 154 are dimensioned to contact the inner surface of the wall of the upper part 112 of the housing 110 and are made of a suitable material (e.g., poly propylene, butyl rubber) to form a barrier, preferably a liquid-resistant barrier.

When the plunger 150 is in the position shown in FIG. 1B, the first lower seal 156 blocks the passageway 116, thereby isolating the first receptacle 120 from the second receptacle 124 of the housing 110. When the plunger 150 is in the position shown in FIG. 1B, a portion of the plunger 150 which includes the second lower seal 157 extends into the second receptacle 124 and does not contact the walls of lower part 114 of the housing 110. The first lower seal 156 and second lower seal 157 are dimensioned to contact the walls of the passageway 116 and are made of a suitable material (e.g., poly propylene, butyl rubber) to form a barrier, preferably a liquid-resistant barrier in the passageway 116 between the first receptacle 120 and the second receptacle 124. Also shown in FIG. 1B is an optional concentration agent 130, located in the first receptacle 120.

FIG. 1C shows a cross-sectional view of the device 100 of FIG. 1B with the plunger 150 in a second position. This plunger 150 position can be used, for example, to load a sample into the housing 110. The plunger 150 can be grasped by the handle 152 and withdrawn until the second lower seal 157 is proximate the upper end of the passageway 116. The optional index mark 153 on the plunger shaft 151 can be used (e.g., when it is aligned with the opening 113) to indicate the proper location of the plunger 150 to attain this position. FIG. 1C further comprises a liquid sample 140 that is contacting the concentration agent 130 in the first receptacle 120. During use, the device 100 can be vortexed or vibrated, for example, to mix the concentration agent 130 and the liquid sample 140. After a period of time, the concentration agent 130 can settle to the bottom of the first receptacle 120, as shown in FIG. 1C. In some embodiments, an optional taper region 118 is located adjacent the passageway 116. The taper region 118 can be formed from the same material and/or process as the upper part 112 of the housing 110 and/or the passageway 116. In use, the taper region 118 can direct toward the passageway 116 liquid-suspended particles (e.g., cell concentration agent 130) that are sedimenting toward the passageway 116 within the housing 110.

FIG. 1D shows a cross-sectional view of the device 100 of FIG. 1C with the plunger 150 returned to the first position shown in FIG. 1B. The lower edge of the handle 152 is proximate the opening 113 and a portion 142 of the liquid sample, containing the concentration agent 130 is transferred to the second receptacle 124, where the portion 142 can interact with a detection reagent 165 (shown in FIG. 1A), if present. Non-limiting examples of interactions between the portion 142 and the detection reagent 165 include dissolution and/or suspension of the detection reagent, binding interactions between the detection reagent and a biological analyte present in the portion, and/or a catalytic reaction. FIG. 1D also shows the portion 142 of the liquid sample contacting the release element 162 in the second receptacle 124, which can result in the release of a cell extractant from the release element 162.

In the embodiment illustrated in FIG. 1, the means for isolating the first receptacle 120 from the second receptacle 124 comprises the first lower seal 156 and/or second lower seal 157 of the plunger 150 in combination with the passageway 116. In the embodiment illustrated in FIG. 1, the means for transferring the concentration agent 130 from the first receptacle 120 to the second receptacle 124 includes the passageway 116 and the first lower seal 156 and second lower seal 157 of the plunger 150.

FIG. 2A shows a cross-sectional view of a plunger 250 and a partially-exploded cross-sectional view of a housing 210, which are components of one embodiment of a detection device 200 according to the present invention. The housing 210 includes an upper part 212 adjacent a lower part 214. The upper part 212 and lower part 214 can be formed as described above.

At the end of the upper part 212 distal the lower part 214, is an opening 213 that is dimensioned to receive the plunger 250. At the opposite end of the upper part 212 is a passageway 216, as described above. Adjacent the passageway 216 is an optional taper region 218, as described herein. Frangible seals 260a and 260b divide the housing into the first receptacle 220, second receptacle 224, and third receptacle 226.

In this embodiment, the third receptacle 226 is disposed between the first receptacle 220 and second receptacle 224. Frangible seals 260a and 260b are preferably made from a water-resistant material (e.g., a thin polymeric film, a polymer-coated paper, a thin foil) and can be secured to the walls of the housing 210 using materials and/or processes that are known in the art (e.g., an adhesive, heat-sealing, ultrasonic welding) to form a water-resistant frangible barrier.

Located in the third receptacle 226 is a release element 262 comprising a cell extractant. In some embodiments, the release element can comprise a hydrogel. Suitable examples of hydrogels comprising a cell extractant are described in PCT International Publication No. WO 2010/039627, and entitled "BIODETECTION ARTICLES", which is incorporated herein by reference in its entirety.

The relative proportions of the three receptacles in FIG. 2A are merely illustrative and can be adapted, as necessary to accommodate various parameters, such as sample volume and/or instrument limitations. Also shown in FIG. 2A are an optional concentration agent 230, optional detection reagent 265 as described herein and optional removable cap 278. Cap 278 can be made from, for example, a polymeric material (e.g., polyethylene, polypropylene) using processes known in the art (e.g., molding) and can be dimensioned to form a liquid-resistant cover for the housing 210.

The plunger 250 comprises a shaft 251 with a handle 252 at one end and the lower seal 256 and piercing end 259 at the opposite end. Preferably, the lower seal 256 dimensioned to contact the walls of the passageway 216 and is made of a suitable material (e.g., poly propylene, butyl rubber) to form a barrier, preferably a liquid-resistant barrier, in the passageway 216. Optionally, the plunger 250 can comprise one or more upper seals 254 as described above. The relative distances between the handle 252, lower seal 256 and the piercing end 259 are described below.

FIG. 2B shows a cross-sectional view of the device 200 of FIG. 2A. In this view, the housing 210 further comprises a liquid sample 240 in the first receptacle 220. The cap 278 is firmly seated on the housing 210 and, thus, the liquid sample 240 can be mixed with the cell concentration agent 230 by processes that are known in the art such as, for example, vortexing, vibrating, shaking, or inverting the housing 210. After mixing, the cell concentration agent 230 can be allowed to settle onto the frangible seal 260a in the passageway 216.

Figure 2C:
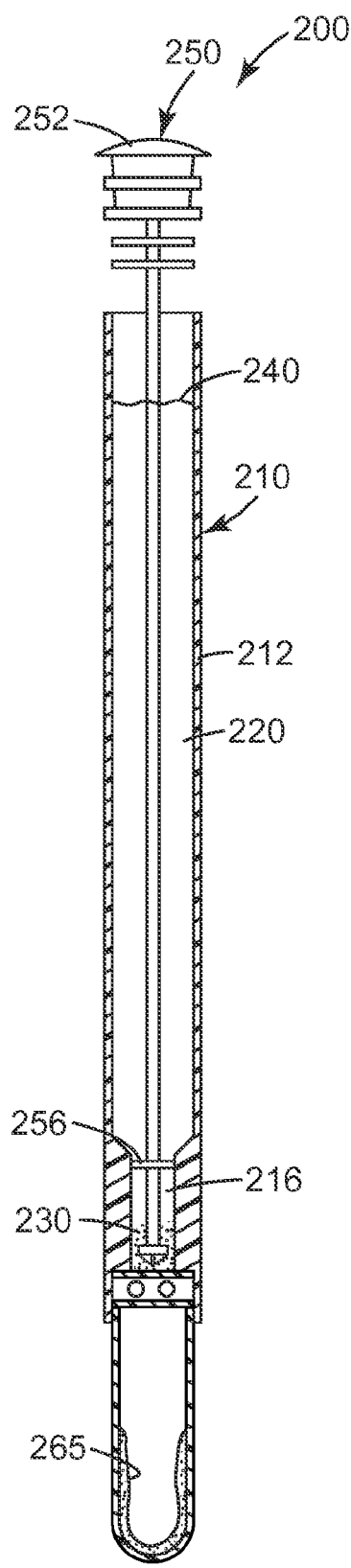
FIG. 2C shows a cross-sectional view of the housing of FIG. 2B without the cap and with a plunger disposed in a first position in the housing.

FIG. 2C shows a cross-sectional view of the device 200 comprising the housing 210 of FIG. 2B with a plunger 250 partially inserted therein. In this position, the lower seal 256 of the plunger 250 contacts the walls of the passageway 216, thereby isolating in the passageway 216 at least a portion 242 from the rest of the liquid sample 240. Also isolated in the passageway 216 is the cell concentration agent 230.

Figure 2D:
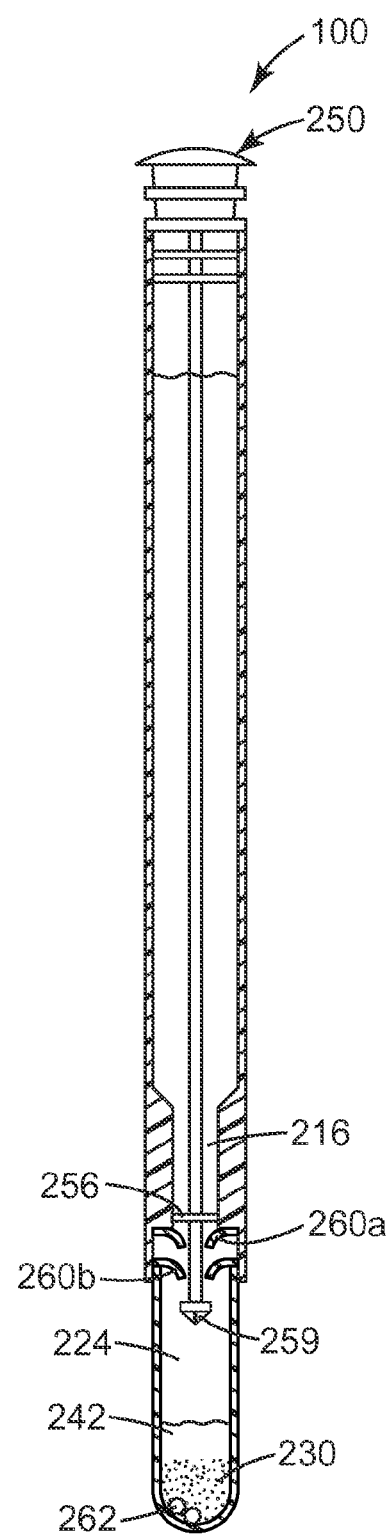
FIG. 2D shows a cross-sectional view of the device of FIG. 2C with the plunger disposed in a second position in the housing and the cell concentration agent transferred to the second receptacle of the housing.

FIG. 2D shows a cross-sectional view of the device 200 of FIG. 2C with the plunger 250 fully inserted therein. The lower seal 256 of the plunger 250 contacts the walls of the passageway 216 and the piercing end 259 has punctured frangible seals 260a and 260b, thereby transferring the portion 242 of the liquid sample, the cell concentration agent 230, and the release element 262 into the second receptacle 224, where the portion 242 can interact with optional detection reagent 265 (shown in FIG. 2A), if present. Non-limiting examples of interactions between the portion 242 and the detection reagent 265 include dissolution and/or suspension of the detection reagent, binding interactions between the detection reagent and a biological analyte present in the portion, and/or a catalytic reaction.

In the illustrated embodiment of FIG. 2, the means for isolating the first receptacle 220 from the second receptacle 224 includes the frangible seals 260a and 260b. Means for isolating the first receptacle 220 from the second receptacle 224 can also include the lower seal 256 of the plunger 250 in combination with the passageway 216. In the illustrated embodiment of FIG. 2, the means for transferring the cell concentration agent 230 from the first receptacle 220 to the second receptacle 224 includes the piercing end 259 and lower seal 256 of the plunger 250 and the passageway 216.

Figure 3A:
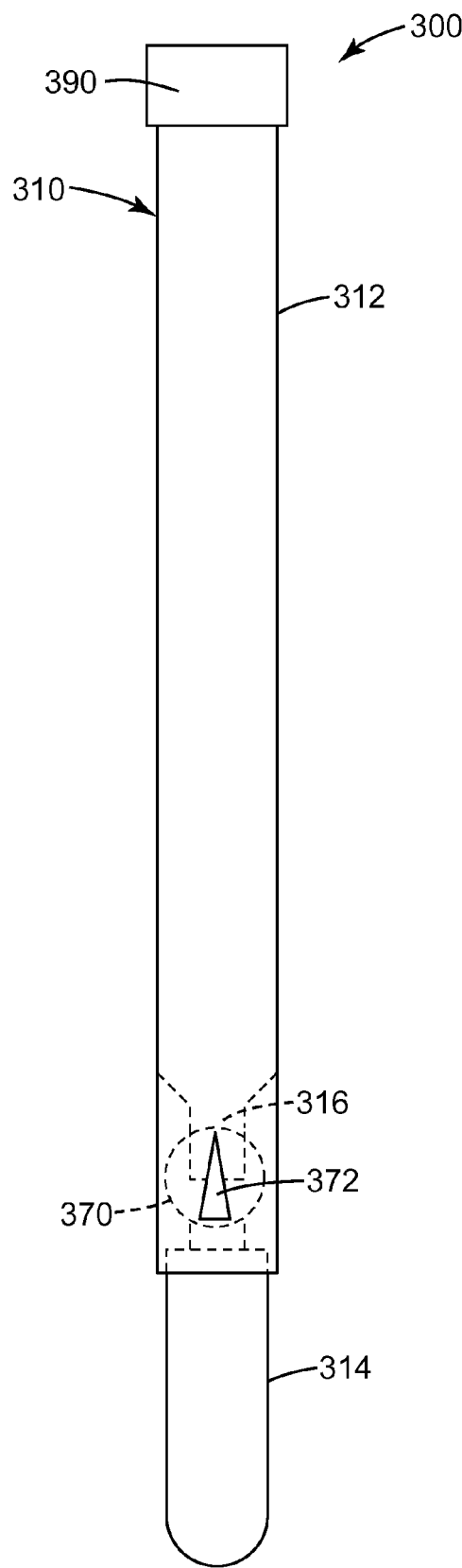
FIG. 3A shows a front view of one embodiment of a sample preparation and detection device comprising a housing and a valve, according to the present disclosure.
Figure 3B:
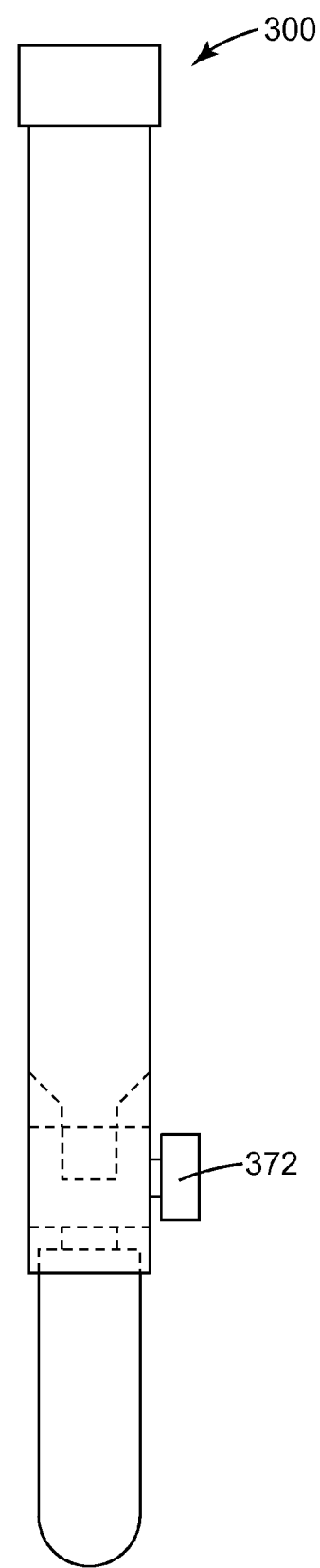
FIG. 3B shows a side view of the device of FIG. 3A.

FIG. 3A shows a front view of one embodiment of a detection device 300 according to the present disclosure. The device 300 includes a housing 310 and an optional cap 378. The housing 310 can be constructed as described above with an upper part 312, a passageway 316, and a lower part 314. The optional cap 378 can be constructed as described above. The device 300 also includes a dead-end valve 370 with a valve actuator 372, which is shown in a first position in FIG. 3A. FIG. 3B shows a side view of the device 300 and valve actuator 372 of FIG. 3A.

Figures 3C, 3D:
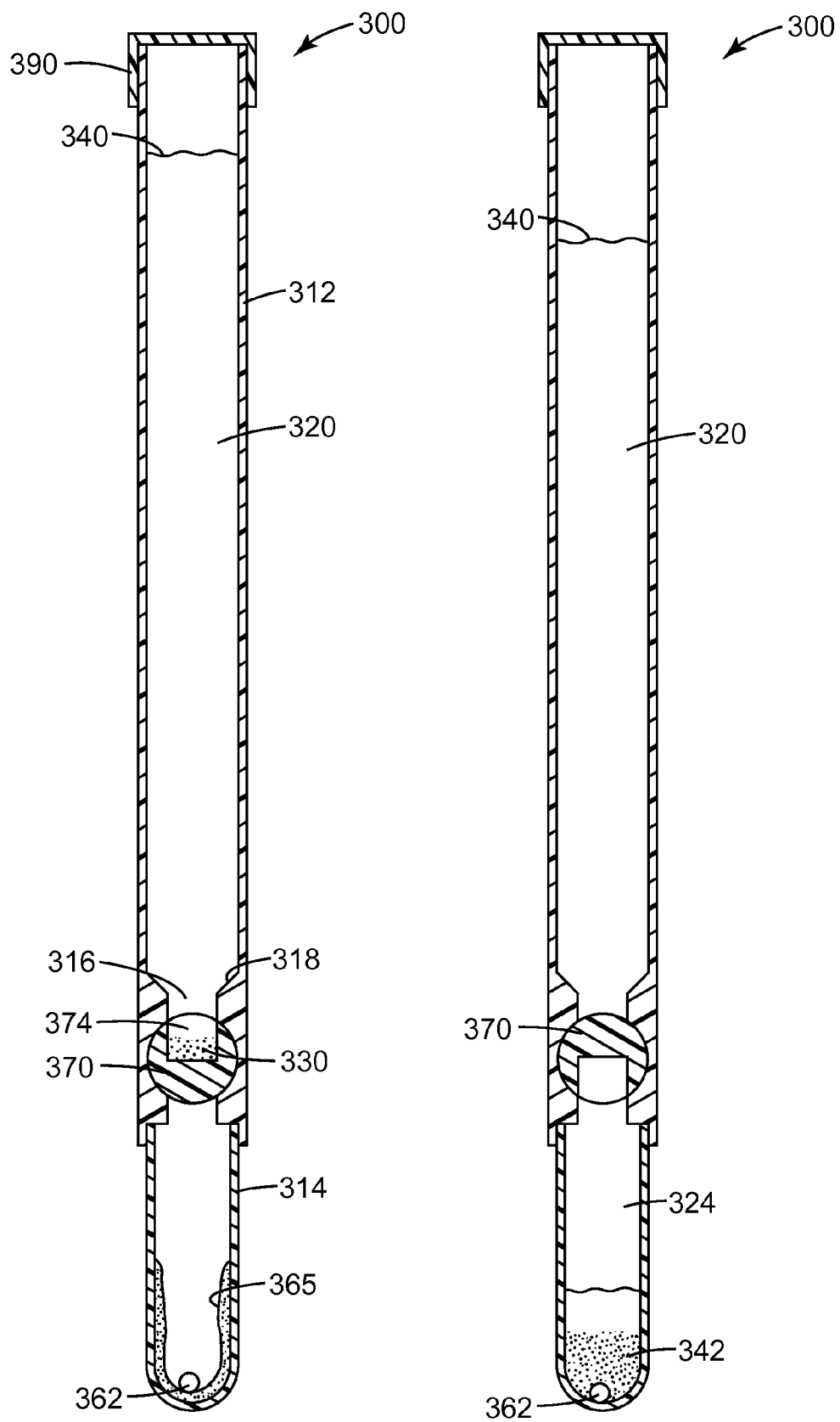
FIG. 3C shows a cross-sectional view of the device of FIG. 3A with a liquid sample and a cell concentration agent disposed in a first receptacle of the housing and the valve in a first position.
FIG. 3D shows a cross-sectional view of the device of FIG. 3C with the valve in a second position and the cell concentration agent transferred to the second receptacle of the housing.

FIG. 3C show a cross-sectional view of the device 300 shown in FIG. 3A. The device 300 comprises a cap 378 and a housing 310. The housing 310 includes an upper part 312 and lower part 314. The upper part 312 includes a passageway 316 in which a dead-end valve 370 is positioned. The dead-end valve 370 includes a valve cavity 374 which, when the valve is in this first position, is in fluid communication with the first receptacle 320. The valve cavity 374 includes an optional cell concentration agent 330, which contacts a liquid sample 340 in the first receptacle 320. The second receptacle 324 contains an optional release element 362 and/or optional detection reagent 365, both as described herein. Also shown in FIG. 3C is optional taper region 318, as described herein.

FIG. 3D shows a cross-sectional view of the device 300 from FIG. 3C with the valve 370 in a second position. When the valve 370 is in the second position, a portion 342 of the liquid sample, containing the cell concentration agent 330, is isolated and transferred to the second receptacle 324 where the portion 342 can contact the release element 362, if present, and can interact with the detection reagent 365, if present, as described herein.

It is recognized that the dimensions of the valve cavity 374 can constitute a known predetermined volume and that, as such, the valve 370 can be used one or more times to transfer a predetermined amount of the liquid sample 340 from the first receptacle 320 to the second receptacle 324. Furthermore, it is recognized that, after the portion 342 of the liquid sample has been transferred from the first receptacle 320 to the second receptacle 324, the remainder of the liquid sample 340 in the first receptacle 320 could be discarded and a different material (e.g., a diluent, a buffer, a liquid and/or powder reagent) can be placed into the first receptacle 320 and a predetermined amount could subsequently be transferred to the second receptacle 324 using the valve 370 (not shown).

In the illustrated embodiment of FIG. 3, the means for isolating the first receptacle 320 and second receptacle 324 of the housing includes the valve 370. In the illustrated embodiment of FIG. 3, the means for transferring the cell concentration agent 330 from the first receptacle 320 to the second receptacle 324 includes the passageway 316 and the valve 370.

Figure 4A:
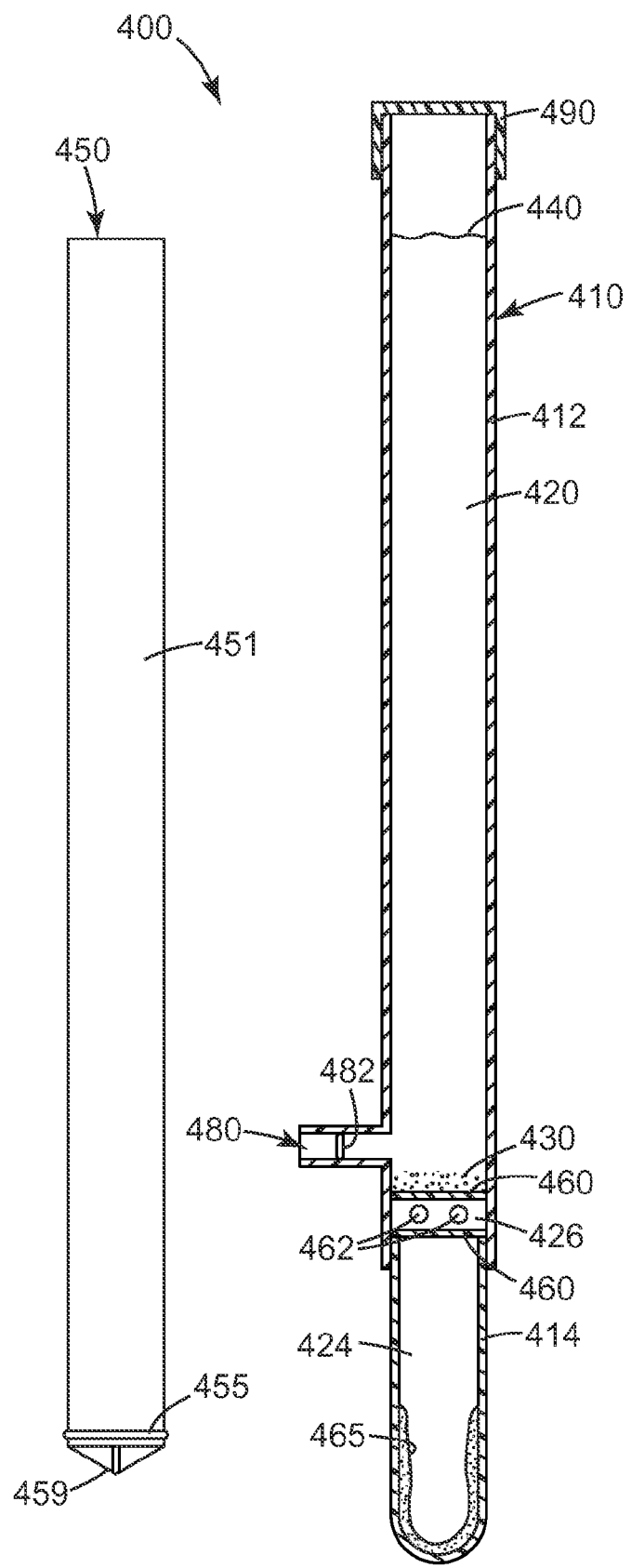
FIG. 4A shows a cross-sectional view of one embodiment of a housing comprising two receptacles and a drain valve and a side view of a plunger, which are both components of a sample preparation and detection device.

FIG. 4A shows a side view of a plunger 450 and a cross-sectional view of a housing 410, both of which are components of a detection device 400 according to the present disclosure. The plunger comprises a shaft 451, optional O-ring 455, and piercing end 459. The O-ring can be made of a conformable material (e.g., butyl rubber) to provide a liquid-tight seal with the housing 410. The housing 410 can be constructed as described above with an upper part 412 and a lower part 414. The optional cap 478 can be constructed as described above. Frangible seals 460 divide the housing 410 into three receptacles, a first receptacle 420, second receptacle 424, and third receptacle 426 that is disposed between the first receptacle 420 and second receptacle 424. In this illustration, frangible seals 460 are located at the end of the first receptacle 420 that is proximate the second receptacle 424. The space between the frangible seals 460 defines a third receptacle 426. Located in the third receptacle 426 is a release element 462 comprising a cell extractant. An alternative construction (not shown) may have only one frangible seal 460 proximate the second receptacle 424, with the release element 462 located in the second receptacle 424, as shown in FIG. 3C.

Located in the first receptacle 420 proximate frangible seals 460 is a drain valve 480 with the valve gate 482, which is shown in the closed position. Also located in the first receptacle 420 is the liquid sample 440 and the optional cell concentration agent 430. An optional detection reagent 465 is shown in the second receptacle 424.

Figures 4B, 4C, 4D:
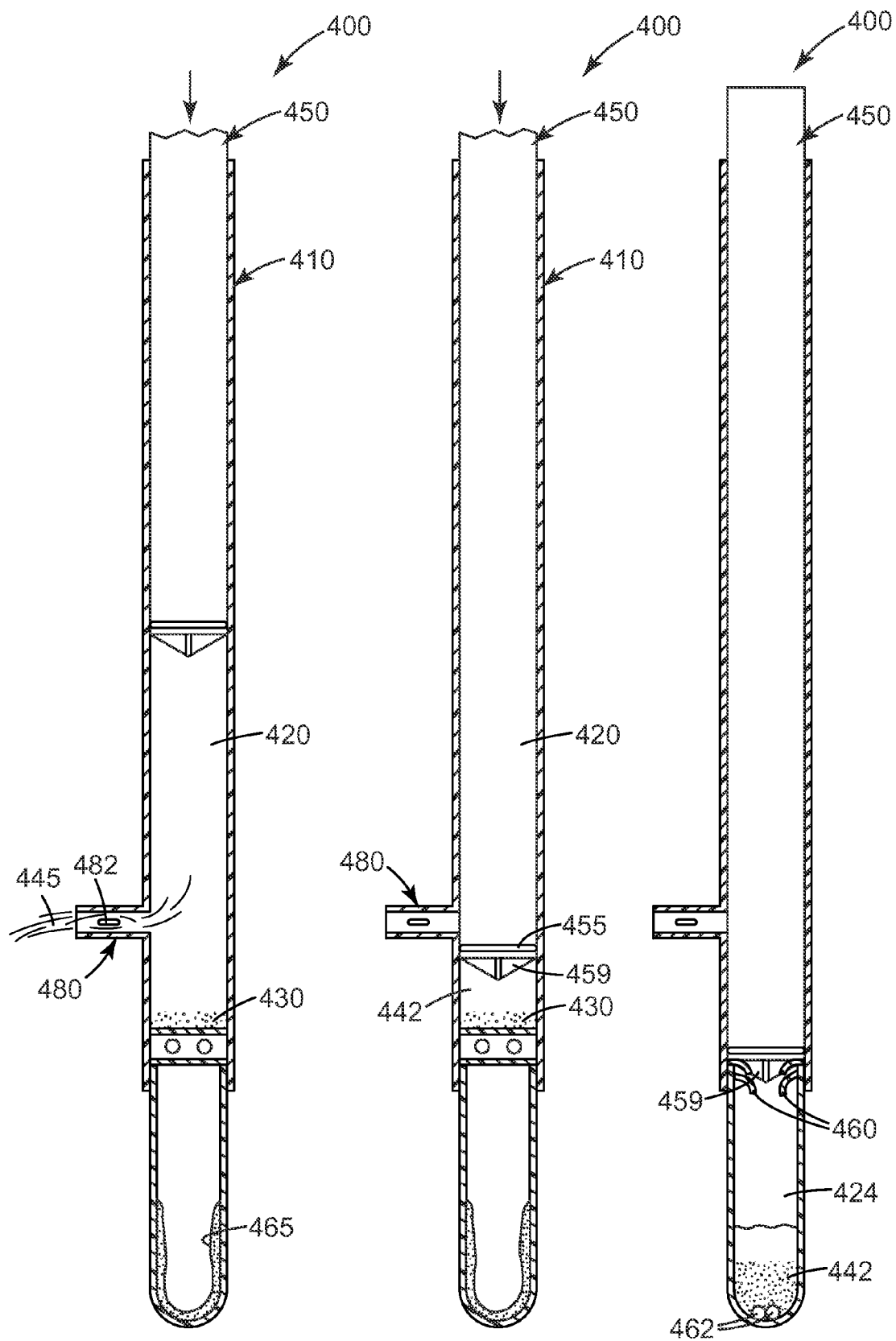
FIG. 4B shows a cross-sectional view of the assembled device of FIG. 4A with the drain valve in an open configuration and the plunger disposed in a first position in the housing.
FIG. 4C shows a cross-sectional view of the assembled device of FIG. 4B with the plunger disposed in a second position in the housing and the cell concentration agent transferred to the second receptacle of the housing.
FIG. 4D shows a cross-sectional view of the device of FIG. 4C, wherein the plunger has punctured the frangible seals and transferred the cell concentration agent to the second receptacle.

FIG. 4B shows a cross-sectional view of an assembled detection device 400 comprising the housing 410 and plunger 450 of FIG. 4A. The cell concentration agent 430 is settled to the bottom of the first receptacle 420. The valve gate 482 of the drain valve 480 is in the open position and, as force is applied (e.g., by pressure from finger or hand) in the direction shown by the arrow, the clarified liquid sample 445 is expelled out of the drain valve 480. Also shown in FIG. 4B is detection reagent 465 coated on the wall of the second receptacle 424.

FIG. 4C shows a cross-sectional view of the detection device 400 of FIG. 4B. In this view, the O-ring 455 and piercing end 459 of the plunger 450 are inserted in the housing 410 on the side of the drain valve 480 proximate the nearest frangible seal 460. In this position, the plunger 450 traps a portion 442 of the liquid sample comprising the cell concentration agent 430 between the plunger 450 and the nearest frangible seal 460.

FIG. 4D shows a cross-sectional view of the detection device 400 of FIG. 4C. In this view, the piercing end 459 of the plunger 450 has punctured both frangible seals 460 and the portion 442 of the liquid sample has transferred to the second receptacle 424, where it has dissolved the detection reagent (shown in FIG. 4C) and the portion 442 is in contact with the release element 462 comprising a cell extractant.

Figure 5A:
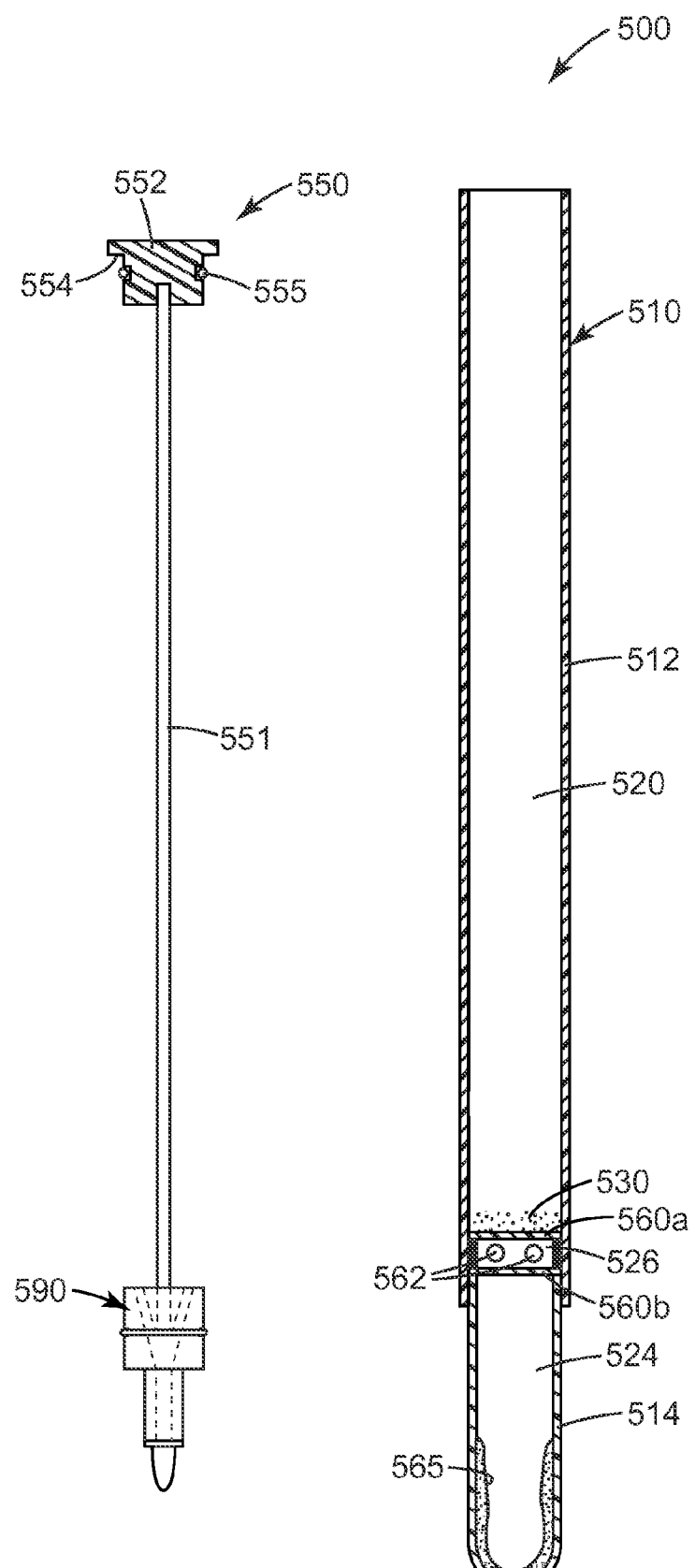
FIG. 5A shows a cross-sectional view of one embodiment of a housing and a side view of a plunger, partially in section, which are both components of one embodiment of a sample preparation and detection device according to the present disclosure.

FIG. 5A shows a cross-sectional view of a plunger 550 and a housing 510, both of which are components of a detection device 500. The plunger 550 comprises a shaft 551 with an optional handle 552 and a tip 590. In any embodiment, the handle 552 further may comprise an optional O-ring 555.

The housing 510 can be constructed as described above, with an upper part 512 and a lower part 514. Frangible seals 560a and 560b divide the housing 510 into three receptacles, a first receptacle 520, second receptacle 524, and third receptacle 526 that is disposed between the first receptacle 520 and second receptacle 524. In this illustration, frangible seals 560a and 560b are located at the end of the first receptacle 520 that is proximate the second receptacle 524. The space between the frangible seals 560a and 560b defines the third receptacle 526. Located in the third receptacle 526 is release element 562, which comprises a cell extractant as described herein. In the illustrated embodiment, the second receptacle 524 comprises an optional detection reagent 565. An alternative construction (not shown) may have only one frangible seal proximate the second receptacle, with the release element located in the second receptacle, as shown in FIG. 3C.

The handle 552 can be made, using processes well known in the art, from a variety of materials including, for example, plastic, wood, metal, and combinations thereof. The optional O-ring 555 is disposed in a notch 554 in the handle 552. The handle 552 may be shaped and dimensioned such that at least a portion of the handle 552 can be inserted into the housing 510 when the plunger 550 is fully inserted in the housing 510. In one embodiment, the handle 552 further includes a rim 554 that engages the opening of the housing 510 to prevent the handle 552 from being fully inserted into the housing 510.

The shaft 551 of the plunger 550 can be made from a variety of materials including, for example, plastic, wood, metal, and combinations thereof. One end of the shaft 551 is coupled to the handle 552 by press-fitting into a recessed portion (as shown in FIG. 5), by ultrasonic welding, or by using an adhesive, for example. The other end of the shaft 551 is coupled to the tip 590 by press-fitting, by ultrasonic welding, or by using an adhesive, for example.

Figures 6A, 6B:
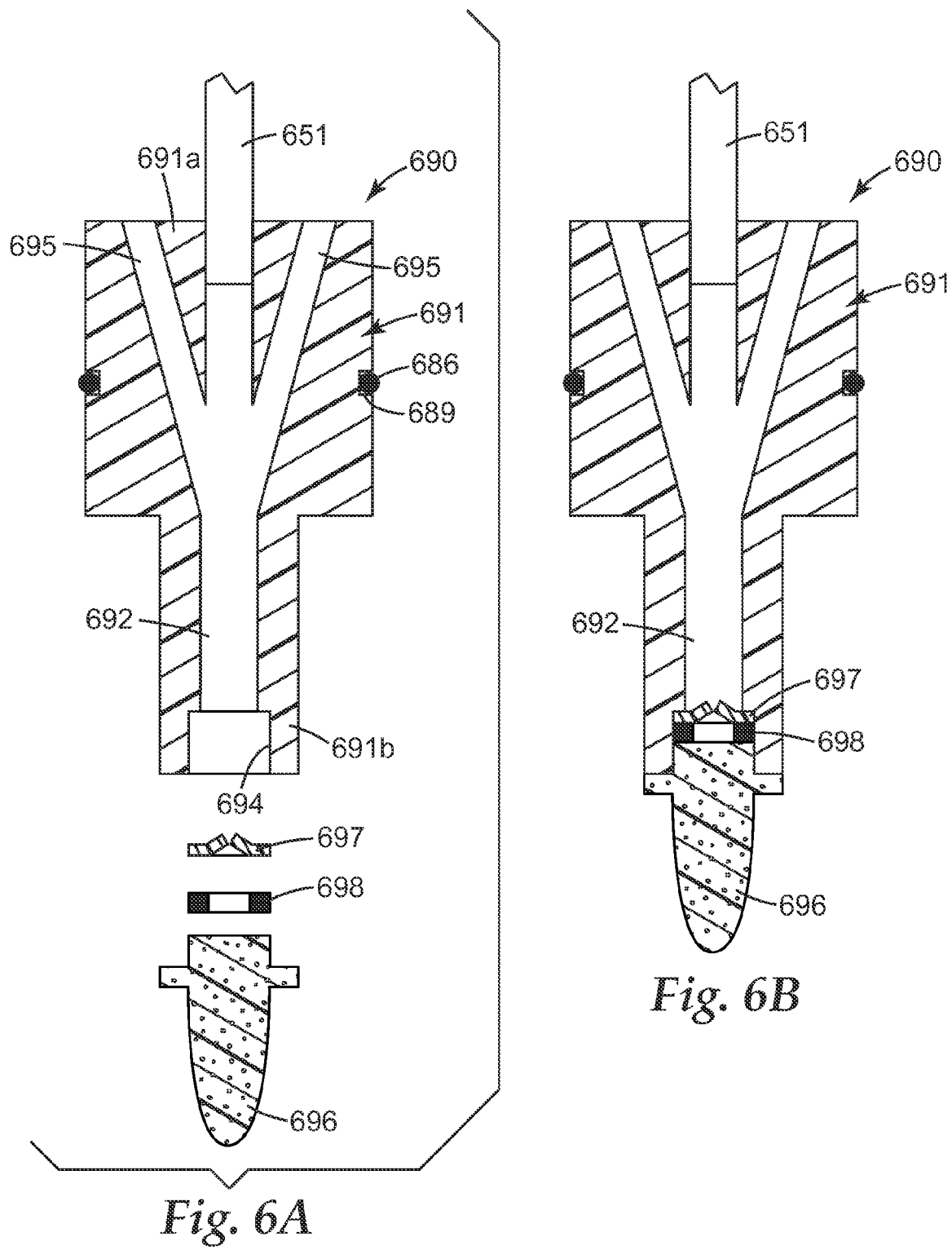
FIG. 6A shows an exploded side view, partially in section, of the tip of the plunger of FIG. 5A.
FIG. 6B shows a side view, partially in section, of the assembled tip of FIG. 6A.

Detail of the tip 590 of the plunger 550 is shown in FIGS. 6A and 6B.

FIG. 6A shows a partially exploded side view, partially in section, of the tip 590 of FIG. 5A. The tip 690 comprises a body 691, a one-way valve 697, and a filter 696.

The body 691 includes a first end 691a, a second end 691b, and a conduit 692 running through the body 691 from the first end 691a to the second end 691b. At the first end 691a, the conduit 692 is sealed by the shaft 651 of the plunger. At the second end 691b, the conduit 692 opens into a recessed opening 694. Two drain channels 695 run from the first end 691a of the body 691 to the conduit 692. Thus, the drain channels are fluidically connected to the conduit 692 and the recessed opening 694. Furthermore, the recessed opening 694, conduit 692 and drain channels 695 for a fluid pathway through the tip 690 of the plunger. Thus, in this embodiment, the plunger comprises a fluid pathway.

In one embodiment (not shown), the tip 690 may comprise only one drain channel 695. Advantageously, a plurality of drain channels 695 may provide less back-pressure and, thus, a higher rate of fluid transport through the tip 690.

The body 691 may be fabricated from plastic (e.g., polypropylene, polyethylene, polytetrafluoroethylene) by molding, for example. The body 691 is shaped and dimensioned to fit in a housing (e.g., housing 510 of FIG. 5A). In any embodiment, the body 691 or the O-ring 686 can form a substantially liquid-tight seal with the walls of a housing when the body 691 is inserted into the housing. In any embodiment that includes an O-ring, 686, the O-ring 686 may function both to form a liquid-tight seal and to wipe particulate material (e.g., cell concentration agents) off the wall of the housing as the O-ring 686 is moved in relation to the wall of the housing. The shaft 651 may be coupled to the conduit 692 by means that are known in the art (e.g., by an adhesive, by press-fit). The optional O-ring 686 is disposed in a notch 689 in the body 691.

The tip 690 further comprises a filter 696. The filter 696 is coupled to the body 691. In the illustrated embodiment, the filter 696 is formed from a porous material, which can be press-fit and/or adhesively coupled to the recessed opening 694. In some embodiments, the porous material can be semi-rigid porous material (e.g., POREX filtration medium sold under the part number X6854 by Porex Corporation, Fairburn, Ga.). The filter 696 may be configured with a relatively angular or pointed end, such that the end can facilitate the penetration of a frangible seal. In alternative embodiments (not shown), the filter may comprise a membrane filter that is coupled to the body. When coupled to the body, the membrane filter is part of a fluid path that includes the conduit and a drain channel.

In some embodiments, the porosity of the filter 696 may be selected such that the filter 696 prevents only the passage of relatively large particles (e.g., >1 μm, >5 μm, or >10 μm) through it. Relatively large particles may include, for example, cell concentration agents as described herein. In these embodiments, microorganisms such as bacteria, yeast, and/or filamentous fungi (mold) may pass through the filter 696.

In some embodiments, the porosity of the filter 696 may be selected such that the filter 696 prevents only the passage of relatively small particles (e.g., <1 μm, <0.45 μm, <0.2 μm) through it. In these embodiments, microorganisms such as bacteria, yeast, and/or filamentous fungi (mold) may be retained by the filter 696.

The tip 690 further comprises a one-way valve 697 disposed in the recessed opening 694 between the filter 696 and the conduit 692. Also shown is an optional retaining washer 698 that serves to hold the one-way valve 697 in position. The one-way valve 697 may be constructed from plastic (e.g., polypropylene, polyethylene, polyester) or rubber, for example, and may be configured as a duck-bill valve, for example. In use, the one-way valve 697 substantially prevents the flow of liquid that has passed through the filter 696 from returning through the filter 696 in the opposite direction.

FIG. 6B shows a side view, partially in section of the assembled tip 690 of FIG. 6A. The one-way valve 697, optional retaining washer 698, and filter 696 are disposed in the recessed opening and are in fluidic connection with the conduit 692 and the drain channels 695. The shaft 651 is coupled to the body 691 of the tip 690.

Referring back to FIG. 5A, the detection device 500 comprising the housing 510 and plunger 550 is used in a method to detect microorganisms and, in particular, live microorganisms.

In use, a liquid sample is transferred into the first receptacle 520 of the housing 510, where it is allowed to contact a cell concentration agent 530. After adding the liquid sample 540 to the housing 510, the tip of the plunger 550 is inserted into the housing 510 and urged (e.g., manually or mechanically) toward the second receptacle 524 of the housing 510, as shown in FIG. 5B. As the tip 591 of the plunger 550 contacts the liquid sample 540, the liquid passes through the tip 590 and back into the housing 510, as shown in FIG. 5B. This process retains the cell concentration agent 530 and, in some embodiments, free microorganisms in a portion 542 of the liquid sample proximate the third receptacle 526.

As the tip 590 of the plunger 550 penetrates the frangible seal 560a, not shown, the portion 542 of the liquid sample containing the cell concentration agent 530 contacts the release element 562. Further movement of the plunger 550 (as shown in FIG. 5D) causes penetration of the frangible seal 560b, which causes the portion 542 of the liquid sample and the release element 562 to transfer to the second receptacle 524, where they contact the detection reagent 565.

Figure 7A:
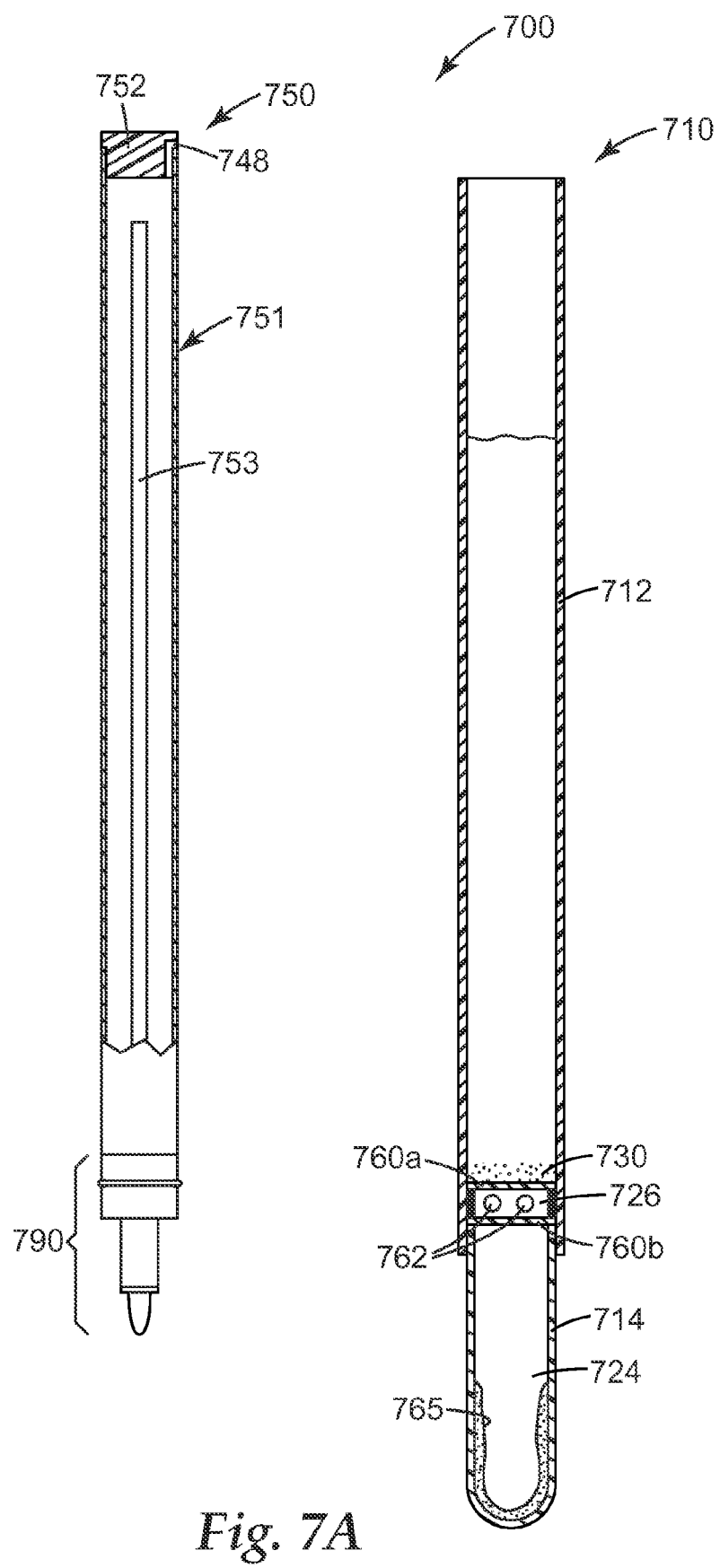
FIG. 7A shows a cross-sectional view of one embodiment of a housing and a side view of a hollow plunger, partially in section, which are both components of one embodiment of a sample preparation and detection device according to the present disclosure.

FIG. 7A shows a cross-sectional side view of another embodiment of a detection device 700 according to the present disclosure. The detection device 700 comprises a plunger 750 and a housing 610.

The housing 710 can be constructed as described above with an upper part 712 and a lower part 714. Frangible seals 760a and 760b divide the housing 710 into three receptacles, an first receptacle 720, second receptacle 724, and third receptacle 726 that is disposed between the first receptacle 720 and second receptacle 724. In this illustration, frangible seals 760a and 760b are located at the end of the first receptacle 720 that is proximate the second receptacle 724. The space between the frangible seals 760a and 760b defines a third receptacle 726. Located in the third receptacle 726 is a release element 762 comprising a cell extractant. In the illustrated embodiment, the second receptacle 724 comprises an optional detection reagent 765. An alternative construction (not shown) may have only one frangible seal 760 proximate the second receptacle 724, with the release element 762 located in the second receptacle 724, as shown in FIG. 3C.

The plunger 750 comprises a shaft 751 coupled to a handle 752 and a tip 790. In this embodiment, the shaft 751 is hollow and the handle comprises a vent 748 to equalize the pressure between the interior and exterior of the shaft 751. The plunger further comprises an optional drain tube 753. The drain tube 753 receives liquid filtrate from the tip 790 and distributes the filtrate to the interior of the shaft 751. By functioning as an overflow valve, the drain tube 753 also reduces the volume of filtrate that can flow back through the tip 790 in the reverse direction.

Detail of the tip 790 of the plunger 750 is shown in FIG. 8.

FIG. 8A shows a partially exploded side view, partially in section, of the tip 790 of FIG. 7A. The tip 890 comprises a body 891, an optional one-way valve 897, and a filter 896. Also show in FIG. 8A is a portion of the plunger 850 comprising a hollow shaft 851 and a drain tube 853.

The body 891 includes a first end 891a, a second end 891b, and a conduit 892 running through the body 891 from the first end 891a to the second end 891b. At the first end 891a, the conduit 892 is coupled (e.g., by press-fit, and adhesive, or by a threaded connection) to the drain tube 853 of the plunger. At the second end 891b, the conduit 892 opens into a recessed opening 894. Thus, the recessed opening 894 is fluidically connected to the conduit 892 and the drain tube 853.

The body 891 may be fabricated from plastic (e.g., polypropylene, polyethylene, polytetrafluoroethylene) by molding, for example. The body 891 is shaped and dimensioned to fit in a housing (e.g., housing 710 of FIG. 7A). In any embodiment, the body 891 or the O-ring 886 can form a substantially liquid-tight seal with the walls of a housing when the body 891 is inserted into the housing. In any embodiment that includes an O-ring, 886, the O-ring 886 may function both to form a liquid-tight seal and to wipe particulate material (e.g., cell concentration agents) off the wall of the housing as the O-ring 886 is moved in relation to the wall of the housing. The shaft 851 may be coupled to the conduit 892 by means that are known in the art (e.g., by an adhesive, by press-fit). The optional O-ring 886 is disposed in a notch 889 in the body 891.

The tip 890 further comprises a filter 896. The filter 896 is coupled to the body 891 at the recessed opening 894. In the illustrated embodiment, the filter 896 is formed from a porous material, which can be press-fit and/or adhesively coupled to the recessed opening 894. In some embodiments, the porous material can be semi-rigid porous material (e.g., POREX filtration medium sold under the part number X6854 by Porex Corporation, Fairburn, Ga.). The filter 896 may be configured with a relatively angular or pointed end, such that the end can facilitate the penetration of a frangible seal. In alternative embodiments (not shown), the filter may comprise a membrane filter that is coupled to the body. When coupled to the body, the membrane filter is part of a fluid path that includes the conduit and a drain channel.

In some embodiments, the porosity of the filter 896 may be selected such that the filter 896 prevents only the passage of relatively large particles (e.g., >1 μm, >5 μm, or >10 μm) through it. Relatively large particles may include, for example, cell concentration agents as described herein. In these embodiments, microorganisms such as bacteria, yeast, and/or filamentous fungi (mold) may pass through the filter 896.

In some embodiments, the porosity of the filter 896 may be selected such that the filter 896 prevents only the passage of relatively small particles (e.g., <1 μm, <0.45 μm, <0.2 μm) through it. In these embodiments, microorganisms such as bacteria, yeast, and/or filamentous fungi (mold) may be retained by the filter 896.

The tip 890 may further comprise an optional one-way valve 897 disposed in the recessed opening 894 between the filter 896 and the conduit 892. Also shown is an optional retaining washer 898 that can serve to hold the one-way valve 897 in position. The one-way valve 897 may be constructed from plastic (e.g., polypropylene, polyethylene, polyester) or rubber, for example, and may be configured as a duck-bill valve, for example. In use, the one-way valve 897 substantially prevents the flow of liquid that has passed through the filter 896 from returning through the filter 896 in the opposite direction.

FIG. 8B shows a side view, partially in section of the assembled tip 790 of FIG. 7A. The one-way valve 897, optional retaining washer 898, and filter 896 are disposed in the recessed opening and are in fluidic connection with the conduit 892 and the drain tube 853. The shaft 851 is coupled to the body 891 of the tip 890.

Referring back to FIG. 7A, the detection device 700 comprising the housing 710 and plunger 750 is used in a method to detect microorganisms and, in particular, live microorganisms.

Figure 7B:
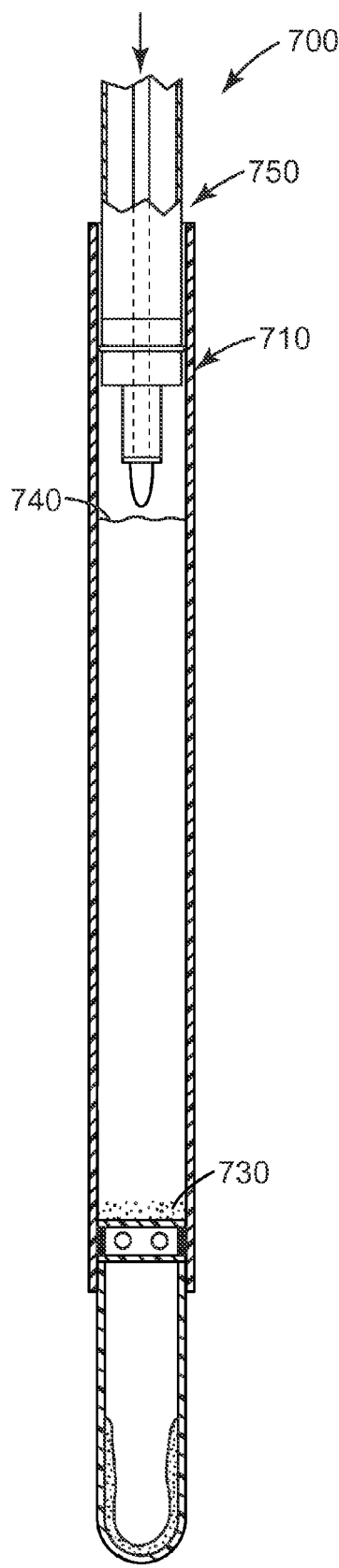
FIGS. 7B-7D show a cross-sectional views of the assembled device of FIG. 7A with the plunger inserted to various depths into the housing.
Figure 7C:
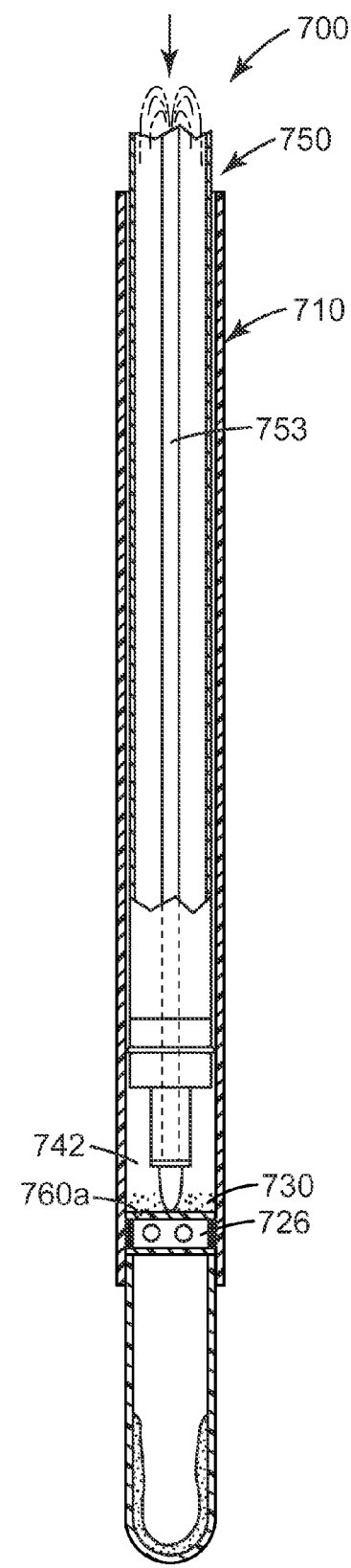

In use, a liquid sample is transferred into the first receptacle 720 of the housing 710, where it is allowed to contact a cell concentration agent 730. After adding the liquid sample 740 to the housing 710, the tip 790 of the plunger 750 is inserted into the housing 710 and urged (e.g., manually or mechanically) toward the second receptacle 724 of the housing 710, as shown in FIG. 7B. As the tip 791 of the plunger 750 contacts the liquid sample 740, the liquid passes through the tip 790, through the drain tube 753, and into the hollow shaft of the plunger 750, as shown in FIG. 7B. This process retains the cell concentration agent 730 and, in some embodiments, free microorganisms in a portion 742 of the liquid sample proximate the third receptacle 726.

Figure 7D:
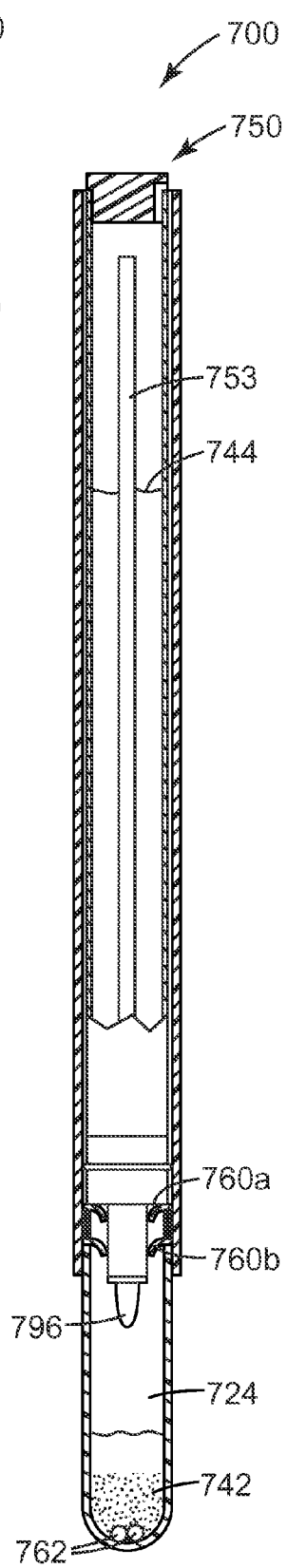

As the tip 790 of the plunger 750 penetrates the frangible seal 760a, not shown, the portion 742 of the liquid sample containing the cell concentration agent 730 contacts the release element 762. Further movement of the plunger 750 (as shown in FIG. 7D) causes penetration of the frangible seal 760b, which causes the portion 742 of the liquid sample and the release element 762 to transfer to the second receptacle 724, where they contact the detection reagent 765.

Figure 9:
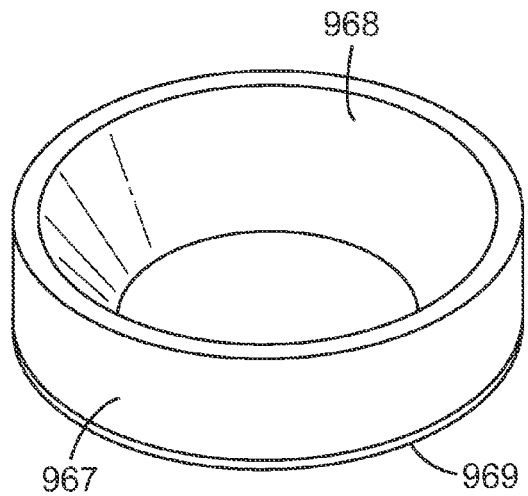
FIG. 9 shows one embodiment of a cell concentration agent collector according to the present disclosure.

Devices of the present disclosure include frangible seals in a housing. The frangible seals are pierced to transport the cell concentration agent from one compartment of the device to another compartment. In some embodiments, the amount cell concentration agent transferred in that process can be enhanced by collecting the cell concentration agent onto a relatively area of the frangible seal. FIG. 9 shows one embodiment of a collector 967 to enhance the recovery of cell concentration agent. The collector 967 is dimensioned to fit within the housing of a detection device according to the present disclosure. The collector 967 comprises a beveled edge 968 that is oriented toward the sample comprising a cell concentration agent (not shown). Typically, the beveled edge 968 faces upward such that it collects particles that are settling by the force of gravity. Alternatively, the beveled edge 968 could be oriented toward a centrifugal or a hydrodynamic force, for example, to collect particles subjected to forces other than gravity. The collector 967 further comprises an optional frangible seal 969.

The collector 967 can be fabricated from a variety of materials including, for example a polymer (e.g., polyester, polypropylene, polytetrafluoroethylene, polypropylene, polystyrene, nylon, and combinations and derivatives thereof), glass, and metal. The collector 967 may further comprise a lubricious coating to resist the adherence of particles to its surface. The beveled edge 968 may be angled (e.g. a 45-degree angle, a >45-degree angle) to facilitate the movement of particles down its slope. The frangible seal 969 is fabricated as described herein and may be coupled to the collector 967 by means that are described herein.

Figure 10B:
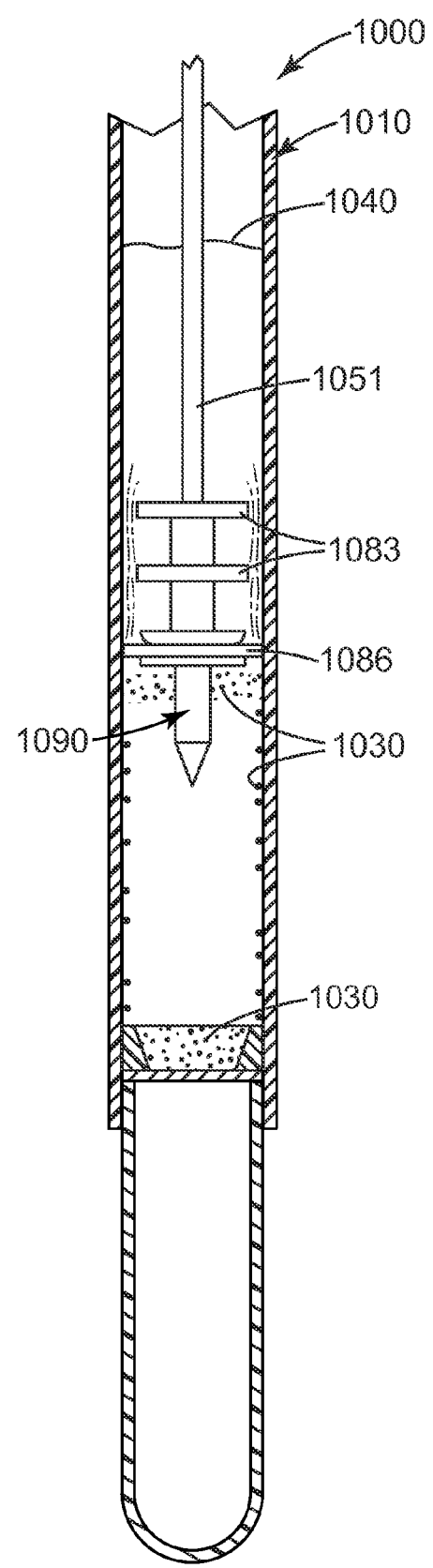
FIG. 10B shows a side view, partially in section, of the assembled device of FIG. 10A.
Figure 10A:
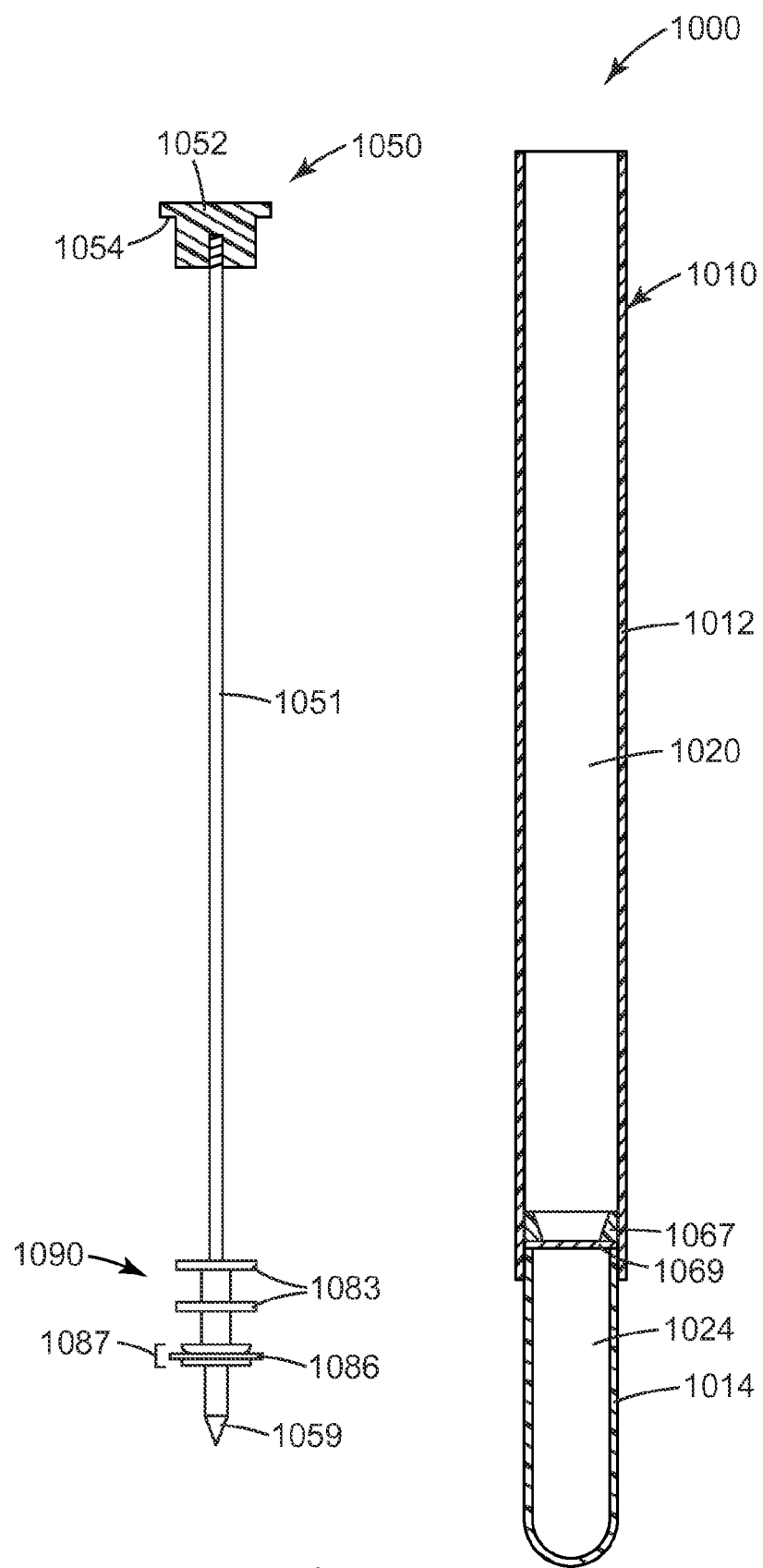
FIG. 10A shows a cross-sectional view of one embodiment of a housing and a side view of a plunger, partially in section, which are both components of one embodiment of a sample preparation and detection device according to the present disclosure.

FIG. 10A shows one embodiment of a detection device 1000 comprising a collector 1067. The device 1000 comprises a housing 1010 and a plunger 1050. The housing 1010 comprises an upper part 1012 and a lower part 1014. Disposed within the upper part 1012 and proximate the lower part 1014 is a collector 1067 with a frangible seal 1069 coupled thereto. The frangible seal 1069 is coupled to the side of the collector 1067 that is facing the lower part 1014. Thus, the frangible seal 1069 divides the housing 1010 into two isolated receptacles, an first receptacle 1020 and a second receptacle 1024.

The plunger 1050 comprises a handle 1052, a shaft 1051, and a tip 1090. The handle 1052 can be constructed as described above and may comprise an optional rim 1054 that engages the housing 1010 to prevent the plunger 1050 from being inserted too far into the housing 1010. The handle 1052 can be coupled to the shaft 1051 via a threaded fit or by other coupling means (e.g., press-fit, adhesive). The tip 1090 may be fabricated fusing processes and materials described for other tip embodiments described herein. The tip 1090 may comprise one or more guides 1083. The guides are dimensioned to loosely fit within the interior of the housing 1010 and function to reduce lateral movement of the tip 1090 as the tip 1090 moves longitudinally through the housing 1010.

The tip 1090 further comprises a scraper 1086, which is held in a fixed position on the tip 1090. In the illustrated embodiment, the scraper 1086 is held in a fixed position by retaining member 1087. The retaining member 1087 can be molded or machined as part of the tip 1090 or it can comprise a bracket or plurality of brackets coupled to the tip 1090. Alternatively, the scraper 1086 may be directly coupled (e.g., adhesively coupled) to the tip 1090.

The scraper 1086 is disc-shaped and is dimensioned to form a relatively tight fit inside the housing 1010. In some embodiments, the scraper can comprise an-O-ring. The scraper 1086 should substantially maintain its shape when immersed in an aqueous liquid. Although the scraper should be dimensioned to form a relatively tight fit inside the housing, the scraper should be relatively flexible to permit fluid to flow around its edge as the plunger is pushed through a liquid sample in the housing 1010. Suitable materials for fabricating the scraper 1086 include, for example polyurethane rubber.

In use, a liquid sample 1040 and a cell concentration agent 1030 are contacted in the housing 1010 of the device, as shown in FIG. 10B. The plunger 1050 is inserted into the housing 1010 and the tip 1090 of the plunger 1050 is urged toward the bottom of the housing 1010. As the tip 1090 passes through the liquid sample 1040, the cell concentration agent 1030 is urged toward the bottom of the housing 1010 by the scraper 1086, while the liquid sample 1040 flows around the edge of the scraper 1086. Advantageously, this devices allows the user to collect and concentrate the cell concentration agent 1030 in a substantially shorter period of time than possible if the cell concentration agent 1030 is allowed to settle by gravity force to the bottom of the housing 1010. Furthermore, the flexible scraper facilitates collecting a portion of cell concentration agent 1030 that might otherwise adhere to the walls of the housing. Thus, the inventive device 1000 increases the recovery of the cell concentration agent and, thereby, increases the sensitivity of a method that uses a cell concentration agent to concentrate microorganisms.

It should be recognized that, in a sample preparation and detection device in which the cell concentration agent comprises ferromagnetic materials (e.g., particles), that a magnet or an electromagnet can be positioned adjacent the device to draw the particles (and microorganisms coupled thereto) to a desired location for collecting the particles and/or transferring them to another receptacle. In some embodiments, the magnet can be positioned adjacent the device (e.g., adjacent the bottom of the device) after a sufficient period of time to allow for the cell concentration agent to couple substantially all of the microorganisms in the liquid sample.

Methods of Detecting Biological Analytes from Live Cells:

Methods of the present disclosure include methods for the detection of biological analytes that are released from live cells including, for example, live microorganisms, after exposure to an effective amount of cell extractant.

Methods of the present disclosure include the formation of a liquid mixture comprising a sample and a release element comprising a cell extractant. Methods of the present disclosure further include detecting a biological analyte. Detecting a biological analyte can further comprise quantitating the amount of biological analyte in the sample.

In one aspect, the present disclosure provides a method of detecting cells in a sample. The method comprises providing a cell concentration agent, a release element comprising a cell extractant and a liquid sample. Suitable cell concentration agents are described in U.S. Patent Application Publication No. US 2010/0190171, and entitled "MICROORGANISM CONCENTRATION PROCESS", which is incorporated herein by reference in its entirety.

The method further comprises contacting the liquid sample and the cell concentration agent for a period of time. The cell concentration agent can comprise particles, fibers, a matrix (e.g., a fibrous matrix) comprising particles, or any combination of two or more of the foregoing. The cell concentration agent can be suspended in the liquid sample during the contact period. The suspension can be placed into a vessel, such as a tube, a flask, a beaker, or any of the detection devices described herein. In certain preferred embodiments, the liquid sample is mixed with the cell concentration agent for a period of time by, for example, stirring, vortexing, or vibrating the suspension. While the cell concentration agent is contacted with the liquid sample, cells from the liquid sample are coupled to the cell concentration agent.

The method further comprises isolating the cell concentration agent from at least a portion of the liquid sample. During this process, the cell concentration agent may be concentrated in a smaller volume than the original liquid sample. The cell concentration agent can be isolated from at least a portion of the liquid sample by a variety of means. For example, if the cell concentration agent has a higher specific gravity than the liquid sample, the cell concentration agent can settle to the bottom of the suspension. At least a portion of the liquid sample can be removed (e.g., by pipetting or decanting). Alternatively, or additionally, at least a portion of the liquid sample can be removed by centrifugation or filtration.

A filter can be described by its pore size (for example by its bubble point pore size). The bubble point pore size of a filter is generally the average of the largest size of the pores of the filter. In some embodiments, the filter can have an average pore size that is less than the average size of the cell concentration agent. The ability to utilize filters having these relatively large pore sizes offers significant advantages to methods as disclosed herein when compared with other methods for separating microorganisms from samples, such as water samples.

In an embodiment, the filter can have an average pore size that is at least about 1 micrometer (μm) or larger. In an embodiment, the filter can have an average pore size that is at least about 1.5 μm or larger. In an embodiment, the filter can have an average pore size that is at least about 5 μm or larger. In an embodiment, the filter can have an average pore size that is at least about 10 μm or larger. As larger pore size filters are utilized, the sample will be easier and quicker to filter as the back pressure decreases with increase in pore size.

Filtering the sample can be accomplished using known methods. In an embodiment, the method of filtering that is chosen can be dictated at least in part on the particular application of the method. For example, the sample can be filtered using a negative vacuum, by applying a positive pressure, by the force of gravity. The particular technique used to filter the sample can depend at least in part on the type of device that is being utilized to carry out the method. For example, in order to utilize a negative vacuum, the device can be configured with a port that can be or reversibly attached to a source of vacuum; and in order to apply a positive pressure, the device can be configured to allow a user to apply a positive pressure by applying a force with their hands. In an embodiment, the sample can be filtered by applying a positive pressure. Filtering using positive pressure (or using the force of gravity) can offer the advantage of easily being able to carry out the method in the field without the need for any further equipment, such as a vacuum pump.

In some embodiments, a centrifugation step may include the use of a relatively low-speed centrifugation in which the cell concentration agents separate (e.g., by sedimentation) out of the liquid but microorganisms (e.g., bacteria, yeast molds, spore) that are not bound to the cell concentration agent remain suspended in the liquid.

Optionally, the cell concentration agent can be resuspended in a wash solution (e.g., water or a buffer solution) and the cell concentration agent can be isolated from at least a portion of the wash solution. It will be recognized that a washing step can function to remove from the liquid sample contaminating materials that may interfere with a growth and/or detection process.

The method further comprises forming a liquid mixture comprising the isolated cell concentration agent and the release element, wherein the cell extractant is released from the release element. In some embodiments, when the cell concentration agent is isolated from at least a portion of the liquid sample, the cell concentration agent remains in a residual volume of liquid. Additional liquid (e.g., water or a buffer solution) optionally can be added to the cell concentration agent. In the embodiments wherein the cell concentration agent is filtered out of the liquid sample, the cell concentration agent can be resuspended in a volume of liquid (e.g., water or a buffer solution). The liquid suspension comprising the cell concentration agent is contacted with the release element, thereby releasing the cell extractant into the liquid mixture. In methods involving the use of filters to collect the cell concentration agent, the liquid suspension comprising the cell concentration agent can also comprise the filter. An effective amount of cell extractant can be released from the release element to effect the release of biological analytes from cells, if present, in the mixture. The release of an effective amount of cell extractant can occur over a period of time (e.g., up to several seconds, up to several minutes, up to an hour, or longer).

The method further comprises detecting an analyte. The detection of the biological analytes can involve the use of a detection system. Detection systems for certain biological analytes such as a nucleotide (e.g., ATP, NADH, NAD), a polynucleotide (e.g., DNA or RNA) or an enzyme (e.g., NADH dehydrogenase or adenylate kinase) are known in the art and can be used according to the present disclosure. Methods of the present disclosure include known detections systems for detecting a biological analyte. Preferably, the accuracy and sensitivity of the detection system is not significantly reduced by the cell extractant. More preferably, the detection system comprises a homogeneous assay.

In some embodiments, detecting the biological analyte can comprise detecting the analyte directly in a vessel (e.g., a tube, a multi-well plate, and the detection devices described herein) in which the liquid mixture comprising the sample and the release element comprising a cell extractant is formed. In some embodiments, detecting the biological analyte can comprise transferring at least a portion of the liquid mixture to a container other than the vessel in which the liquid mixture comprising the sample and the release element comprising a cell extractant is formed. In some embodiments, detecting the biological analyte may comprise one or more sample preparation processes, such as pH adjustment, dilution, filtration, centrifugation, extraction, and the like.

In some embodiments, the detection system comprises a detection reagent. Detection reagents include, for example, dyes, enzymes, enzyme substrates, binding partners (e.g., an antibody, a monoclonal antibody, a lectin, a receptor), labeled binding partners, and/or cofactors. In some embodiments, the detection reagent comprises a hydrogel, such as the hydrogels comprising an enzyme or enzyme substrate, as described in PCT International Publication No. WO 2010/039627, and entitled "BIODETECTION ARTICLES". In some embodiments, the detection system comprises an instrument. Nonlimiting examples of detection instruments include a spectrophotometer, a luminometer, a plate reader, a thermocycler, an incubator.

Detection systems can include detection instruments. Detection instruments are known in the art and can be used to detect biological analytes colorimetrically (i.e., by the absorbance and/or scattering of light), fluorescently, or lumimetrically. Examples of the detection of biomolecules by luminescence are described by F. Gorus and E. Schram (Applications of bio- and chemiluminescence in the clinical laboratory, 1979, Clin. Chem. 25:512-519).

An example of a biological analyte detection system is an ATP detection system. The ATP detection system can comprise an enzyme (e.g., luciferase) and an enzyme substrate (e.g., luciferin). The ATP detection system can further comprise a luminometer. In some embodiments, the luminometer can comprise a bench top luminometer such as, for example, the FB-12 single tube luminometer (Berthold Detection Systems USA, Oak Ridge, Tenn.). In some embodiments, the luminometer can comprise a handheld luminometer such as, for example, the NG Luminometers, UNG2 or UNG3 available from 3M Company (St. Paul, Minn.).

In some embodiments, the biological analyte is detected at a single time point. In some embodiments, the biological analyte is detected at two or more time points. When the biological analyte is detected at two or more time points, the amount of biological analyte detected at a first time (e.g., before an effective amount of cell extractant is released from a release element to effect the release of biological analytes from live cells in at least a portion of the sample) point can be compared to the amount of biological analyte detected at a second time point (e.g., after an effective amount of cell extractant is released from a release element to effect the release of biological analytes from live cells in at least a portion of the sample). In some embodiments, the measurement of the biological analyte at one or more time points is performed by an instrument with a processor. In certain preferred embodiments, comparing the amount of biological analyte at a first time point with the amount of biological analyte at a second time point is performed by the processor.

For example, the operator measures the amount of biological analyte in the sample after the liquid mixture including the sample and the release element comprising a cell extractant is formed. The amount of biological analyte in this first measurement ($T_1$) can indicate the presence of "free" (i.e. acellular) biological analyte and/or biological analyte from nonviable cells in the sample. In some embodiments, the first measurement can be made immediately (e.g., about 1 second) after the liquid mixture including the sample and the release element comprising a cell extractant is formed. In some embodiments, the first measurement can be at least about 5 seconds, at least about 10 seconds, at least about 20 seconds, at least about 30 seconds, at least about 40 seconds, at least about 60 seconds, at least about 80 seconds, at least about 100 seconds, at least about 120 seconds, at least about 150 seconds, at least about 180 seconds, at least about 240 seconds, at least about 5 minutes, at least about 10 minutes, at least about 20 minutes after the liquid mixture including the sample and the release element comprising a cell extractant is formed. These times are exemplary and include only the time up to that the detection of a biological analyte is initiated. Initiating the detection of a biological analyte may include diluting the sample and/or adding a reagent to inhibit the activity of the cell extractant. It will be recognized that certain detection systems (e.g., nucleic acid amplification or ELISA) can generally take several minutes to several hours to complete.

The operator allows the sample to contact the release element comprising the cell extractant for a period of time after the first measurement of biological analyte has been made. After the sample has contacted the release element for a period of time, a second measurement of the biological analyte is made. In some embodiments, the second measurement can be made up to about 0.5 seconds, up to about 1 second, up to about 5 seconds, up to about 10 seconds, up to about 20 seconds, up to about 30 seconds, up to about 40 seconds, up to about 60 seconds, up to about 90 seconds, up to about 120 seconds, up to about 180 seconds, about 300 seconds, at least about 10 minutes, at least about 20 minutes, at least about 60 minutes or longer after the first measurement of the biological analyte. These times are exemplary and include only the interval of time from which the first measurement for detecting the biological analyte is initiated and the time at which the second measurement for detecting the biological analyte is initiated. Initiating the detection of a biological analyte may include diluting the sample and/or adding a reagent to inhibit the activity of the cell extractant.

Preferably, the first measurement of a biological analyte is made about 1 seconds to about 240 seconds after the liquid mixture including the sample and the release element comprising a cell extractant is formed and the second measurement, which is made after the first measurement, is made about 1.5 seconds to about 540 seconds after the liquid mixture is formed. More preferably, the first measurement of a biological analyte is made about 1 second to about 180 seconds after the liquid mixture is formed and the second measurement, which is made after the first measurement, is made about 1.5 seconds to about 120 seconds after the liquid mixture is formed. Most preferably, the first measurement of a biological analyte is made about 1 second to about 5 seconds after the liquid mixture is formed and the second measurement, which is made after the first measurement, is made about 1.5 seconds to about 10 seconds after the liquid mixture is formed.

The operator compares the amount of a biological analyte detected in the first measurement to the amount of biological analyte detected in the second measurement. An increase in the amount of biological analyte detected in the second measurement is indicative of the presence of one or more live cells in the sample.

In certain methods, it may be desirable to detect the presence of live somatic cells (e.g., nonmicrobial cells). In these embodiments, the release element comprises a cell extractant that selectively releases biological analytes from somatic cells. Nonlimiting examples of somatic cell extractants include nonionic detergents, such as non-ionic ethoxylated alkylphenols, including but not limited to the ethoxylated octylphenol Triton X-100 (TX-100) and other ethoxylated alkylphenols; betaine detergents, such as carboxypropylbetaine (CB-18), NP-40, TWEEN, Tergitol, Igepal, commercially available M-NRS (Celsis, Chicago, Ill.), M-PER (Pierce, Rockford, Ill.), CelLytic M (Sigma Aldrich). Cell extractants are preferably chosen not to inactivate the analyte and its detection reagents.

In certain methods, it may be desirable to detect the presence of live microbial cells. In these embodiments, the release element can comprise a cell extractant that selectively releases biological analytes from microbial cells. Nonlimiting examples of microbial cell extractants include quaternary ammonium compounds, including benzalkonium chloride, benzethonium chloride, 'cetrimide' (a mixture of dodecyl-, tetradecyl- and hexadecyl-trimethylammonium bromide), cetylpyridium chloride; amines, such as triethylamine (TEA) and triethanolamine (TeolA); bis-Biguanides, including chlorhexidine, alexidine and polyhexamethylene biguanide dialkyl ammonium salts, including N-(n-dodecyl)-diethanolamine, antibiotics, such as polymyxin B (e.g., polymyxin B1 and polymyxin B2), polymyxin-beta-nonapeptide (PMBN); alkylglucoside or alkylthioglucoside, such as Octyl-β-D-1-thioglucopyranoside (see U.S. Pat. No. 6,174,704 herein incorporated by reference in its entirety); nonionic detergents, such as non-ionic ethoxylated alkylphenols, including but not limited to the ethoxylated octylphenol Triton X-100 (TX-100) and other ethoxylated alkylphenols; betaine detergents, such as carboxypropylbetaine (CB-18); and cationic, antibacterial, pore forming, membrane-active, and/or cell wall-active polymers, such as polylysine, nisin, magainin, melittin, phospholipase $A_2$, phospholipase $A_2$ activating peptide (PLAP); bacteriophage; and the like. See e.g., Morbe et al., Microbiol. Res. (1997) vol. 152, pp. 385-394, and U.S. Pat. No. 4,303,752 disclosing ionic surface active compounds which are incorporated herein by reference in their entirety. Cell extractants are preferably chosen not to inactivate the biological analyte and/or a detection reagent used to detect the biological analyte.

In certain alternative methods to detect the presence of live microbial cells in a sample, the sample can be pretreated with a somatic cell extractant for a period of time (e.g., the sample is contacted with a somatic cell extractant for a sufficient period of time to extract somatic cells before a liquid mixture including the sample and a release element comprising a microbial cell extractant is formed). In the alternative embodiment, the amount of biological analyte detected at the first measurement will include any biological analyte that was released by the somatic cells and the amount of additional biological analyte, if any, detected in the second measurement will include biological analyte from live microbial cells in the sample.

Methods to detect the presence of a microorganism in a sample can include the use of the detection devices disclosed herein. In certain embodiments, the method comprises providing i) a sample, ii) a detection article comprising a housing with first and second receptacles and an opening configured to receive the sample, iii) a cell concentration agent, and iv) a means for isolating and transferring the cell concentration agent from a first (e.g., upper) receptacle to a second (e.g., lower) receptacle in the housing, and v) a release element comprising a cell extractant. In these embodiments, the detection device can comprise any one of the detection devices 100, 200, 300, or 400, shown in FIGS. 1-4. Optionally, the detection device can comprise the cell concentration agent and/or the release element.

The method further comprises transferring the sample into a first receptacle in the housing wherein, in a liquid medium, the sample material is contacted with the cell concentration agent. The sample can comprise liquids, solids, semi-solids, or combinations thereof, which are transferred into the first receptacle of the housing. If the sample does not comprise a liquid medium, a liquid medium (e.g., water or a buffered solution) can be added to the first receptacle. A cell concentration agent is added to the liquid sample. The cell concentration agent is allowed to contact the liquid sample for a period of time. Optionally, the mixture can be mixed during the contact period by, for example, shaking, stirring, vortexing, and/or vibrating the housing. Preferably, the housing is closed (e.g., with optional cap) during the contact period to avoid loss of the sample and/or cell concentration agent.

The method further comprises isolating, from at least a portion of the liquid medium, the cell concentration agent, wherein isolating the cell concentration agent comprises transferring the cell concentration agent to a second receptacle in the housing. As described herein, there are a variety of means for isolating the cell concentration agent. Non-limiting examples of means to isolate and transfer the cell concentration agent include partitioning and transferring the cell concentration agent through a passageway using a plunger (see FIGS. 1 and 2), collecting and transferring the cell concentration agent in the cavity of a one-way valve (see FIG. 3), and concentrating and transferring the cell concentration agent using a drain valve and a plunger (see FIG. 4).

The method further comprises forming a liquid mixture comprising the isolated cell concentration agent and the release element, wherein the cell extractant is released into the mixture. The liquid mixture comprising the cell concentration agent is contacted with a release element comprising a cell extractant. The release element (e.g., a hydrogel bead) can be contacted with the liquid mixture in the first receptacle and/or second receptacle of the housing. In some embodiments, the second receptacle of the housing contains the release element (see FIGS. 1 and 3) and the liquid mixture is contacted with the release element when the mixture is transferred into the second receptacle. In some embodiments, the release element is disposed in a third receptacle (see FIGS. 2 and 4), through which the liquid sample passes (thereby contacting the liquid sample with the release element) as the liquid sample is transferred from the first receptacle to the second receptacle.

It is recognized that, although FIGS. 2 and 4 show the use of a plunger to pierce the frangible seals and transfer the cell concentration agent to the second receptacle, alternative instruments (e.g., a swab, a pipette, a filter) could be used instead of a plunger. In a method where such alternative instruments are used, it is preferable to remove at least a portion of the liquid sample (e.g., by decanting, pipetting, filtering, or by opening the drain valve, if present) such that the entire liquid sample is not transferred to the second receptacle when the frangible seal is pierced by the alternative instrument.

The method further comprises detecting a biological analyte. The biological analyte can be detected, as described herein, in the second receptacle of the detection device before an effective amount of cell extractant is released from the release element into the liquid mixture comprising the cell concentration agent. The biological analyte can be detected, as described herein, in the second receptacle of the detection device after an effective amount of cell extractant is released from the release element into the liquid mixture comprising the cell concentration agent. The biological analyte can be detected, as described herein, in the second receptacle of the detection device before and after an effective amount of cell extractant is released from the release element into the liquid mixture comprising the cell concentration agent.

It is anticipated that any of the methods disclosed herein can further comprise a biological growth step. The growth step is facilitated by providing a nutrient medium to support the growth of a microorganism. The nutrient medium can be mixed with the sample before, during, or after the concentration of microorganisms by the cell concentration agent. In some embodiments, the biological growth step occurs after the microorganisms have been concentrated by the cell concentration agent but before the biological analyte is detected. In some embodiments, the nutrient medium can contain nutrients and/or selective agents (e.g., salts, antibiotics) that favor the growth of certain types of microorganisms over other microorganisms that may be present in the sample.

Method of Concentrating a Particulate Cell Concentration Agent:

The present disclosure provides devices for concentrating a particulate cell concentration agent. The method includes providing a device to separate a portion of a liquid sample from a suspension the particulate material in the liquid sample. Suitable devices include, for example, the devices shown and described in FIG. 2A, FIG. 3A, FIG. 4A, FIG. 5A, FIG. 7A, and FIG. 10A. The devices each comprise a housing to contain a liquid sample including a particulate cell concentration agent and a means for separating the particulate cell concentration agent from at least a portion of the liquid sample.

In FIG. 2A, the means for separating the particulate cell concentration agent includes the taper region 218 and the plunger comprising a lower seal 256. In FIG. 3A, the means for separating the particulate cell concentration agent includes the dead-end valve 370 and valve actuator 372. In FIG. 4A, the means for separating the particulate cell concentration agent includes the drain valve 480 and valve gate 482. In FIGS. 5A and 7A, the means for separating the particulate cell concentration agent includes the plunger comprising fluid path with a filter 596 disposed in the fluid path. In FIG. 10A, the means for separating the particulate cell concentration agent includes the plunger with a scraper that is configured to permit the passage of liquid between the edge of the scraper and the housing.

The method further comprises forming a suspension of particulate cell concentration agent in a liquid sample. The suspension may be formed in the housing or it may be formed outside the housing. If the suspension is formed outside of the housing, the method further comprises transferring the suspension into the housing. The method further comprises contacting the particulate cell concentration agent with the liquid sample for a period of time sufficient to capture a microorganism. The contacting may occur in the housing. The contacting may occur outside the housing. The contacting may occur both outside and inside the housing. The method further comprises separating a portion of a liquid sample from a suspension the particulate material in the liquid sample, as described above for the devices of FIGS. 2A, 3A, 4A, 5A, 7A, and 10A.

Sample Preparation and Detection Kits:

Components and/or devices of the present disclosure can be packaged together with instructions and optionally, accessory articles or reagents, to produce sample preparation and detection kits. Thus, in one aspect, the present disclosure provides a kit comprising i) a housing comprising at least two receptacles with a passageway there between, ii) means for isolating a first receptacle from a second receptacle in the housing, iii) a cell concentration agent, and iv) means for transferring the cell concentration agent from the first receptacle to the second receptacle. The first receptacle comprises an opening configured to receive a sample. The second receptacle comprises a detection reagent disposed therein. In some embodiments, the housing can further comprise the means for isolating the first receptacle from the second receptacle, as described herein. In some embodiments, the housing can further comprise the means for transferring the cell concentration agent from the first receptacle to the second receptacle. In some embodiments, the cell concentration agent is disposed in the first receptacle of the housing.

In some embodiments, kits of the present disclosure include accessory articles or reagents that can be used with the sample preparation and detection devices. Nonlimiting examples of accessory articles include a sample acquisition device, a filter, a glove, a culture device (e.g., a petri plate, a culture tube, a PETRIFILM plate obtained from 3M Company (St. Paul, Minn.), or the like), nucleic acid isolation or amplification reagents, immunoassay devices such as lateral flow devices, ELISA plates and reagents, or any combination of two or more of the foregoing articles. Nonlimiting examples of accessory reagents include water, a buffering agent, an indicator (e.g., a pH indicator), a dye, a somatic cell extractant, a release element comprising a cell extractant, a binding partner as described herein, an enzyme, an enzyme substrate, oligonucleotides, control samples or any combination of two or more of the foregoing reagents.

EXAMPLES

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

Materials:

All bacterial cultures were obtained from The American Type Culture Collection (ATCC, Manassas, Va.), unless specified otherwise.

All water was obtained as 18 megaohm sterile deionized water using a Milli-Q™ Gradient deionization system from Millipore Corporation (Bedford, Mass.), unless specified otherwise.

CM-111: amorphous, spheroidized magnesium silicate; microspheres were obtained as 3M™ Cosmetic Microspheres CM-111 from 3M Company, St. Paul, Minn. The particles were shaped as solid spheres with particle density of 2.3 g/cc and had a surface area approximately 3.3 $m^2$/g. Ninety percent of the particles were less than about 11 microns. Fifty percent of the particles were less than about 5 microns. Ten percent of the particles were less than about 2 microns. CM-111 microspheres were prepared as described in Example 1 of U.S. Patent Application No. 61/289,213, filed on Dec. 22, 2009 and entitled "MICROORGANISM CONCENTRATION PROCESS AND CONCENTRATION AGENT FOR USE THEREIN", which is incorporated herein by reference in its entirety.

The 100× adsorption buffer containing 500 mM KCl, 100 mM $CaCl_2$, 10 mM $MgCl_2$, and 100 mM $K_2HPO_4$ at pH 7.2 was prepared and filter-sterilized prior to use.

Surface-sterilized components were contacted (wiped with or immersed in) 70% isopropyl alcohol. The excess alcohol was poured off and the components were allowed to air-dry for at least 30 minutes before use.

All chemicals were obtained from Sigma-Aldrich Chemical Company, Milwaukee, Wis., unless specified otherwise.

Example 1

Incorporation of Cell Extractant into Hydrogel Beads after Polymerization of the Hydrogel Hydrogel beads were prepared as described in example 1 of the International Patent Publication No. WO 2007/146722. Active beads were prepared by drying as described in example 19 and then soaking in active solution as described in example 23 of the International Patent Publication No. WO 2007/146722. One gram of beads was dried at 60° C. for 2 h to remove water from the beads. The dried beads were soaked in 2 grams of 50% (w/v) aqueous solutions of BARDAC 205M (Lonza Group Ltd., Valais, Switzerland) for at least 3 hrs to overnight at room temperature. After soaking, the beads were poured into a Buchner funnel to drain the beads and then rinsed with 10 to 20 ml of distilled water. The excess water was removed from the surface of the beads by blotting them with a paper towel. The beads were stored in a jar at room temperature for at least two weeks before they were used.

Example 2

Cell Concentration by Use of Microparticles and Detection Using Cell Extractant-Loaded Hydrogels and ATP Bioluminescence 3M™ CLEAN-TRACE Surface ATP system was obtained from 3M Company (St. Paul, Minn.). Pure cultures of *E. coli* ATCC 51183 were inoculated into tryptic soy broth and grown overnight at 37° C. The bacterial culture was diluted to approximately $10^6$ or $10^5$ CFU/ml in Butterfield's buffer (pH 7.2±0.2; monobasic potassium phosphate buffer solution; VWR, West Chester, Pa.).

For the "captured" reactions (Table 1), 100 microliters of the diluted bacterial suspension were added directly to individual tubes containing ten ml of deionized water (Milli-Q Biocel System, Millipore, Mass.) samples to obtain approximately $10^5$ CFU or $10^4$ CFU in ten ml, respectively. Ten mg of autoclaved CM-111 3M™ Cosmetic Microspheres (calcined amorphous spheroidized magnesium silicate powders; 3M Company; St. Paul, Minn.) were added to the tubes containing cells and mixed at room temperature for about 15 min. The particles were allowed to settle and the supernatant was removed. The particles were suspended in 100 μl of Butterfield's buffer and transferred to 1.5 ml microfuge tubes. Four hundred microliters of luciferase/luciferin liquid reagent solution from CLEAN-TRACE surface ATP system was added to the tubes.

For the control reactions ("control", Table 1), 100 μl of approximately $10^6$ or $10^5$ CFU/ml cell suspension were added to 1.5 ml microfuge tubes and 400 μl of luciferase/luciferin liquid reagent solution from Clean-Trace surface ATP system was added to the tubes. Immediately after adding the reagent, hydrogel beads (about 11 mg) containing a cell extractant were added to individual tubes and relative light units (RLUs) measurements were recorded at 10 sec intervals in a benchtop luminometer (20/20n single tube luminometer from Turner Biosystems, Sunnyvale, Calif.). Luminescence measurements were obtained from the luminometer using 20/20n SIS software that was provided with the luminometer. The light signal was integrated for 1 second and the results, expressed in RLU, are presented in Table 1. The data indicate that, using the protocol described herein, the microparticles were able to capture the cells and the cell extractant released from the hydrogel beads was able to extract about one half of ATP from the microbial cells that had been diluted into the larger (10 mL) volume, as compared to the control reaction with a similar number of undiluted cells. The results further indicate that ATP released from the cells reacted with the ATP-detection reagents, which resulted in measurable bioluminescence.

TABLE 1

Detection of ATP from *E. coli* cells coupled to a cell concentration agent and exposed to microbial cell extractants released from a hydrogel. Values expressed in the table are relative light units (RLUs).

| Time | Control | | Captured | |
|---|---|---|---|---|
| (sec) | $10^4$ Cfu | $10^5$ Cfu | $10^4$ Cfu | $10^5$ Cfu |
| 10 | 1226 | 2552 | 904 | 1648 |
| 20 | 1239 | 2648 | 948 | 1735 |
| 30 | 1265 | 2681 | 1000 | 1735 |
| 40 | 1272 | 2820 | 1067 | 1786 |
| 50 | 1280 | 3152 | 1107 | 1818 |
| 60 | 1312 | 3914 | 1147 | 1948 |
| 70 | 1352 | 4960 | 1178 | 2139 |
| 80 | 1393 | 6391 | 1197 | 2388 |
| 90 | 1440 | 8258 | 1226 | 2732 |
| 100 | 1538 | 10230 | 1250 | 3188 |
| 120 | 1618 | 11859 | 1260 | 3820 |
| 130 | 1704 | 12969 | 1286 | 4681 |
| 140 | 1838 | 13527 | 1297 | 5842 |
| 150 | 1905 | 13759 | 1318 | 6721 |
| 160 | 2006 | 13735 | 1309 | 6675 |
| 170 | 2088 | 13762 | 1314 | 6513 |
| 180 | 2119 | 13537 | 1330 | 6428 |
| 190 | 2169 | 13426 | 1363 | 6321 |
| 200 | 2140 | 13353 | 1375 | 6220 |
| 210 | 2141 | 13128 | 1342 | 6196 |
| 220 | 2143 | 13014 | 1389 | 6142 |
| 230 | 2155 | 12903 | 1381 | 6076 |
| 240 | 2110 | 12780 | 1401 | 6023 |

Example 3

Detection of Microbial Cells in a Unitary Sample Preparation and Detection Device Using an ATP Bioluminescence Detection System A unitary sample preparation and detection device 200, as shown in FIG. 2, is used in this Example. The device contains approximately 10 mg of autoclaved CM-111 3M Cosmetic Microspheres in the first receptacle 220. Second receptacle 224 contains a liquid detection reagent 265, which consists of approximately 0.6 milliliters of the luciferase/luciferin liquid reagent solution from a CLEAN-TRACE surface ATP system. The third receptacle 226 contains two BARDAC 205M beads made according to Preparative Example 5 of PCT International Publication No. WO 2010/039627. Ten milliliters of sterile deionized water is added to the first receptacle 220 of the unitary devices 200 immediately before use.

*E. coli* overnight cultures are prepared as described in Example 2. The bacterial culture is diluted to approximately $10^6$ or $10^5$ CFU/ml in Butterfield's buffer. One hundred microliters of the diluted suspension are pipetted directly into first receptacle 220 of the unitary devices 200 to obtain a suspension of approximately $10^5$ CFU or $10^4$ CFU in ten milliliters, respectively. The cap 278 is used to close the housing 210 and the bacterial suspension is mixed with the microspheres (cell concentration agent 230) at room temperature and allowed to settle into the passageway 216. The cap 278 is removed and the plunger 250 is inserted to transfer a portion of the liquid sample containing the settled microspheres and hydrogel beads into the second receptacle 224, which contains the ATP detection reagents. The unitary device is immediately inserted into the reading chamber of a luminometer (for example, a NG Luminometer, UNG2) and RLU measurements are recorded at 10 sec interval using the Unplanned Testing mode of the UNG2 luminometer. RLU measurements are collected until the number of RLUs reaches a plateau. The data are downloaded using the software provided with the NG luminometer. The data will indicate that the microbial cells are concentrated by the microspheres, the cell extractant is released by the hydrogel, the cell extractant causes the release of ATP from the cells, and the ATP released from the cells is detected by the ATP detection system.

Example 4

Detection of Microbial Cells in a Unitary Sample Preparation and Detection Device Using an ATP Bioluminescence Detection System A unitary sample preparation and detection device 300, as shown in FIG. 3, is used in this Example. The valve actuator 372 is positioned such that the valve cavity 374 is in fluid communication with the first receptacle 320 prior to use. The device contains approximately 10 mg of autoclaved CM-111 3M Cosmetic Microspheres in the first receptacle 320. Second receptacle 324 contains a liquid detection reagent 365, which consists of approximately 0.6 milliliters of the luciferase/luciferin liquid reagent solution from a Clean-Trace surface ATP system. BARDAC 205M beads are made according to Preparative Example 5 of PCT International Publication No. WO 2010/039627. Ten milliliters of sterile deionized water is added to the first receptacle 320 of the unitary devices 300 immediately before use.

*E. coli* overnight cultures are prepared as described in Example 2. The bacterial culture is diluted to approximately $10^6$ or $10^5$ CFU/ml in Butterfield's buffer. One hundred microliters of the diluted suspension are pipetted directly into first receptacle 320 of the unitary devices 300 to obtain a suspension of approximately $10^5$ CFU or $10^4$ CFU in ten milliliters, respectively. The cap 378 is used to close the housing 310 and the bacterial suspension is mixed with the microspheres (cell concentration agent 330) at room temperature and allowed to settle into the valve cavity 374. The cap 378 is removed and two BARDAC 205M beads (release element 362) are dropped into the housing 310. Immediately after the beads settle into the valve cavity 374, the valve actuator 372 is turned to transfer the portion of the liquid sample in the valve cavity (containing the cell concentration agent 330 and the release element 362) into the second receptacle 324 containing the ATP detection reagents. The unitary device is immediately inserted into the reading chamber of a luminometer (for example, a NG Luminometer, UNG2) and RLU measurements are recorded at 10 sec interval using the Unplanned Testing mode of the UNG2 luminometer. RLU measurements are collected until the number of RLUs reaches a plateau. The data are downloaded using the software provided with the NG luminometer. The data will indicate that the microbial cells are concentrated by the microspheres, the cell extractant is released by the release element, the cell extractant causes the release of ATP from the cells, and the ATP released from the cells is detected by the ATP detection system.

Example 5

Preparation of Detection Devices

Type I devices: For these detection devices, housings similar to the housing of FIG. 10A were constructed with the differences noted below. Reference numbers below refer to the corresponding parts in FIG. 10A. The upper parts 1012 and lower parts 1014 of the housing 1100 were obtained using the analogous components from 3M Clean-Trace™ surface ATP tests (obtained from 3M Company, Bridgend, UK). A collector 1067 with a frangible seal 1068 coupled thereto was press-fit into the upper portion of the lower part 1014; with the frangible seal 1068 facing the lower part 1014 of the housing 1100. The upper part 1012 was coupled to the lower part 1014 using a 2 cm section of 3:1 polyolefin dual wall adhesive lined heat shrink film obtained from buyheatshrink.com (part #_HSC3A-050-cc, 1.5 cm in diameter) using a heat gun (Master Appliances Corp, Racine, Wis.).

For these detection devices, plungers similar to the plunger of FIG. 2A were constructed. Reference numbers below refer to the corresponding parts in FIG. 2A. The plunger (250) was assembled using a portion of the polyolefin plastic handle (252) from a 3M Clean-Trace™ surface ATP test, a brass metal shaft (251) and an acetal piercing member 259. The handle 252 and piercing member 259 were attached to the ends of the brass shaft via threaded connections. The brass metal shaft was 11.5 cm long and 3.9 mm in diameter. A 6 mm, 6-23 thread was produced on each end of the shaft using a lathe. The piercing member 259 was fabricated from ½-inch (12.7 mm) acetal copolymer rod (part number 8497K211, obtained from McMASTER-CARR, Santa Fe Springs, Calif.) using a 10" Southbend lathe. An O ring (Buna N AS568A Dash Number 010 obtained from McMASTER-CARR) was used as the lower seal 256 and was attached to the plunger 250 approximately 11.5 mm above the piercing end 259. The plunger was surface-sterilized before each use.

Type II devices: These detection devices were assembled using a plunger similar to that shown and described in FIGS. 5A with a tip similar to that shown in FIG. 6A. The housing was constructed as described for the Type I devices. The tip of the plunger was fabricated from ½-inch (12.7 mm) acetal copolymer rod (part number 8497K211, obtained from McMASTER-CARR, Santa Fe Springs, Calif.) using a 10" Southbend lathe. A duckbill one-way valve and a plastic retaining washer were press-fit into the recessed opening of the body of the tip of the plunger. The filter was made by machining a POREX filter (part number X6854 from Porex Corporation, Fairburn, Ga.) to the shape shown in FIG. 6A and dimensioning one end to press-fit into the recessed opening of the tip and hold the valve and retaining washer in place. The plunger was surface-sterilized before each use.

Type III devices: Detection devices similar to those shown in FIG. 10A were constructed with the differences noted below. Reference numbers below refer to the corresponding parts in FIG. 10A. The upper parts 1012 and lower parts 1014 of the housing 1100 were obtained using the analogous components from 3M Clean-Trace™ surface ATP tests (obtained from 3M Company, Bridgend, UK). A collector 1067 with a frangible seal 1068 coupled thereto was press-fit into the upper portion of the lower part 514; with the frangible seal 1068 facing the lower part 1014 of the housing 1100. The upper part 1012 was coupled to the lower part 1014 using a 2 cm section of 3:1 polyolefin dual wall adhesive lined heat shrink film obtained from buyheatshrink.com (part #_HSC3A-050-cc, 1.5 cm in diameter) using a heat gun (Master Appliances Corp, Racine, Wis.).

The plunger (1050) was assembled using a portion of the polyolefin plastic handle (1052) from a 3M Clean-Trace™ surface ATP test, a brass metal shaft (1051) and tip 1090. The handle 1052 and tip 1090 were attached to the ends of the brass shaft via threaded connections. The brass metal shaft was 11.5 cm long and 3.9 mm in diameter. A 6 mm, 6-23 thread was produced on each end of the shaft using a lathe. The tip 1090 was fabricated from ½-inch (12.7 mm) acetal copolymer rod (part number 8497K211, obtained from McMASTER-CARR, Santa Fe Springs, Calif.) using a 10"

Southbend lathe. An O ring 1086 was attached to the tip 1090. The tip was machined to include a retaining member 1087, as shown in FIG. 10. A scraper was constructed by die-cutting a piece of 1 mm-thick polyurethane rubber and slipping it into the retaining member 1087. The outer diameter of the scraper 1086 was dimensioned to provide a tight fit with the inside of the housing 1010. The plunger was surface-sterilized before each use.

Example 6

Capture of E coli from Spiked Water with Particulate Concentration Agents Using a Type I Device An isolated colony of E. coli (ATCC 51813) from a Tryptic Soy Agar plate (Becton Dickinson, Sparks, Md.) was used to inoculate 5 ml Tryptic Soy Broth (Becton Dickinson, Sparks, Md.) and incubated overnight in a 37° C. incubator. The overnight culture containing approximately $10^9$ colony forming units/ml (CFU/ml) was diluted 1:10,000 (to approximately $10^5$ CFU/mL, hereinafter called "initial diluted suspension") in filter sterilized 18 megaohm water. Five hundred microliters of the diluted culture were transferred to 50 ml of filter sterilized 18 megaohm water, resulting in a final concentration of about approximately 1000/ml.

An aliquot (0.5 mL) of 100× Adsorption Buffer (pH 7.2) was added to the 50 mL diluted E. coli suspension (hereinafter called "spiked water sample"). The contents were mixed by manual mixing for about a minute.

An amount of 10 mg of steam sterilized CM-111 was weighed and added to Type I devices prepared as described in example 5. A 10 ml volume of the spiked water sample was added to each device and the devices were capped with surface sterilized Para film. The contents were mixed by shaking manually at room temperature (25° C.) for about 30 seconds.

After mixing, the devices were incubated for various time periods (1, 5, 10 and 20 minutes, respectively) on a Thermolyne Vari Mix™ rocking platform (Barnstead International, Iowa, 14 cycles/minute). After the incubation the tubes were set on the bench top for 10 minutes to settle the particulate concentration agent, CM-111. After settling, Para film wrapping was removed and the pre-sterilized plunger device was used to pierce the foil seal and deposit the settled CM-111 agent into the lower part of the device. The supernatant was removed by using a pipette, and the lower part of the device (which contained the cell concentration agent) was separated from the upper part of the device using a razor blade. The settled CM-111 concentration agent (in approximately 100 microliters of water) was removed from the device; diluted 1:100 in sterile water, and one-milliliter aliquots of the diluted concentration agent were plated on 3M™ Petrifilm™ Aerobic Count Plate (3M Company, St. Paul, Minn.) according to the manufacturer's instructions.

As a control, the initial diluted suspension was further diluted 1:1000 dilution in sterile water and was plated as on 3M™ Petrifilm™ Aerobic Count Plate (3M Company, St. Paul, Minn.) according to the manufacturer's instructions. The particulate materials were also plated on Petrifilm™ Aerobic Count Plate as sterility controls. The plates were incubated overnight in a 37° C. incubator (VWR Orbital Shaker Incubator, VWR, West Chester, Pa.).

All plates were analyzed by using 3M™ Petrifilm™ Plate Reader (3M Company, St. Paul, Minn.) according to the manufacturer's instructions and colony counts were obtained. The results are shown in Table 2. The results were calculated using the following formula:

Capture efficiency=(Number of colonies on concentration agent/Total Number of colonies in the spiked control)×100

TABLE 2

Concentration/capture of E. coli from 10 ml sample. All data represent the average of two replicate tests per experiment.

| Sample | % Control | St dev |
|--------|-----------|--------|
| 1 min  | 8         | 4      |
| 5 min  | 34        | 4      |
| 10 min | 33        | 11     |
| 20 min | 80        | 10     |

Example 7

Concentration of E coli Using CM-111 using a Type III Device

An isolated E. coli (ATCC 51813) colony was inoculated from a streak plate into 5 ml Tryptic Soy Broth (TSB, Becton Dickinson, Sparks, Md.) and incubated at 37° C. for 18-20 hours. This overnight culture at ~$10^9$ colony forming units/ml was diluted in sterile-filtered deionized water (MilliQ, Millipore, Mass.) and spiked in 10 ml of sterile-filtered deionized water to obtain final concentration of $1\times10^3$/ml and $1\times10^4$/ml (approximately $1\times10^4$/ml cfu's and approximately $1\times10^5$/ml cfu's total). The spiked water was added to the housing of a Type III device containing 10 mg pre-sterilized (121° C., 15 minutes) powder of CM-111 (Cosmetic Microspheres-111, 3M Company, St Paul) and 100 microliters of the 100× Adsorption Buffer (pH 7.2). The housing was sealed with surface sterilized Parafilm and placed on a rocking platform The capped devices were then incubated at room temperature (25° C.) for 5 minutes contact time on a Thermolyne Vari Mix™ rocking platform (Barnstead International, Iowa, 14 cycles/minute). The devices were then allowed to stand without shaking (to allow the particles to settle by gravity force) for 5 minutes (total elapsed time for rocking and settling=10 minutes), the Parafilm was removed and the Type II device plunger inserted into the housing and was urged toward the bottom of the housing to separate the CM-111 particles from the bulk sample. When the plunger broke the frangible seal, the CM-111 particles, suspended in about 0.1 mL of the liquid sample, was transferred to the second receptacle of the housing. The CM-111 particles were retrieved from the second receptacle and transferred to a 1.5 ml sterile microfuge tube. A 100 microliter volume of the BacTiter-Glo™ reagent (Promega, Madison, Wis.) was added to the pellet, mixed by vortexing for 5 seconds on a VWR Fixed Speed Vortex Mixer (3200 rpm for 5 seconds) and read on a tabletop luminometer (FB12 Single Tube Luminometer, Berthold Detection Systems USA, Oak Ridge, Tenn.). A positive control ("100% signal") was prepared by testing a 100 microliter volume from a $1\times10^5$/ml and $1\times10^6$/ml suspension of the E. coli cells. Results were calculated using the formula below and tabulated in Table 3 below:

ATP Signal % Capture efficiency =(RLUs on CM-111 pellet/RLUS from 100% signal)×100

RLU=Relative Luciferase Units.

TABLE 3

Concentration and detection of *E. coli* by
ATP bioluminescence using Type III device

| Sample | ATP signal in RLUs | ATP signal Capture efficiency (%) |
|---|---|---|
| *E. coli* (1 × 10$^4$ cells) control (100% signal) | 30,866 | N/A |
| *E. coli* (1 × 10$^5$ cells) control (100% signal) | 176,933 | N/A |
| CM-111 pellet from ~1 × 10$^3$/ml sample | 27,589 | 89 |
| CM-111 pellet from ~1 × 10$^4$/ml sample | 94,840 | 54 |

N = 2, Std deviation <10%, Data normalized to water alone (16,464 RLUs) background for *E. coli* controls and normalized to unreacted CM-111 (41,424 RLUs) background for the CM-111 pellets contacted with bacteria.

From above example it can be seen that the particulate capture agents can be used to concentrate bacteria from an aqueous sample.

Example 8

Concentration of *E coli* Using CM-111 Using a Type II Device

An isolated *E. coli* (ATCC 33090) colony was inoculated from a streak plate into 5 ml Tryptic Soy Broth (, TSB, Becton Dickinson, Sparks, Md.) and incubated at 37° C. for 18-20 hours. This overnight culture at approximately 10$^8$ colony forming units/ml was diluted in sterile-filtered deionized water (MilliQ, Millipore, Mass.) and spiked in 10 ml of sterile-filtered deionized water to obtain final concentration of 10$^3$/ml (approximately 10$^4$ cfu's total). The spiked water was added to the device already containing 10 mg pre-sterilized (121° C., 15 minutes) powder of CM-111 (Cosmetic Microspheres-111, 3M Company, St Paul) and 100 microliters of the 100× Adsorption Buffer. The device was sealed with surface sterilized Parafilm and placed on a rocking platform The capped devices were then incubated at room temperature (25° C.) for 1 and 9 minutes (total elapsed=time 2 mins and 10 minutes) on a Thermolyne Vari Mix™ rocking platform (Barnstead International, Iowa, 14 cycles/minute).

After the incubation the Parafilm was removed and the plunger was inserted into the housing until it contacted the frangible seal. By inserting the plunger further, to break the frangible seal, the *E. coli* bound CM-111 was transferred to the second receptacle of the housing along with approximately 100 microliters of the liquid sample. Control tubes containing *E. coli* without microparticles were treated similarly.

The CM-111 pellet was retrieved by cutting open the second receptacle the particles were transferred to a 1.5 ml sterile microfuge tube. A 100 microliter volume of the BacTiter-Glo™ reagent (Promega, Madison, Wis.) was added to the pellet, mixed by vortexing for 5 seconds on a VWR Fixed Speed Vortex Mixer (3200 rpm for 5 seconds) and read on a tabletop luminometer (FB12 Single Tube Luminometer, Berthold Detection Systems USA, Oak Ridge, Tenn.). For 100% signal, a 100 microliter volume from a 10$^5$/ml dilution was used. Results were calculated using the formula below and tabulated in Table 4 below:

ATP Signal % Capture efficiency=(RLUs on CM-111 pellet/RLUS from about 10$^4$ total *E coli*)×100

RLU=Relative Luciferase Units.

TABLE 4

Concentration and detection of *E. coli*
by ATP bioluminescence using Type II device

| Sample | ATP signal in RLUs | ATP signal Capture efficiency (%) |
|---|---|---|
| *E. coli* (10$^4$ cells) control | 96,544 | N/A |
| Water sample with *E. coli* (no concentration) | 25,583 | 0 |
| CM-111 pellet with concentrated *E. coli* 2 min testing time | 56,932 | 59 |
| CM-111 pellet with concentrated *E. coli* 10 min testing time | 58,543 | 61 |

N = 2, Std deviation <10%, Data normalized to water alone (27,938 RLUs) background for *E. coli* controls and normalized to unreacted CM-111 (30,611 RLUs) background for the CM-111 pellets contacted with bacteria.

Example 9

Concentration of *E coli* Using AB-CM-111 Using a Type II Device

A 10 mg aliquot of AB-CM (Adsorption buffer treated CM-111) was also tested for concentration of *E. coli* from 10 ml water using the procedure described in Example 8. The contact time was 9 minutes, 1 min to settle AB-CM using the POREX plunger. The data is tabulated in Table 5.

TABLE 5

Concentration and detection of *E. coli*
by ATP bioluminescence using Type II device

| Sample | ATP signal in RLUs | ATP signal Capture efficiency (%) |
|---|---|---|
| *E. coli* (10$^4$) control | 82,845 | N/A |
| Water sample with *E. coli* (no concentration) | 733 | 1 |
| AB-CM pellet with concentrated *E. coli* | 44,105 | 53 |

N = 2, Std deviation <10%, Data normalized to water alone (20,281 RLUs) background for *E. coli* controls and normalized to unreacted AB-CM (44,488 RLUs) background for the CM-111 pellets contacted with bacteria.

From above example it can be seen that the particulate capture agents can be used to concentrate bacteria from an aqueous sample.

Example 10

Comparative Example—Detection of *E. coli* in Unconcentrated Samples

State-of-the-art water testing comprises a method where 100 microliters of water is tested for ATP using a standard ATP bioluminescence assay (for example, 3M CLEANT-RACE Water—Free ATP Cat. No. AQF100, available from 3M Company, St. Paul, Minn.).

An overnight culture of *E. coli* (ATCC 33090) in tryptic soy broth was diluted in sterile water to produce two suspensions. Suspension A contained approximately 10$^3$ CFU/ml and Suspension B contained about 10$^5$ CFU/ml.

One hundred microliter aliquots of each suspension were mixed with 100 microliter volumes of the BacTiter-Glo™ reagent (Promega, Madison, Wis.) and the resulting bioluminescence was measured with a luminometer as described in Example 8. The results are presented in Table 6.

TABLE 6

Detection of *E. coli* by ATP bioluminescence

| Sample | ATP signal in RLUs | ATP signal Capture efficiency (%) after normalizing to water |
|---|---|---|
| *E. coli* ($10^4$) control (100% Signal) | 18,143 | N/A |
| Water sample (no *E. coli*) | 1,109 | N/A |
| Water sample with *E. coli* (no concentration) | 1,776 | 4% |

N = 2, Std deviation <10%

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A unitary sample preparation and detection device, comprising:
   a housing comprising first and second receptacles with a passageway there between;
      wherein the first receptacle comprises an opening configured to receive a sample and a cell concentration agent disposed therein;
      wherein the second receptacle includes a detection reagent disposed therein;
   a release element comprising a cell extractant, the release element disposed in the housing;
   means for isolating the first receptacle from the second receptacle and transferring the cell concentration agent from the first receptacle to the second receptacle; wherein the means for isolating the first and second receptacles of the housing includes a valve;
   wherein the release element comprises an encapsulating material that acts as a diffusion barrier to prevent instantaneous release of an effective amount of the cell extractant from the release element into an aqueous liquid when the release element contacts the aqueous liquid; and
   wherein the valve comprises a dead-end valve.

2. The device of claim 1, wherein the cell concentration agent comprises a particulate or dispersed cell concentration agent.

3. The device of claim 1, wherein the first receptacle comprises a tapered inner wall.

4. The device of claim 1, wherein the release element comprises a bead, a fiber, a ribbon or a sheet.

5. The device of claim 1, wherein the release element comprises a coated substrate.

6. The device of claim 1, further comprising a somatic cell extractant disposed in any one of the first receptacle or the second receptacle.

7. The device of claim 1, wherein the valve comprises a valve cavity that is moveable between a first position and a second position; wherein, in the first position, the valve cavity is in fluid communication with the first receptacle; and wherein, in the second position, the valve cavity is in fluid communication with the second receptacle.

8. The device of claim 7, wherein the valve cavity is dimensioned to hold the concentration agent.

* * * * *